US012593605B2

(12) United States Patent
Abidian et al.

(10) Patent No.: US 12,593,605 B2
(45) Date of Patent: Mar. 31, 2026

(54) ORGANIC SEMICONDUCTOR NANOTUBES FOR ELECTROCHEMICAL BIOELECTRONICS AND BIOSENSORS WITH TUNABLE DYNAMICS

(71) Applicant: University of Houston System, Houston, TX (US)

(72) Inventors: Mohammad Reza Abidian, Houston, TX (US); Mohammadjavad Eslamian, Houston, TX (US); Sheereen Majd, Houston, TX (US)

(73) Assignee: University of Houston System, Houston, TX (US)

( * ) Notice: Subject to any disclaimer, the term of this patent is extended or adjusted under 35 U.S.C. 154(b) by 556 days.

(21) Appl. No.: 17/812,932

(22) Filed: Jul. 15, 2022

(65) Prior Publication Data

US 2023/0028081 A1     Jan. 26, 2023

Related U.S. Application Data

(60) Provisional application No. 63/222,915, filed on Jul. 16, 2021.

(51) Int. Cl.
*A61B 5/27* (2021.01)
*A61B 5/293* (2021.01)
(Continued)

(52) U.S. Cl.
CPC ............. *H10K 85/141* (2023.02); *A61B 5/27* (2021.01); *B82Y 15/00* (2013.01); *B82Y 30/00* (2013.01);
(Continued)

(58) Field of Classification Search
CPC ....... A61B 5/268; A61B 5/293; A61B 5/6846; A61B 5/6847; A61B 5/6849; A61B 5/686;
(Continued)

(56) References Cited

U.S. PATENT DOCUMENTS 9,061,134 B2    6/2015  Askin, III et al.
9,555,583 B1    1/2017  Dirk et al.
(Continued)

FOREIGN PATENT DOCUMENTS

WO    WO2020/181155    9/2020
WO    WO2021/188089    9/2021

OTHER PUBLICATIONS

Yun, D.J. et al. Fabrication of high-performance composite electrodes composed of multiwalled carbon nanotubes and glycerol-doped poly(3,4-ethylenedioxythiophene):polystyrene sulfonate for use in organic devices. 2015, J. Mater. Chen. C, vol. 3, 7324-7335. (Year: 2015).*
(Continued)

*Primary Examiner* — Eun Hwa Kim
(74) *Attorney, Agent, or Firm* — pH IP Law

(57) ABSTRACT

In one aspect, the present disclosure provides organic semiconductors (OSNTs) as well as high-performance electrochemical devices based on the present OSNTs for the production of micro and nano-scale actuators. The present OSNTs may be used in several applications, including movable and implantable interface devices, such as flexible neural microelectrodes. Also provided herein are flexible neural microelectrodes based on conjugated polymer actuators.

12 Claims, 23 Drawing Sheets
(23 of 23 Drawing Sheet(s) Filed in Color)

(51) Int. Cl.
 B82Y 15/00 (2011.01)
 B82Y 30/00 (2011.01)
 H10K 85/10 (2023.01)
(52) U.S. Cl.
 CPC ...... H10K 85/111 (2023.02); *A61B 2562/125*
 (2013.01)
(58) Field of Classification Search
 CPC ............... A61B 5/6868; A61B 5/6883; H01B
 1/124–128; H01B 1/12; H10K 85/10–154;
 G01N 27/4146; B82Y 15/00; B82Y 30/00
 See application file for complete search history.

(56) References Cited

U.S. PATENT DOCUMENTS

| | | | | |
|---|---|---|---|---|
| 2010/0130844 | A1* | 5/2010 | Williams | ............... A61B 5/291 |
| | | | | 607/116 |
| 2010/0268312 | A1 | 10/2010 | Wallace | |
| 2020/0085375 | A1* | 3/2020 | Tolosa | ..................... A61N 1/05 |

OTHER PUBLICATIONS

Abidian et al., "Conducting-Polymer Nanotubes for Controlled Drug Release", *Advanced Materials, VCH Publishers*, 18(4), 405-409, 2006.
Abidian et al., "Conducting-Polymer Nanotubes Improved Electrical Properties, Mechanical Adhesion, Neural Attachment, and Neurite Outgrowth of Neural Electrodes", *small* 2010, 6, 421-429.
Abidian et al., "Interfacing Conducting Polymer Nanotubes with the Central Nervous System: Chronic Neural Recording using Poly(3,4-ethylenedioxythiophene) Nanotubes", *Adv. Mater.* 2009, 21, 3764-3770.
Abidian, et al., "Conducting-Polymer Nanotubes for Controlled Drug Release", *Adv. Mater.* 2006, 18, 405-409.
Bay et al., "A conducting polymer artificial muscle with 12% linear strain", *Adv. Mater.* 2003, 15, 310-313.
Berggren et al., "Organic Bioelectronics", *Adv. Mater.* 2007, 19, 3201-3213.
Carpi et al., "Biomedical applications of electroactive polymer actuators", John Wiley & Sons, 2009.
Deljoo et al., "Chemical Synthesis of Polypyrrole Nanotubes for Neural Microelectrodes", *Procedia Materials Science*, 11, 147-152, 2015.
Ding et al., "Use of Ionic Liquids as Electrolytes in Electromechanical Actuator Systems Based on Inherently Conducting Polymers", *Chem. Mater.* 2003, 15, 2392-2398.
Dingler et al., "From Understanding Mechanical Behavior to Curvature Prediction of Humidity-Triggered Bilayer Actuators", *Adv. Mater.* 2021, 33(9), 2007982.
Eslamian et al., "Conducting Polymer Microtubes for Bioactuators", *2019 41ˢᵗ Annual International Conference of the IEEE Engineering in Medicine and Biology Society*, pp. 3693-3696, Abstract, 2019.
Eslamian et al., in *2018 40ᵗʰ Annual International Conference of the IEEE Engineering in Medicine and Biology Society (EMBC)*, IEEE, 2018, pp. 4472-4475.
Fahlman et al., "Interfaces in organic electronics", *Nat. Rev. Mater.* 2019, 4, 627-650.
Gladisch et al., "Reversible Electronic Solid-Gel Switching of a Conjugated Polymer", *Adv. Sci.* 2020, 7, 1901144.
Hamedi et al., "Electrically Activated Paper Actuators", *Adv. Funct. Mater.* 2016, 26, 2446-2453.
Hamedi et al., "Towards woven logic from organic electronic fibres", *Nat. Mater* 2007, 6(5), 357-362.
Hu et al., "PEDOT-Based Conducting Polymer Actuators", *Frontiers in Robotics and AI* 2019, 6, 114.
International Search Report and Written Opinion for International Application No. PCT/US2022/073773 dated Jan. 4, 2024, 16 pages.
Kiefer et al., "Polymeric actuators: Solvents tune reaction-driven cation to reaction-driven anion actuation", *Sensors Actuators B: Chem.* 2016, 233, 328-336.
Kim et al., "A stable lithium-rich surface structure for lithium-rich layered cathode materials", *Nat. Commun* 2016, 7, 1-8.
Kong, et al., "Carbon nanotube and graphene-based bioinspired electrochemical actuators", *Adv. Mater.* 2014, 26, 1025-1043.
Lee et al., "Ionic Polymer-Metal Composite Actuators Based on Triple-Layered Polyelectrolytes Composed of Individually Functionalized Layers", *ACS Appl. Mater. Interfaces* 2014, 6, 1266-1271.
Lee et al., *Smart Structures and Materials 2000: Electroactive Polymer Actuators and Devices (EAPAD)*, vol. 3987, International Society for Optics and Photonics, 2000, pp. 291-299.
Li et al., "Soft and flexible PEDOTS/PSS films for applications to sot actuators", *Smart Mater. Struct.* 2014, 23(7), 074010.
Li et al., "Superfast-Response and Ultrahigh-Power-Density Electromechanical Actuators Based on Hierarchal Carbon Nanotube Electrodes and Chitosan", *Nano Lett.* 2011, 11, 4636-4641.
Lu et al., "Graphene-Stabilized Silver Nanoparticle Electrochemical Electrode for Actuator Design", *Adv. Mater.* 2013, 25, 1270-1274.
Lu et al., "Highly stable air working bimorph actuator based on a graphene nanosheet/carbon nanotube hybrid electrode", *Adv. Mater.* 2012, 24, 4317-4321.
Mukai et al., "Highly Conductive Sheets from Millimeter-Long Single-Walled Carbon Nanotubes and Ionic Liquids: Application to Fast-Moving, Low-Voltage Electromechanical Actuators Operable in Air", *Adv. Mater.* 2009, 21, 1582-1585.
Okuzaki et al., "Ionic liquid/polyurethane/PEDOT:PSS composites for electro-active polymer actuators", *Sensors Actuators B: Chem.* 2014, 194, 59-63.
Panwar et al., "Low voltage actuator using ionic polymer metal nanocomposites based on a miscible polymer blend", *J. Mater. Chem. A* 2015, 3, 19718-19727.
Parupudi et al., "Fabrication and characterization of implantable flushable electrodes for electric field-mediated drug delivery in a brain tissue-mimic agarose gel", *Electrophoresis* 2018, 39, 2262-2269.
Péraud et al., "Fluctuation-enhanced electric conductivity in electrolyte solutions", *PNAS* 2017, 114, 10829-10833.
Pomfret et al., "The Substitute Brain and the Potential of the Gel Model", *Annals of neurosciences* 2013, 20, 118.
Rivnay et al., "Organic electrochemical transistors", *Nat. Rev. Mater.* 2018, 3, 1-14.
Rousche et al., "Flexible polyimide-based intracortical electrode arrays with bioactive capability", *IEEE Trans. Biomed. Eng.* 2001, 48, 361-371.
Sansiñena et al., "High-Performance, Monolithic Polyaniline Electrochemical Actuators", *Adv. Funct. Mater.* 2003, 13, 703-709.
Santa et al., "Performance and work capacity of a polypyrrole conducting polymer linear actuator", *Synth. Met.* 1997, 90, 93-100.
Sapurina et al., "Polypyrrole nanotubes: The tuning of morphology and conductivity", *Polymer*, 113, 247-258, 2017.
Sillay et al., "Benchmarking the ERG valve tip and MRI Interventions Smart Flow neurocatheter convection-enhanced delivery system's performance in a gel model of the brain: employing infusion protocols proposed for gene therapy for Parkinson's disease", *J. Neural Eng.* 2012, 9, 026009.
Smela, "Conjugated Polymer Actuators for Biomedical Applications",*Adv. Mater.* 2003, 15, 481-494.
Smela, "Conjugated Polymer Actuators", *MRS Bull.* 2011, 33, 197-204.
Stavrinidou et al., "Direct Measurement of Ion Mobility in a Conducting Polymer", *Adv. Mater.* 2013, 25, 4488-4493.
Takeuchi et al., "Electromechanical behavior of fully plastic actuators based on bucky gel containing various internal ionic liquids", *Electrochim. Acta* 2009, 54(6), 1762-1768.
Temmer et al., "Combined chemical and electrochemical synthesis methods for metal-free polypyrrole actuators", *Sensors Actuators B: Chem.* 2012, 166, 411-418.
Terasawa et al., "A multi-walled carbon nanotube/polymer actuator that surpasses the performance of a single-walled carbon nanotube/polymer actuator", *Carbon* 2012, 50, 311-320.

(56) References Cited

OTHER PUBLICATIONS

Terasawa, et al., "High-Performance PEDOT:PSS/Single-Walled Carbon Nanotube/Ionic Liquid Actuators Combining Electrostatic Double-Layer and Faradaic Capacitors", *Langmuir* 2016, 32, 7210-7218.

Timoshenko, "Analysis of Bi-Metal Thermostats", *Josa* 1925, 11, 233-255.

Wadhwa et al., "Electrochemically controlled release of dexamethasone from conducting polymer polypyrrole coated electrode", *J. Controlled Release* 2006, 110, 531-541.

Wang et al., "High energy conversion efficiency conducting polymer actuators based on PEDOT:PSS/MWCNTs composite electrode", *RSC Adv.* 2017, 7, 31264-31271.

Wu et al., "High-Performance Hierarchical Black-Phosphorous-Based Soft Electrochemical Actuators in Bioinspired Applications", *Adv. Mater.* 2019, 31, 1806492.

Wu et al., "Ordered and Active Nanochannel Electrodie Design for High-Performance Electrochemical Actuator", *Small* 2016, 12, 4986-4992.

Yan et al., "Recent Advances on Polypyrrole Electroactuators", *Polymers* 2017, 9, 446.

Yang et al., "High-Performance Conducting Polymer Nanofiber Biosensors for Detection of Biomolecules", *Adv. Mater.* 2014, 26, 4954-4960.

* cited by examiner

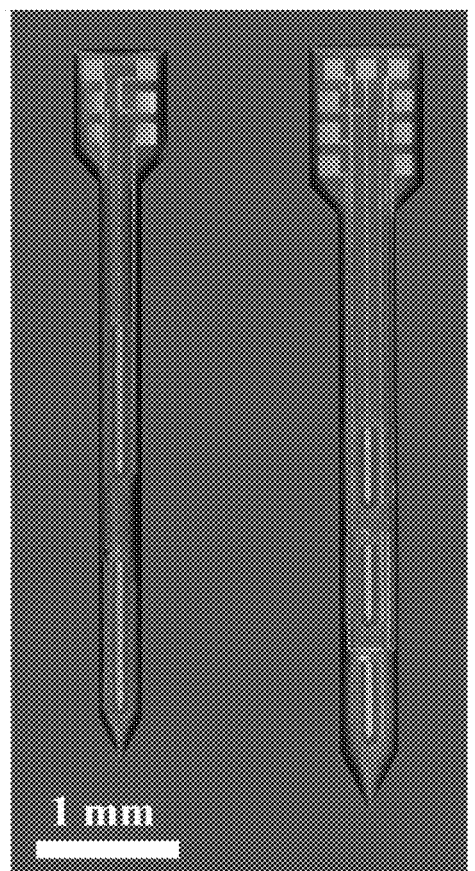
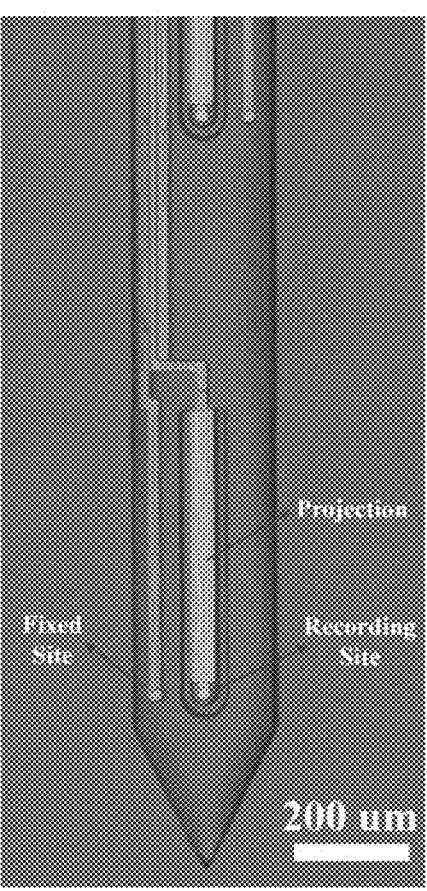
FIG. 18
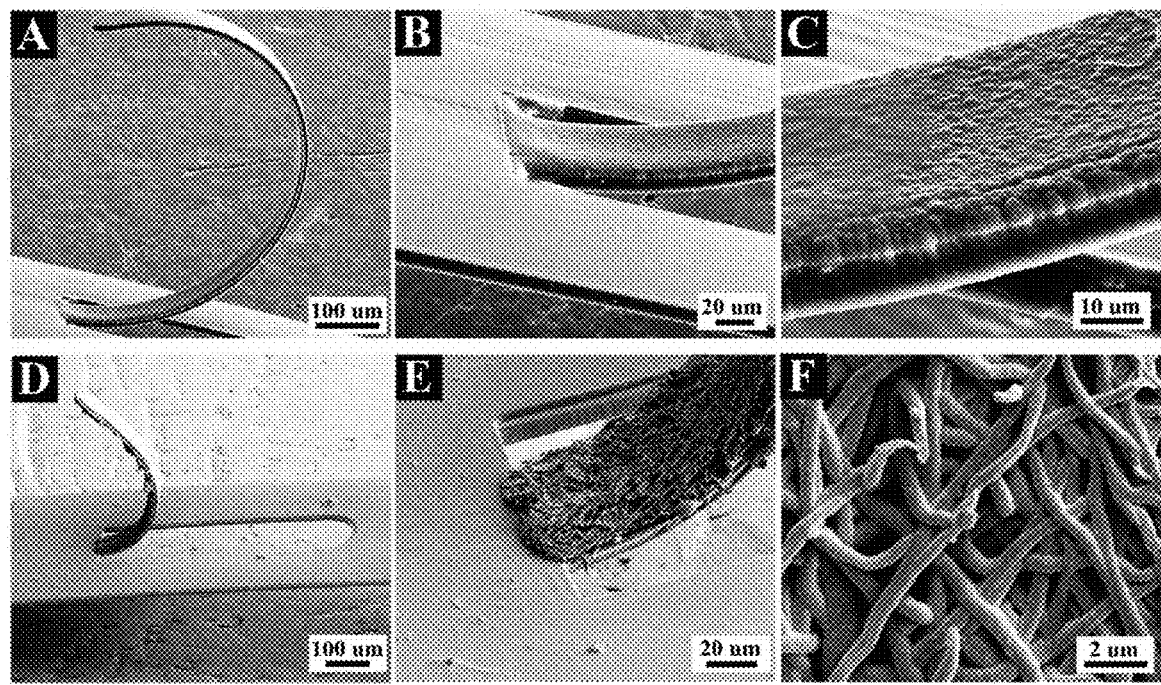
FIGS. 19A-19F

ORGANIC SEMICONDUCTOR NANOTUBES FOR ELECTROCHEMICAL BIOELECTRONICS AND BIOSENSORS WITH TUNABLE DYNAMICS

PRIORITY CLAIM

This application claims benefit of priority to U.S. Provisional Application Ser. No. 63/222,915 filed Jul. 16, 2021, the entire contents of which are hereby incorporated by reference.

The invention was made with government support under Grant No. R01 NS087224 awarded by the National Institute of Health (NIH). The government has certain rights in the invention.

1. FIELD

This disclosure relates to the fields of medicine, polymers, nanomaterials, chemistry, and neurological disorders. In particular, new structures, compositions, methods of treatment, and methods of synthesis relating to structures of conducting polymers are disclosed.

2. RELATED ART

Ions play a key role in the life of living organisms, particularly for nerve signal transduction that is essential for contractile cells to produce muscle deformation and/or motion.[1] Inspired by function of biological muscle, artificial muscles concerning ion migration into/out of electrodes (e.g., ionic polymer-metal composites) have gained much attention in biomimetic technologies.[2] Soft ionic actuators, also called electrochemical actuators, generate actuation deformation in response to applied voltage (below 1 V and up to several volts) by reversible intercalation and deintercalation of ions into/out of an electroactive layer. Such actuators have been intensively investigated for various applications in soft robotics, artificial muscles, autofocus lenses, and biomedical devices.[2a, 3] One group of these actuators is air-working electrochemical actuators that are composed of one semipermeable ion-conductive electrolyte polymer membrane sandwiched between two electroactive layers.[4] This type of actuators often utilizes conductive carbon nanomaterials such as carbon nanotubes, [5] graphene,[6] and graphdiyne.[7] Recent advances in materials science and fabrication techniques have enabled development of durable and lightweight air working electrochemical actuators capable of generating large strains and fast responses.[8] Most of these actuators are however, composed of multiple electroactive materials and thus, require rather complex fabrication processes.

Another group of electrochemical actuators are those that operate in an ion-conductive electrolyte. These actuators are commonly composed of an electroactive film layer deposited on an electrode to construct a bilayer actuator device. The volume change of the electroactive layer in a bilayer configuration can be used to generate out-of-plain movement and produce bending deformation.[9] Among materials that have been utilized as the electroactive layer in these actuators, organic semiconductors (OSs) (i.e., π-conjugated polymers (CPs)) such as polyaniline, polypyrrole, and poly3,4-ethylenedioxythiophene, exhibit unique properties as they can operate under low voltages and hold strain under voltage or open circuit.[10] OS films with controlled thickness can be electrochemically synthesized and miniaturized, making them versatile for various applications such as medical devices and artificial muscles.[11] The volume changes in OS actuators is governed by transportation of ions and solvent molecules under redox reactions.[12] Owing to their good biocompatibility, OSs have been used in biomedical devices and actuators operating in biofluids. [3d, 11b, 13] Among OSs, polypyrrole has been extensively studied for electrochemical actuators as it can withstand relatively large actuation strains/stresses and be readily electrodeposited to form dense or porous films in aqueous and organic electrolytes for large scale production.[14] However, achievement of large deformation strains with fast response time and high actuation stability remains a challenge for OS film-based actuators wherein the high rigidity and dense structure of the film restrict the actuator motion, limit the ion transportation, and increase the risk of delamination.[15] Recent advances in neuroscience have enabled the exploration of brain activity and neural disorders and allowed understanding of its mechanisms down to the microscopic level. Neural recording technologies have remarkably contributed to this understanding by revealing neuron activities and functional connectivity [1, 2]. Neural interfacing devices have been utilized in various clinical applications including cochlear [3] and retinal implants [4], spinal and peripheral nerve interfaces [5, 6], epilepsy monitoring devices [7], and deep brain stimulators [8]. Initiating from tungsten and silicon neural probes [9, 10], next generation neural probes such as Michigan electrodes [11], Utah arrays [12], and Neuropixels electrodes [13] have enabled advanced spatiotemporal and multifunctional interrogation of neurons. The rigid nature of these probes facilitates direct implantation and accurate localization in the brain; however, the physical and mechanical properties mismatch between the neural probe and brain tissue restricts establishment of high-resolution chronic recordings and stimulations of surrounding neurons [14]. In fact, conventional electrodes for brain interfacing are made of metals or doped silicon, which are much stiffer than biological tissues. Consequently, the mechanical mismatch between probes and brain tissue induces neuroinflammatory responses and scar formation that resulted in gradual signal loss over time [15]. The strategy to improve the mechanical and physical compatibility of neural probes with brain tissue includes electrode design and materials engineering [16]. Basically, structural design (electrode thickness) and mechanical properties (elastic modulus and Poisson's ratio) of the probes determine their bending stiffness [17] expressed as $$\text{Bending Stiffness} = \frac{Eh^3}{12(1-v^2)}.$$

Here, E is the elastic modulus, h is thickness, and v is Poisson's ratio. As the bending stiffness scales cubically with the thickness and linearly with the modulus, either reducing the thickness of the device or using low modulus materials can drastically decrease the device stiffness. Accordingly, soft materials are increasingly employed for neural electrodes to provide more mechanically-compatible interfaces while minimizing side effects [14]. Many polymers have been explored for development of flexible neural probes, including SU-8, polyimide, parylene, polydimethylsiloxane (PDMS), liquid crystal polymers, cyclic olefin polymers, polymethyl methacrylate, polycarbonate, and polystyrene [18]. Combination of material properties, processing conditions, and performance demands determine selection of a particular polymer for a device. Among all above-mentioned polymers, SU-8, polyimide, and parylene are currently on the rise within microelectromechanical systems (MEMS) as free standing films and structural elements on flexible neural probe devices [19]. Compared to the other polymers, these three are compatible with standard microfabrication techniques (i.e., photolithography and wet/dry etch), so many researchers have been motivated to develop novel strategies for processing and device construction of neural probes based on these polymers [18]. However, implantation and localization of the soft material in soft tissues is challenging, owing to additional tissue damage caused by rigid auxiliary tools used for implantation, lengthy interface recovery and micromotion of the soft electrode [20 22]. The dilemma of choosing between facile implantation of rigid probes and compatible interface of soft electrodes has called for the evolution of materials and fabrication techniques for neuronal recording technology.

Neuronal recordings using current implantable microelectrode technologies have been found to be inconsistent and/or unreliable in long-term assessments [15, 23, 24]. This limitation is the most significant impediment toward the success of emerging cortical prostheses that rely on their recording stability over the lifetime of patients who use such prosthetic devices. As an alternative to fixed microelectrodes, movable microelectrodes have been suggested as a potential approach to mitigate some of these limitations. Technologies that enable control of microelectrodes after implantation remarkably enhance the ability to (a) isolate activity from single neurons (b) maintain stable neuronal recordings over longer durations (c) maintain the signal-to-noise ratio in the neuronal recordings (d) seek neurons of interest after implantation [25]. There have been several attempts to create movable probes, but none of them have successfully met all the requirements for safe, reliable, and long-term chronic use. The use of electrothermal and capacitive actuators has been demonstrated for silicon probes embedded in the brain cap to vertically move neural probes which provided good signal recording for 12 weeks in vivo [26]. Cham and coworkers also developed microwire probes which move vertically in the brain by manually adjusting a screw on the head cap of the animal [27]. Pang et al. developed an electrolysis-based parylene balloon actuator in order to move neural probes [28].

In general, actuation methods can either be included in the microfabrication of neural probes or can be integrated in post-fabrication process. Capacitive, electrostatic, electrothermal, shape memory alloys, and piezoelectric actuation methods are usually incorporated at the microfabrication level. However, an actuation method that could be incorporated post-processing may allow for fabrication flexibility. In addition, actuation methods require to be evolved for biocompatible and safe use in the brain tissue, their power consumption, heat dissipation, voltage requirements, and overall size. Mechanisms of producing actuation at the micro-scale are limited and usually require incorporation during the fabrication processes [25]. Therefore, an actuation technology that can be incorporated post standard microfabrication would have advantage over others that require process integration. Thus, there is an unmet need for conjugated polymer actuators that can be electrically polymerized on projections of interest with low power requirements for applications in medical microdevices.

SUMMARY

In some aspects, the present disclosure provides An organic semiconductor nanotube (OSNT) comprising at least one conducting polymer.

In some aspects, the at least one conducting polymer is polypyrrole, polyaniline, or poly3,4-ethylenedioxythiophene. In particular aspects, the at least one conducting polymer is polypyrrole.

In certain aspects, the OSNT further comprises a dopant. In some aspects, the dopant is a negatively charged molecule, such as a net negatively charged molecule. In some aspect, the dopant is polystyrene sulfonate (PSS).

In some aspects, the nanotube has a diameter of about 500 nm to 700 nm, such as about 600 nm to 650 nm, such as about 610 to about 645 nm. In certain aspects, the OSNT has an ion exchange of about 150 to about 200 g cm$^{-3}$, an elastic modulus of about 5 to 10 MPa, a charge storage density of about 400 to about 500 mC cm$^{-2}$), and/or a specific capacitance about 100 to about 200 F g$^{-1}$.

Further provided herein is a method for producing the OSNT of the present embodiments comprising (a) electrospinning a non-conductive polymer onto a conductive surface using a syringe pump to form template nanofibers; (b) electrochemically depositing a conductive polymer around the template nanofibers; and (c) adding an organic solvent to remove the template nanofibers to form the OSNTs.

In some aspects, the electrospinning is performed in an electric field of about 0.9 to about 1.0 kV cm$^{-1}$. In certain aspects, the non-conductive polymer is a poly(lactide), poly(glycolide), or poly(lactide-co-glycolide). In certain aspects, the non-conductive polymer is a poly-L-(lactide) (PLLA). In some aspects, the non-conductive polymer is in a solution comprising an organic solvent. In certain aspects, the non-conductive polymer is present at a concentration of 1% w/w to 10% w/w in the solution, such as 3% w/w in the solution.

In certain aspects, the solution further comprises an organic salt, such as benzyl triethylammonium chloride. In some aspects, the conductive polymer is polypyrrole. In certain aspects, the polypyrrole is comprised in an electrolyte solution. In some aspects, the electrolyte solution further comprises a dopant. In certain aspects, the dopant is a negatively charged molecule. In some aspects, the dopant is a net negatively charged molecule, such as poly(sodium 4-styrenesulfonate) (NaPSS).

In some aspects, the syringe has a gauge from about 20 to about 30, such as 21, 22, 23, 24, or 25. In certain aspects, the conductive surface comprises a metal coating. In some aspects, the metal coating is a gold coating, such as wherein the gold coating has a thickness of about 0.3 μm. In some aspects, the organic solvent is chloroform.

A further embodiment provides an electrochemical device comprising the OSNTs of the present embodiments or aspects thereof.

In certain aspects, the device has actuation in liquid. In some aspects, the device has actuation in a gel polymer. In some aspects, the electrochemical device is further defined as a neural probe or neural interface device.

A further embodiment provides a method for producing a neural probe device comprising (a) microfabricating a probe with at least one movable projection using layer-by-layer photolithography; (b) coating the probe with a conductive metal; (c) electrospinning a non conductive polymer onto the conductive surface using a syringe pump to form template nanofibers; (d) electrochemically depositing a conductive around the template nanofibers; and (e) adding an organic solvent to remove the template nanofibers to form the neural probe device.

In some aspects, the probe comprises a layer of photoresist. In certain aspects, the probe comprises multiple layers of photoresist, such as SU-8.

In certain aspects, step (a) comprises using a silicon wafer with a thermal oxide layer as a substrate. In some aspects, the probe comprises two or three movable projections. In certain aspects, the probe comprises more than three movable projections. In some aspects, the movable projections have a length of about 0.5 mm to about 1 mm. In certain aspects, the movable projections have a width of about 25 to 75 μm and a thickness of 5 to 20 μm. In some aspects, the movable projections have a width of about 40 to 60 μm and a thickness of 10 to 15 μm.

In some aspects, the conductive metal is gold and/or chromium. In certain aspects, the gold and/or chromium are present at a thickness of 1 to 3 μm. In particular aspects, the gold and/or chromium are present at a thickness of 2 μm.

In certain aspects, the electrospinning is performed in an electric field of about 0.9 to about 1.0 kV cm$^{-1}$. In some aspects, the non-conductive polymer is a poly(lactide), poly(glycolide), or poly(lactide-co-glycolide). In certain aspects, the non-conductive polymer is a poly-L-(lactide) (PLLA). In some aspects, the non-conductive polymer is in a solution comprising an organic solvent. In some aspects, the non-conductive polymer is present at a concentration of 1% w/w to 10% w/w in the solution. In certain aspects, the non-conductive polymer is present at a concentration of 3% w/w in the solution. In some aspects, the solution further comprises an organic salt. In certain aspects, the organic salt is benzyl triethylammonium chloride. In some aspects, the conductive polymer is polypyrrole. In particular aspects, the polypyrrole is comprised in an electrolyte solution. In certain aspects, the electrolyte solution further comprises a dopant. In some aspects, the dopant is a negatively charged molecule. In some aspects, the dopant is a net negatively charged molecule, such as poly(sodium 4-styrenesulfonate) (NaPSS).

In certain aspects, the syringe has a gauge from about 20 to about 30, such as 22, 23, 24 or 25.

In some aspects, the organic solvent is chloroform. In certain aspects, the probe comprises at least one movable projection comprising a rectangular segment for actuation. In certain aspects, the movable projection further comprises a round site at the projection tip for signal recording. In some aspects, the probe further comprises a fixed recording site. In certain aspects, the fixed recording site is adjacent to the movable actuating projection.

Another embodiment provides a neural probe device produced according to present embodiments and aspects thereof. In some aspects, the device is implantable.

A further embodiment provides a neural probe device comprising at least one movable projection and organic semiconductor nanotubes (OSNTs), such as OSNTs of the present embodiments and aspects thereof.

In some aspects, the probe is coated with a conductive metal, such as chromium and/or gold. In certain aspects, the probe comprises a layer of photoresist. In some aspects, the probe comprises multiple layers of photoresist. In particular aspects, the photoresist is SU-8.

In certain aspects, the probe comprises two or three movable projections. In some aspects, the probe comprises more than three movable projections. In some aspects, the movable projections have a length of about 0.5 mm to about 1 mm. In certain aspects, the movable projections have a width of about 25 to 75 μm and a thickness of 5 to 20 μm. In some aspects, the movable projections have a width of about 40 to 60 μm and a thickness of 10 to 15 μm. In some aspects, the gold and/or chromium are present at a thickness of 1 to 3 μm. In certain aspects, the gold and/or chromium are present at a thickness of 2 μm.

In some aspects, the probe comprises polypyrrole. In certain aspects, the polypyrrole is doped with poly(sodium 4-styrenesulfonate) (NaPSS). In some aspects, the probe comprises at least one movable projection comprising a rectangular segment for actuation. In certain aspects, the movable projection further comprises a round site at the projection tip for signal recording. In some aspects, the probe further comprises a fixed recording site. In certain aspects, the fixed recording site is adjacent to the movable actuating projection. In particular aspects, the device is implantable.

A further embodiment provides a method of using a neural probe device of the present embodiments for neural recording or stimulation.

A method of using a neural probe device of the present embodiments for releasing a therapeutic agent to the neuron, such as a drug or protein.

Further provided herein is the use of the neural probe device of the present embodiments for neurochemical detection. Also provided herein is the use of the neural probe device of the present embodiments as a neural interface.

Another embodiment provides a method of using OSNTs according to the present embodiments, OSNTs produced according to the present embodiments, or a neural probe device of the present embodiments in a biosensor.

A further embodiment provides a method of using OSNTs according to the present embodiments, OSNTs produced according to the present embodiments, or a neural probe device of the present embodiments in a bioelectronic.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The patent or application file contains at least one drawing executed in color. Copies of this patent or patent application publication with color drawings(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description.

(FIG. 1A) Schematic illustrates layered design of the actuator. (FIG. 1B) Step-by-step fabrication process of the OSNTs actuator: starting with a coverslip as carrier substrate covered with a removable double-sided tape on top (a), attachment of poly(propylene) (PP) film (30 μm thick) to the removable tape (b), sputtering of a thin layer of Au (~0.3 μm thick, see FIG. 8) on the PP film (c), electrospinning of template PLLA nanofibers on the Au layer (d), electrodeposition of OS around electrospun PLLA nanofibers (~13 μm thick, see FIG. 8) (e) removal of PLLA nanofibers to form OSNTs and finally detachment of the constructed actuator from the removable tape and the carrier substrate (f). (FIG. 1C) Photographs of gold-coated substrates after electrospinning of template PLLA nanofibers and electrode-position of OS around template nanofibers followed by template removal to form OSNTs. (FIG. 1D) Scanning electron micrograph of the electrospun PLLA template nanofibers. (FIG. 1E) Scanning electron micrograph of the OSNTs. (FIGS. 1F-G) Cross-sectional scanning electron micrographs of the OSNTs layer.

(FIG. 2A) Schematic represents ions transportation and the resulting bending movement in actuation of OSNTs upon redox processes. (FIG. 2B, 2C) Composite optical micrographs showing reversible bending deformation of the OSNTs actuator in liquid and gel electrolytes during cyclic voltammetry at the scan rate of 10 mV s-1 for one full cycle. Arrows show the direction of bending during consecutive reduction (R) and oxidization (0) processes. The OSNTs were deposited on the left-side of the actuator beam. (D-I) Cyclic voltammograms (FIG. 2D, 2E), mass flux (FIG. 2F, 2G), and tip displacement (FIG. 2H, 2I) of the OSNTs actuator as a function of potential during CV cycling in liquid and gel electrolytes containing 0.1 M NaPSS within the potential range of −0.8 to +0.4 V (versus Ag/AgCl) at various scan rates of 10 mV s-1 (blue square), 50 mV s-1 (green circle), 100 mV s-1 (red upward triangle), and 200 mV s-1 (black downward triangle). All plots correspond to the 10th cycle. Arrows indicate cycling direction.

(FIGS. 3A, 3B) Composite photographs illustrate the maximum tip deflection occurs during CV cycling at different scan rates of 10, 50, 100, and 200 mV s-1 in liquid (FIG. 3A) and gel (FIG. 3B) electrolytes. (FIG. 3C-I) The OSNTs actuator response as a function of scan rate during cycling in liquid (black color) and gel (red color) electrolytes including: mass influx (FIGS. 3A, 3C), charge storage density (FIGS. 3A, 3D), maximum displacement (FIG. 3A, 3E), maximum strain (FIGS. 3A, 3F), maximum speed (FIGS. 3A, 3G), response time (FIG. 3A H), and actuation force (FIG. 3A, 3I) (±SEM, n=5). (FIG. 3A, FIG. 3J, 3K) The actuation force-displacement plots at various scan rates of 10 mV s-1 (blue square), 50 mV s-1 (green circle), 100 mV s-1 (red upward triangle), and 200 mV s-1 (black downward triangles) in liquid (FIG. 3J) and gel (FIG. 3K) electrolytes.

(FIG. 4A) Power consumption/strain percentage of the OSNTs actuator, compared with different types of soft electrochemical actuators. (FIG. 4B) Bending stability ($\delta 1$ $\delta 0$) of the OSNTs actuator over 15000 actuations at 200 mV s-1 (25 hours of continuous operation). $\delta 0$ corresponds to the actuator deflection at the first cycle, and $\delta$ is the deflection at the nth cycle. Inset represents the sample variation in the maximum tip deflection ($\delta max$) within the first 1000 actuations in liquid and gel electrolytes (±SEM, n=3). There is no significant difference in the $\delta max$ over the course of actuation in both liquid and gel electrolytes (p>0.05). (FIGS. 4C-D) Scanning electron micrographs of OSNTs before (C) and after (D) actuation at scan rate of 200 mV s-1 for 1000 times. (FIGS. 4E-F) Optical microphotographs of the transverse cross-section of the actuator after actuation for 1000 times at scan rate of 200 mV s-1.

The diameter of PLLA nanofibers and OSNTs are 140±4 nm and 626±16 nm, respectively (n=100).

Figure 6:
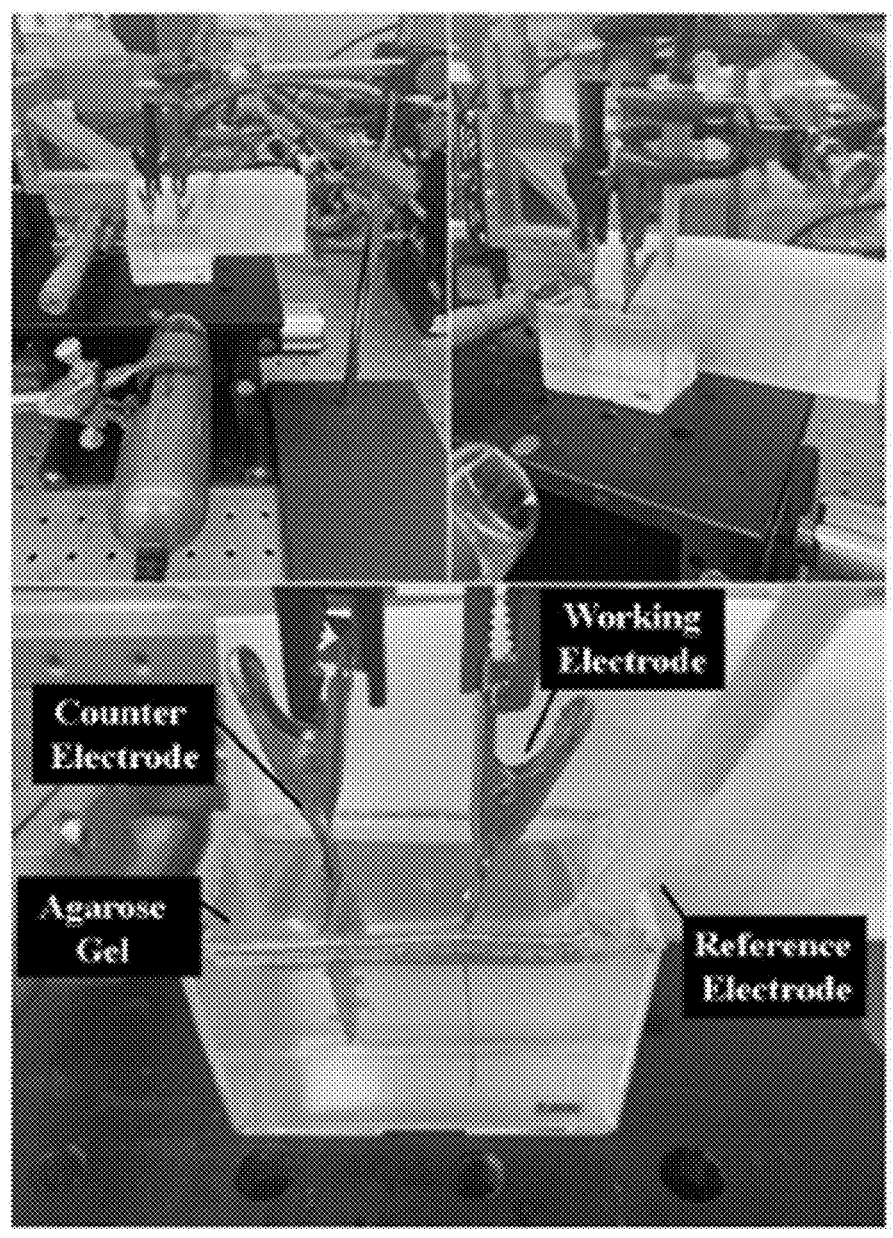

FIG. 6: Photographs of the actuation setup at different view angles. Images show the three-electrode configuration was used for CV. A platinum foil served as the counter electrode, an Ag/AgCl electrode as reference electrode, and the actuator as working electrode. In these photos, the electrolyte is in hydrogel.

Figure 7:
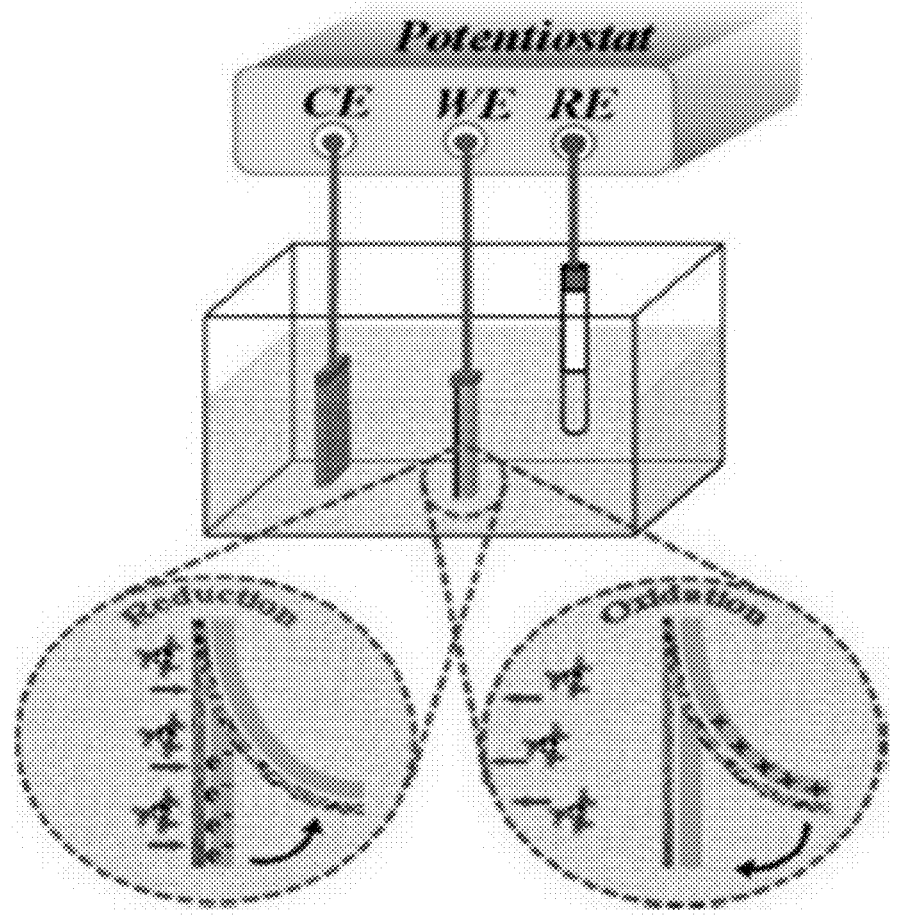
Figures 8A, 8B, 8C, 8D:
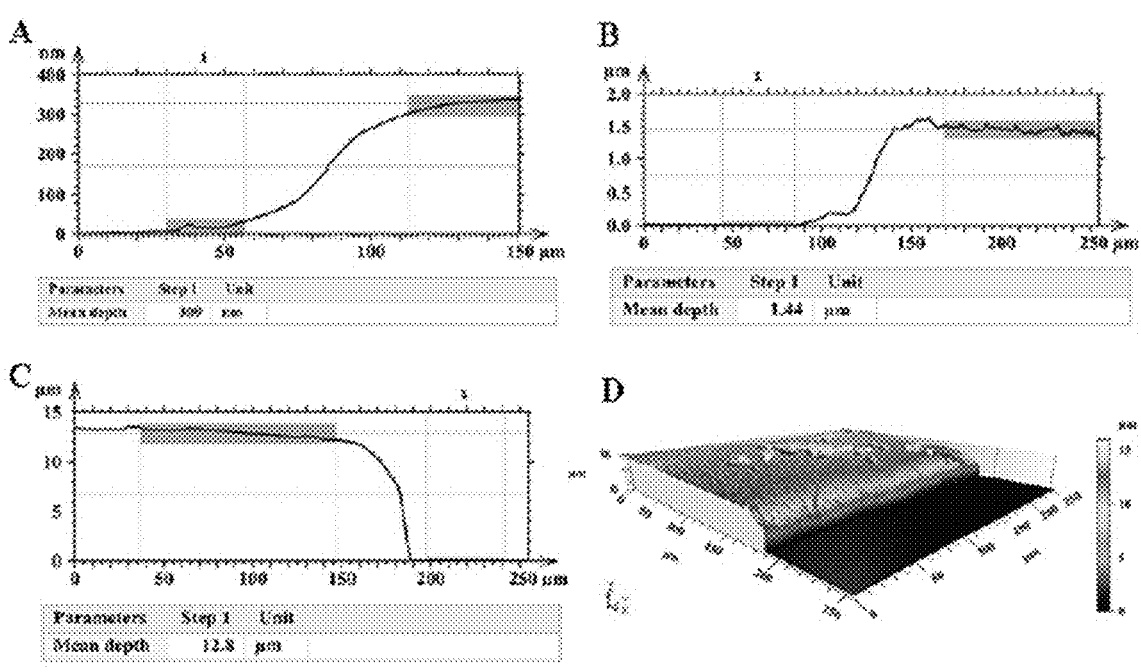

FIG. 7: A schematic illustrates the actuator deflection in response to transportation of solvated cations into/out of the OSNTs during CV. The actuator deflects counter-clockwise upon reduction, when the solvated cations transport into the OSNTs layer. Subsequently, the actuator deflects clockwise upon oxidation process, as the solvated cations leave the OSNTs towards surrounding electrolyte, until it retains its initial position prior to reduction.

FIGS. 8A-8D: Step-height measurements for: (FIG. 8A) the Au layer, (FIG. 8B) OSNTs constructed on an EQCM crystal for mass flux measurements, and (FIG. 8C) OSNTs constructed on the bending beam actuators. Measurements represent the mean profiles obtained from a series of profiles (graph A: 150 profiles, graphs B and C: 250 profiles). As indicated by orange boxes on the graphs, the step-heights were determined according to standard ISO 5436-1 and given as the mean depth in the corresponding tables. (FIG. 8D) A 3D reconstructed confocal image represents the surface topography of the OSNTs layer.

Figure 9:
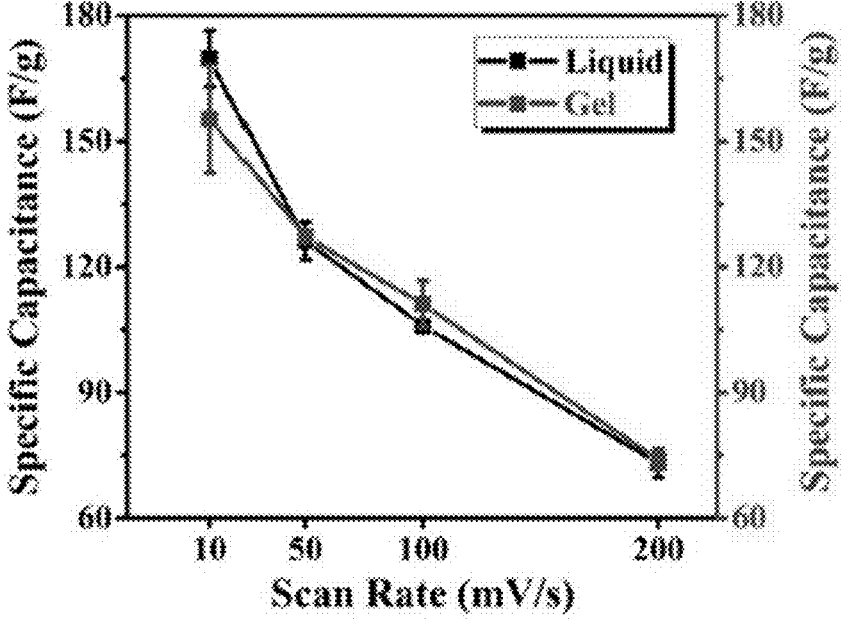

FIG. 9: Specific capacitance of the OSNTs actuator as a function of CV scan rate during cycling in liquid (black color) and gel (red color) electrolytes.

Figure 10:
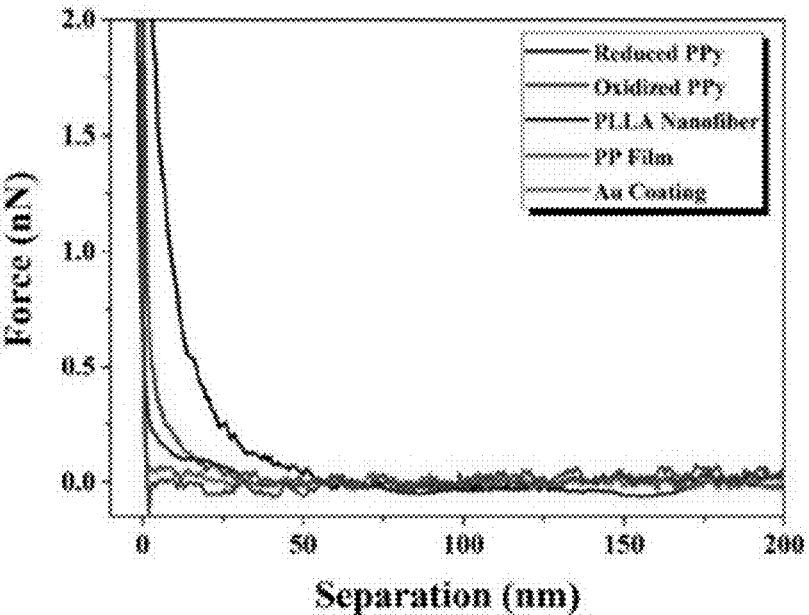

FIG. 10: Representative force-separation curves for the device components, including PP film, Au coating, and OS (reduced and oxidized states). The presented data were obtained using AFM in fluid in either contact mode and/or peak force mode.

Figure 11:
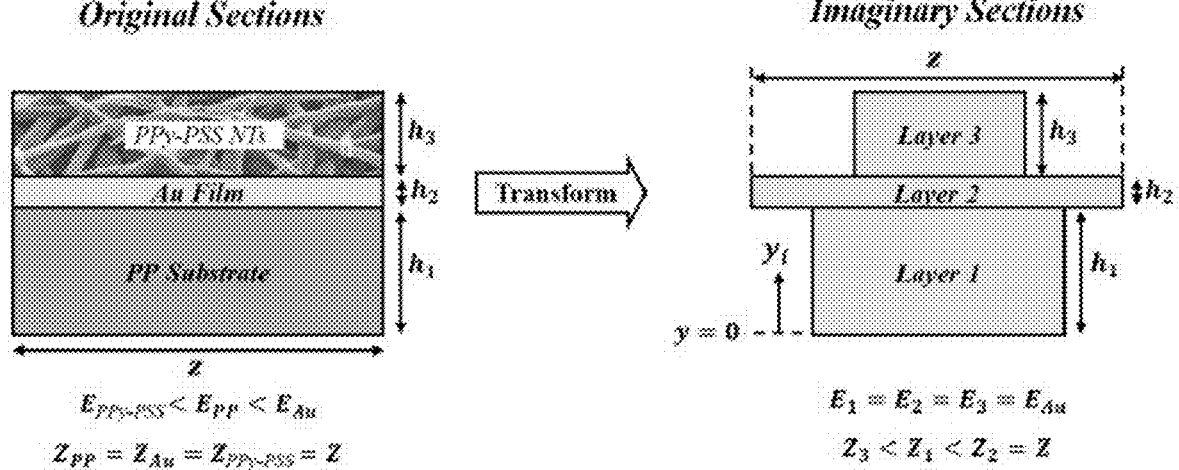

FIG. 11: Schematics illustrate the cross-section of the beam before and after transformation.

Figure 12:
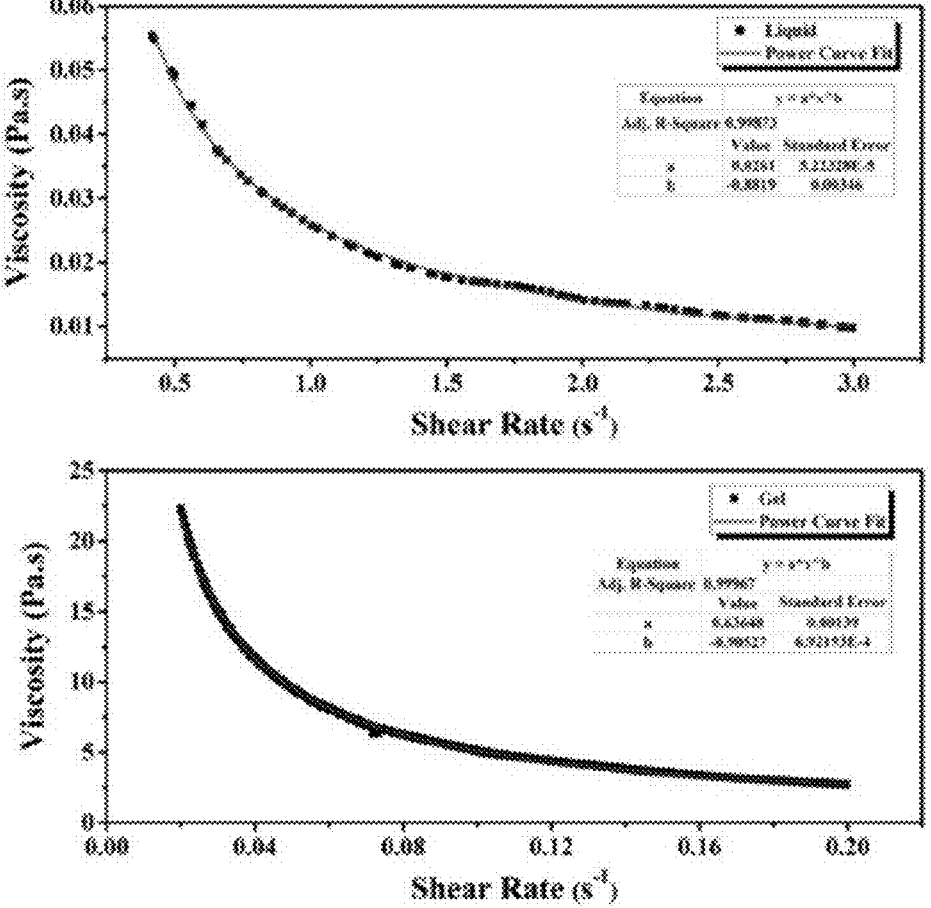

FIG. 12: Apparent viscosity of liquid and gel electrolytes containing 0.1 M NaPSS as a function of shear rate measured by 40 mm parallel plates with a gap of 0.5 mm at room temperature.

Figure 13:
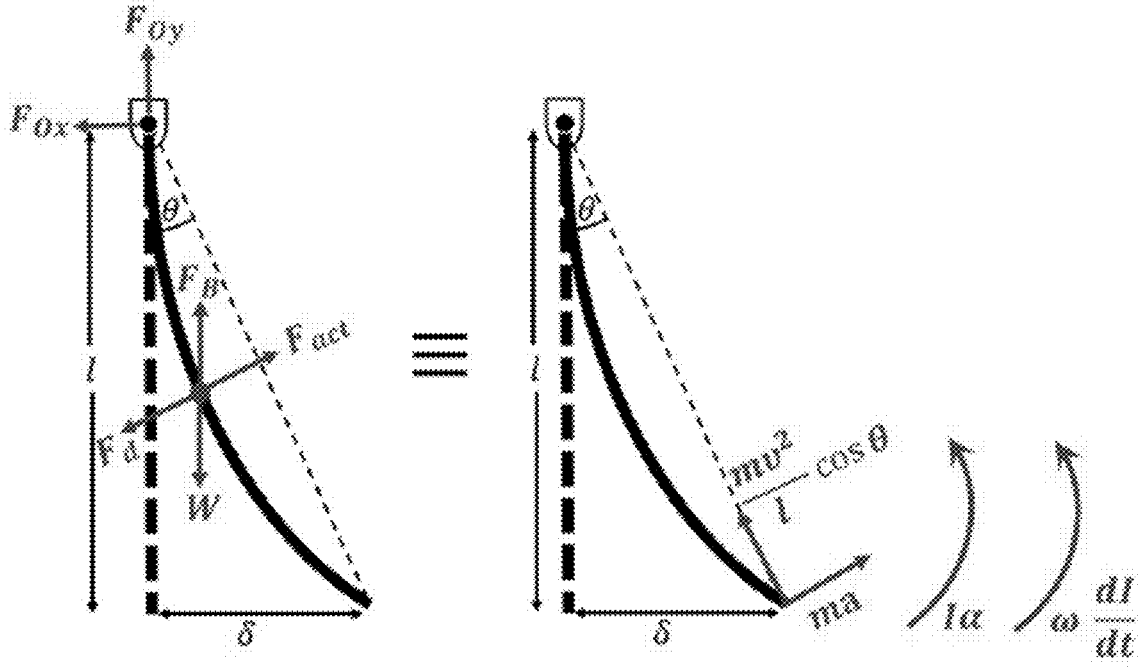

FIG. 13: Free body-diagram and kinetic diagram of the actuator. The forces exert on the actuator, including actuation force (Fact), drag force (Fd), buoyancy force (FB), weight (W), and support forces (Fox and Foy), are indicated on the left-side diagram (i.e., free body diagram). The Kinetic diagram includes the forces related to rate of changes of linear and angular momentums.

FIGS. 14A-14L: Applied linear potential waveforms (FIGS. 14A-B), mass change $\Delta m(t)$ (FIGS. 14C-D), the rate of mass change (dm/dt) (FIGS. 14E-F), tip deflection ($\delta$) (FIGS. 14G-H), tip velocity (v) (FIGS. 14I-J), and tangential acceleration $\alpha(t)$ (FIGS. 14K-L) as a function of time at various scan rates of 10 mV s$^{-1}$ (blue square), 50 mV s$^{-1}$ (green circle), 100 mV s$^{-1}$ (red upward triangle), and 200 mV s$^{-1}$ (black downward triangle) in liquid (FIGS. 14A, 14C, 14E, 14G, 14I) and gel (FIGS. 14B, 14D, 14F, 14H, 14J) electrolytes (all graphs corresponds to the cycle 10th). The curves for the scan rate of 10 mV s$^{-1}$ are presented as inset in each graph.

FIGS. 15A-15F: Applied linear potential waveforms (FIGS. 15A-B), drag force Fd(t) (FIGS. 15C-D), and actuation force (Fact) (FIGS. 15E-F) of the OSNTs actuator as a function of time during CV at various scan rates of 10 mV s$^{-1}$ (blue square), 50 mV s$^{-1}$ (green circle), 100 mV s$^{-1}$ (red upward triangle), and 200 mV s$^{-1}$ (black downward triangle) in liquid (FIGS. 15A, 15C, 15E) and gel (FIGS. 15B, 15D, 15F) (all graphs corresponds to the 10th cycle). The curves for the scan rate of 10 mV s$^{-1}$ are presented as inset in each graph.

Figure 16:
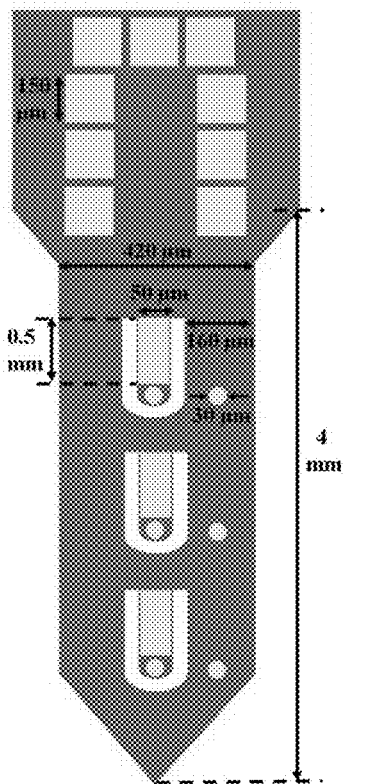
Figure 16:
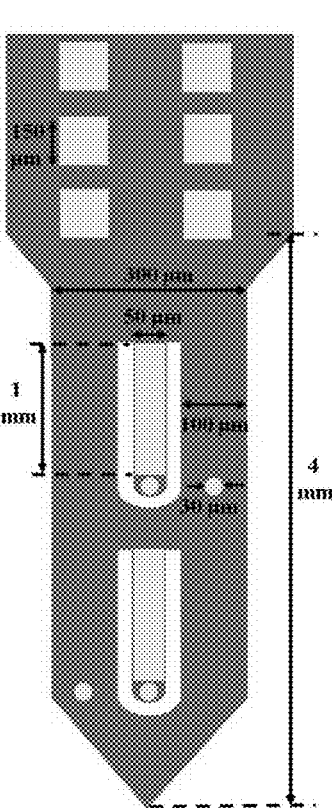

FIG. 16: Schematics represent probe designs with two and three movable projection sites.

Figure 17:
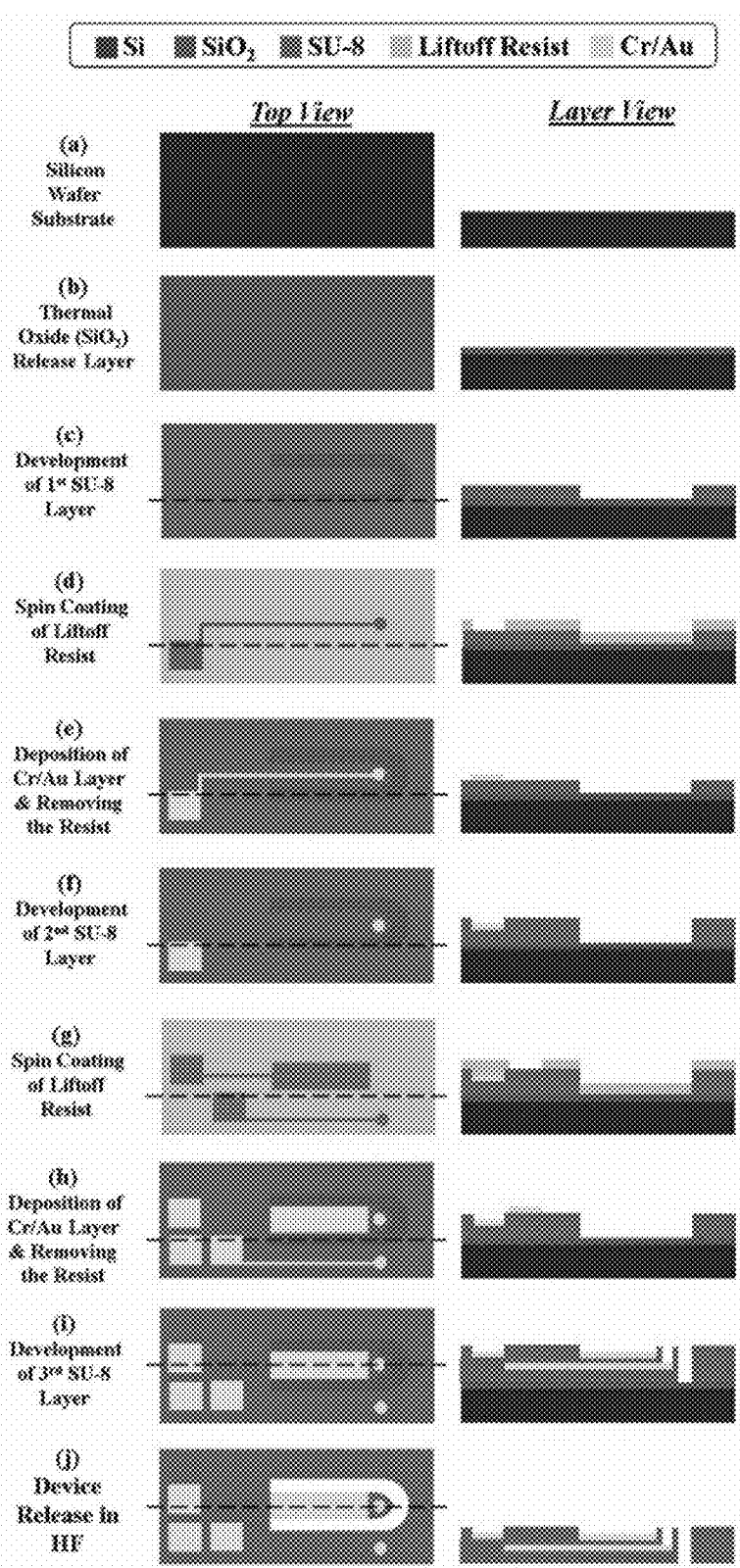

FIG. 17: Overview of the fabrication process of the probe devices.

FIG. 18: Optical micrographs of the fabricated neural probes with two and three projection sites.

FIGS. 19A-19F: Scanning electron micrographs of probe projections coated with an electroactive layer of PPy film (FIGS. 19A-19C) and PPy NFs (FIGS. 19D-19F).

Figures 20A, 20B, 20C:
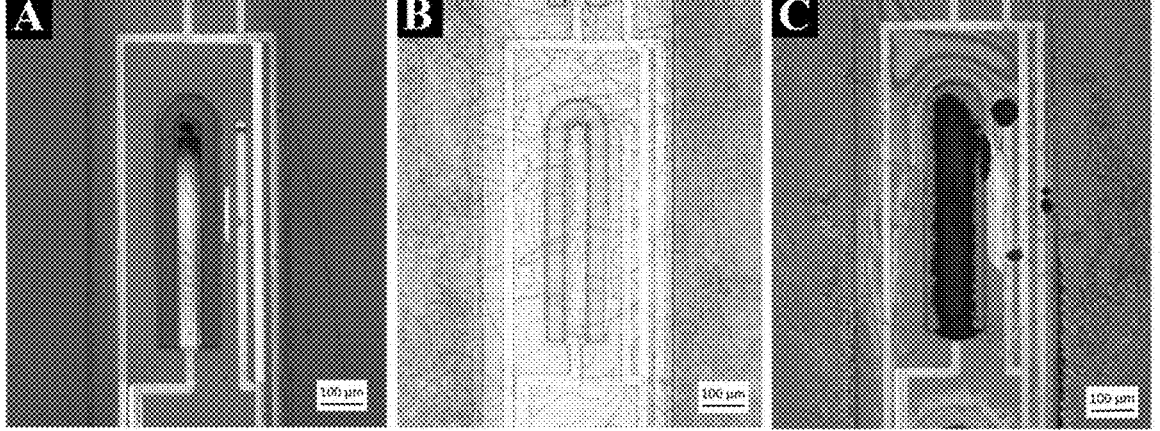

FIGS. 20A-20C: Coating of probe projections with PPy NFs: (FIG. 20A) gold projection, (FIG. 20B) electrospinning of template PLLA NFs on the projection, and (FIG. 20C) electrodeposition of PPy around template PLLA NFs, followed by removing of the uncoated template nanofibers.

FIGS. 21A-21F: Electrochemical impedance, phase angle, and Nyquist (Z'-Z") plots of the probes with two (FIGS. 21A, 21C, 21E) and three (FIGS. 21B, 21D, 21F) projections before (black squares) and after coating with PPy film (red circle) and PPy NFs (blue triangle).

FIGS. 22A-22D: Cyclic voltammograms of the probes projections coated with PPy NFs at various CV scan rates. The black curves belong to probes with two 1 mm projections and the red curves are attributed to the probes with three 0.5 mm projections.

Figure 23:
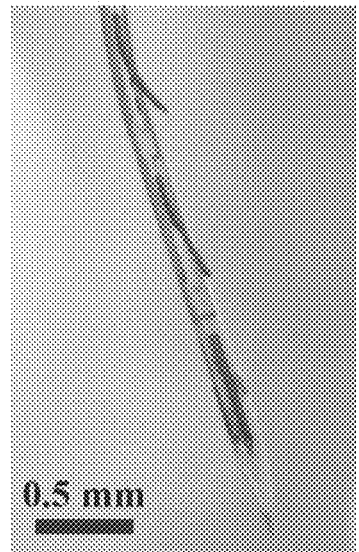

FIG. 23: Bending movement of the probe projections under cyclic voltammetry in aCSF electrolyte.

Figures 24A, 24B:
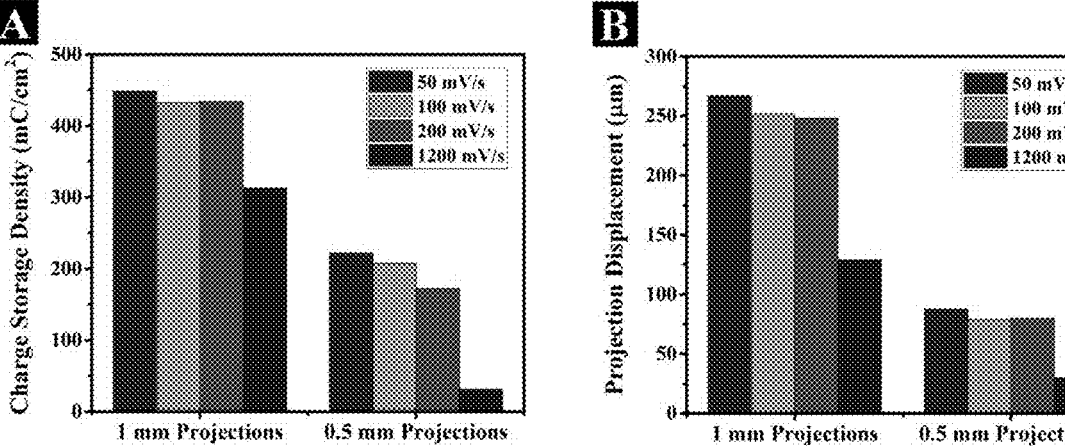
Figures 25A, 25B, 25C, 25D, 25E:
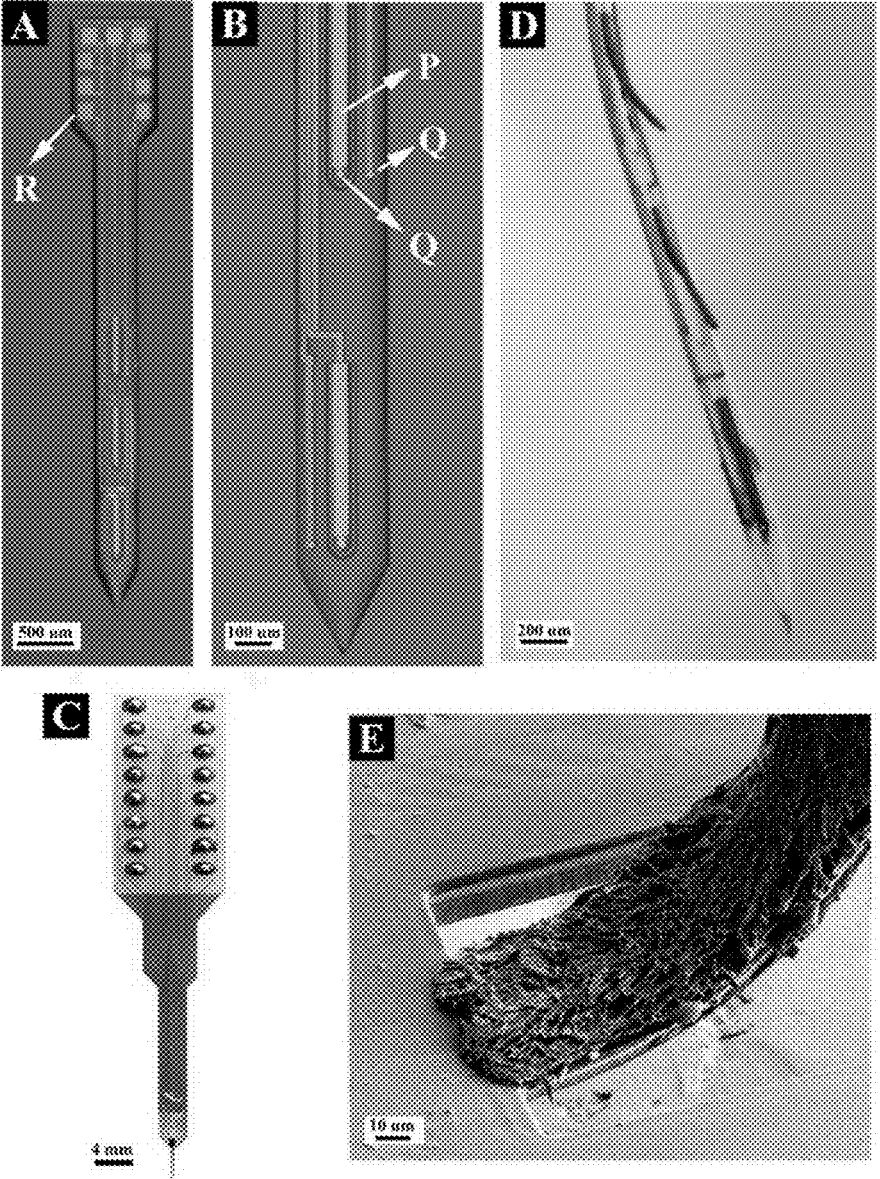

FIGS. 24A-24B: Charge storage density (FIG. 24A) and displacements (FIG. 24B) of actuating projection sites (1 mm and 0.5 mm projections) under various CV scan rates in aCSF electrolyte. The data is obtained from a single probe actuated at various scan rates.

FIGS. 25A-25E: A proof of concept for utilization of OSNTs device for movable neural microprobes. (FIGS. 25A-B) Optical micrographs of the probe with three microcantilevers fabricated using standard photolithography. The probe consisted of three gold-coated microcantilevers (marked by P), six circular electrode sites (marked by Q), and nine connection pads (marked by R). (FIG. 25C) A photograph of the microprobe assembled on a printed board circuit using wire-bonding. (FIG. 25D) Actuation of microcantilevers coated with OSNTs under CV at 200 V s$^{-1}$. Each microcantilever can be individually controlled for a desired range of motion. (FIG. 25E) Scanning electron micrograph of the probe microcantilever coated with OSNTs.

FIGS. 26A-26L: Applied linear potential waveforms (FIGS. 26A-B), mass change Δm(t) (FIGS. 26C-D), the rate of mass change (dm/dt) (FIGS. 26E-F), tip deflection (δ) (FIGS. 26G-H), tip velocity (v) (FIGS. 26I-J), and tangential acceleration α(t) (FIGS. 26K-L) as a function of time at various scan rates of 10 mV s$^{-1}$ (blue square), 50 mV s$^{-1}$ (green circle), 100 mV s$^{-1}$ (red upward triangle), and 200 mV s$^{-1}$ (black downward triangle) in liquid (FIGS. 25A, 25C, 26E, 26G, 26I) and gel (FIGS. 26B, 26D, 26F, 26H, 26J) electrolytes (all graphs corresponds to the cycle $10^{th}$). The curves for the scan rate of 10 mV s$^{-1}$ are presented as inset in each graph.

FIGS. 27A-27F: Long-term assessment of high performance OSNTs Device. (FIG. 27A) Power consumption/strain percentage of the OSNTs actuator, compared with different types of soft electrochemical actuators. (FIG. 27B) Bending stability (δ1 δ0) of the OSNTs actuator over 15000 actuations at 200 mV s$^{-1}$ (25 hours of continuous operation). δ0 corresponds to the actuator deflection at the first cycle, and δ is the deflection at the nth cycle. Inset represents the sample variation in the maximum tip deflection ($\delta_{max}$) within the first 1000 actuations in liquid and gel electrolytes (±SEM, n=3). There is no significant difference in the δmax over the course of actuation in both liquid and gel electrolytes (p>0.05). (FIGS. 27C-D) Scanning electron micrographs of OSNTs before (FIG. 27C) and after (FIG. 27D) actuation at scan rate of 200 mV s$^{-1}$ for 1000 times. (FIGS. 27E-F) Optical microphotographs of the transverse cross-section of the actuator after actuation for 1000 times at scan rate of 200 mV s$^{-1}$.

DESCRIPTION OF ILLUSTRATIVE EMBODIMENTS

Electrochemical devices that transform electrical energy to mechanical energy through an electrochemical process have numerous applications ranging from soft robotics and micropumps to autofocus microlenses and bioelectronics. To date, achievement of large deformation strains and fast response times remains a challenge for electrochemical actuator devices operating in liquid wherein drag forces restrict the actuator motion and electrode materials/structures limit the ion transportation and accumulation. Accordingly, in certain embodiments, the present embodiment provides electrochemical actuators, electrochemical mass transfers, and electrochemical dynamics made from organic semiconductors (OSNTs). In certain aspects, OSNTs electrochemical device exhibits high actuation performance with fast ion transport and accumulation and tunable dynamics in liquid and gel-polymer electrolytes. This device demonstrates an impressive performance, including low power consumption/strain, a large deformation, fast response, and excellent actuation stability. This outstanding performance stems from enormous effective surface area of nanotubular structure that facilitates ion transport and accumulation resulting in high electroactivity and durability. The present studies of motion and mass transport along with the theoretical analysis for a variable-mass system established the dynamics of the electrochemical device and a modified form of Euler-Bernoulli's deflection equation was introduced for the OSNTs. The present electrochemical devices may be utilized in artificial muscles and biomedical devices.

The present OSNTs device exhibits high electrochemical performance in liquid and gel polymer electrolytes. The present OSNTs demonstrate an outstanding performance, including low power consumption/strain (~0.5 mW cm$^{-2}$%-1), large deformation (displacement ~7.88 mm; strain ~3.35%), fast response (speed ~1280 μm/s; times<1 s), and excellent actuation stability (>96.5% after 25 hrs of continuous operation) with tunable dynamics. These high-performance characteristics are ascribed to the enormous surface area of OSNTs associated with large ion exchange (mass flux~167 g cm$^{-3}$), low elastic modulus (average~6.79 MPa), high charge storage density (charge density~448 mC cm$^{-2}$), and large specific capacitance (~170 F g$^{-1}$) of OSNTs. The effective surface area of the present nanotubular structure facilitates charge storage with boosted ions transportation resulting in high electroactivity and durability.

Further provided herein are high-performance electrochemical devices based on the present OSNTs for the production of micro and nano-scale actuators. The present OSNTs may be used in several applications, including movable and implantable interface devices, such as flexible neural microelectrodes. Recent advances in neuroscience have enabled the exploration of brain activity and neural disorders and allowed understanding of its mechanisms down to the microscopic level. Neural recording technologies have remarkably contributed to this understanding by revealing neuron activities and functional connectivity.

Neural interfacing devices have been utilized in various clinical applications including cochlear and retinal implants, spinal and peripheral nerve interfaces, epilepsy monitoring devices, and deep brain stimulators. Accordingly, soft materials are increasingly employed for neural electrodes to provide mechanically compatible interfaces while minimizing trauma to the neural tissue. Many polymers have been explored for development of flexible neural probes, including SU-8, polyimide, parylene, polydimethylsiloxane (PDMS), liquid crystal polymers, cyclic olefin polymers, polymethyl methacrylate, polycarbonate, and polystyrene. Combination of material properties, processing conditions, and performance demands determine selection of a particular polymer for a device. However, implantation and localization of soft electrodes in soft tissues is challenging owing to additional tissue damage caused by rigid auxiliary tools used for implantation, lengthy interface recovery and micromotion of the soft electrode. In addition, the distance between the location pf electrodes and neurons can reduce the quality of recording signals. The dilemma of choosing between facile implantation of rigid probes and compatible interface of soft electrodes has called for the evolution of materials and fabrication techniques for neuronal recording technology. Neuronal recordings using current implantable microelectrode technologies have been found to be inconsistent and/or unreliable in long-term assessments. This limitation is the most significant impediment toward the success of emerging cortical prostheses that rely on their recording stability over the lifetime of patients who use such prosthetic devices. As an alternative to fixed microelectrodes, movable microelectrodes have been suggested as a potential approach to mitigate some of these limitations. Technologies that enable control of microelectrodes after implantation remarkably enhance the ability to (a) isolate activity from single neurons (b) maintain stable neuronal recordings over longer durations (c) maintain the signal-to-noise ratio in the neuronal recordings (d) seek neurons of interest after implantation. Accordingly, this study proposes a novel movable neural microelectrode composed of flexible and biocompatible microcantilevers coated with conjugated polymer nanotubes, which can potentially control the position of its recording sites after implantation in brain tissue.

Accordingly, in certain embodiments, provided herein are flexible neural microelectrodes based on conjugated polymer actuators for the development of movable and implantable neural interface devices for modulating the position of electrode sites within brain tissue or guiding insertion of neural probes along curved trajectories. The actuation of polypyrrole nanofibers/nanotubes (PPy NFs/NTs) doped with polystyrene sulfonate (PSS) may be utilized for articulating flexible neural probes with multiple movable projections employed in the cerebral environment. Bilayer beam projections composed of a structural photoresist (SU-8) layer, chromium and gold (Cr/Au) contact traces, and electroactive layer of PPy NFs/NTs can be electrochemically actuated through cyclic voltammetry in artificial cerebrospinal fluid (aCSF). In the present studies, the electrochemical properties and actuation performance of the projections of varying length coated with PPy NFs/NTs were investigated at various cyclic voltammetry (CV) scan rates in aCSF electrolyte. Additionally, the utilization of the conjugated polymer nanotubes coating on the electrode projections and recording sites improved signal recording, increased the charge capacity for stimulation, and can provide actuation-controlled drug delivery.

I. NON-CONDUCTIVE AND CONDUCTIVE POLYMERS

The "non-conductive polymer" does not conduct electricity or conducts electricity significantly less efficiently than conductive polymers. Without being bound by theory, non conductive polymers lack a conjugated $\pi$-system and thus electrons are not able to be delocalized over an extended number of atoms. Non-limiting examples of non-conductive polymers include polyester polymers, such as poly(lactide), poly(glycolide), poly(lactide-co-glycolide), and polyanhydride polymers such as poly(serbacic acid) or polycaprolactone, or substituted versions thereof. The non-conductive polymer may be applied as a composition containing the non conductive polymer and a quaternary ammonium salt. Non-limiting examples of suitable quaternary ammonium salts include benzyltriethylammonium chloride, tetraethylammonium chloride, tetraethylammonium bromide, tetrabutylammonium hydroxide, and tetrabutylammonium fluoride. When the non-conductive polymer is in a composition, the composition comprises the non-conductive polymer from about 1% w/w to about 25% w/w. In some embodiments, the composition comprises the non-conductive polymer from about 1% w/w, 2% w/w, 3% w/w, 4% w/w, 5% w/w, 6% w/w, 7% w/w, 8% w/w, 9% w/w, 10% w/w, 12% w/w, 14% w/w, 16% w/w, 18% w/w, 20% w/w, to about 25% w/w.

The "conductive polymer" used in the present methods refers to an organic polymer that conducts electricity. Without being bound by theory, conductive polymers comprise an extended $\pi$-system in which adjacent $\pi$-orbitals overlap allowing for the delocalization of electrons across the entirety of the $\pi$-system. The $\pi$-system may comprise alternating double and/or triple bonds, heteroatoms, or a combination thereof. Non-limiting examples of conductive polymers include poly(pyrrole), poly(thiophene), poly(acetylene), polyphenylene, polyphenylene sulfide, poly(aniline), and substituted versions thereof, such as poly(3, 4-ethylenedioxythiophene) (PEDOT).

II. DEPOSITION AND ELECTROCHEMICAL POLYMERIZATION CONDITIONS

Conditions that can be modulated in order to promote, enhance, or accelerate deposition of a non-conductive polymer applied by electrospray include, but are not limited to, temperature, humidity, spinneret gauge, applied field, and flow rate. When a non-conductive polymer or a composition thereof is applied to a conductive surface, the temperature is between about 10° C. to about 50° C. In some embodiments, the temperature is from about 10° C., 15° C., 16° C., 17° C., 18° C., 19° C., 20° C., 21° C., 22° C., 23° C., 24° C., 25° C., 26° C., 27° C., 28° C., 29° C., 30° C., 35° C., 40° C., 45° C., to about 50° C. The humidity is from about 5% to 75%, such as from about 25% to about 40%. In some embodiments, the humidity is from about 5%, 10%, 15%, 20%, 25%, 30%, 35%, 40%, 45%, 50%, 55%, 60%, 65%, 70%, to about 75%. The non-conductive polymer or composition thereof is applied to the conducive surface via a spinneret. The spinneret has a gauge of from about 20 to about 30. In some embodiments, the gauge of the spinneret is 20, 21, 22, 23, 24, 25, 26, 27, 28, 29, or 30. When the non-conductive polymer or a composition thereof is applied to a conductive surface, an electric field may be applied. When such a field is applied, the applied field is from about 0.5 kV/m to about 1000 kV/m, such as from about 50 kV/m to about 200 kV/m, or such as from about 0.5 kV/m to about 10 kV/m. In some embodiments, the applied field is from about 0.5 kV/m, 1 kV/m, 2 kV/m, 3 kV/m, 4 kV/m, 5 kV/m, 6 kV/m, 7 kV/m, 8 kV/m, 9 kV/m, 10 kV/m, 25 kV/m, 50 kV/m, 75 kV/m, 100 kV/m, 125 kV/m, 150 kV/m, 175 kV/m, to about 200 kV/m. When a non-conductive polymer or composition thereof applied to a conductive surface, it is applied with a flow rate from about 100 μL/hr to about 1000 μL/hr. In some embodiments, the flow rate is from about 100 μL/hr, 200 μL/hr, 300 μL/hr, 400 μL/hr, 500 μL/hr, 600 μL/hr, 700 μL/hr, 800 μL/hr, 900 μL/hr, to about 1000 μL/hr.

Conditions that can be modulated in order to promote, enhance, or accelerate electrochemical polymerization include, but are not limited to, monomer concentration, temperature, use and concentration of dopants, configuration and mode of use of an electrical source, and current density applied. When an electrical source is used in the electrochemical polymerization of a monomer to obtain a conductive polymer, the electrical source is used in the galvanostatic mode and the electrical source may used in various configurations. In some embodiments, a two-electrode configuration is used, while in other embodiments, a four-electrode configuration is used. Polymerization of the monomer is achieved at a temperature from about 10° C. to about 50° C. In some embodiments, the temperature is from about 10° C., 15° C., 16° C., 17° C., 18° C., 19° C., 20° C., 21° C., 22° C., 23° C., 24° C., 25° C., 26° C., 27° C., 28° C., 29° C., 30° C., 35° C., 40° C., 45° C., to about 50° C. The concentration of the monomer of the conductive polymer from about 0.05 M to about 2 M. In some embodiments, the concentration of the monomer of the conductive polymer is from about 0.05 M, 0.1 M, 0.2 M, 0.3 M, 0.4 M, 0.5 M, 0.6 M, 0.7 M, 0.8 M, 0.9 M, 1 M, 1.5 M, to about 2 M. The monomer may be polymerized while in solution and the solution may further comprise a dopant. Suitable dopants are negatively charged and non-limiting examples of dopants include perchlorate, dodecylbenzenesulfonate, p-toluene-sulfonate, laminine fragment, fibronectin fragment, a negatively charged nerve growth factor, or poly(styrene-sulfonate). Polymerization of the monomer may further comprise applying a current density from about 0.01 mA/cm² to about 5 mA/cm², such as from about 0.01 mA/cm² to about 5 mA/cm². Polymerization of the monomer may further comprise applying a charge density from about 1 mC/cm² to about 500 mC/cm², such as from about 10 mC/cm² to about 250 mC/cm², or such as from about 25 mC/cm² to about 250 mC/cm².

III. BIOSENSORS AND BIOELECTRONICS

The long-term performance of biosensors and bioelectronics relies on biocompatibility and sensitivity of the electrode-tissue interface. Microdevices prepared according to the methods disclosed herein may be used to in biosensing and/or bioelectronic applications and may enhance biocompatibility, biostability, efficacy, signal to noise ratio, charge-transfer capacity, or abrogate undesirable immune response. Non-limiting examples of biosensors and bioelectronics include neural electrodes. Current neural electrodes are limited by poor electrical performance including high initial impedance and low charge storage capacity. In addition, they are mechanically hard which causes cellular reactive response to the implanted electrode. Neural electrodes comprising conducting polymer microstructures prepared according to the methods disclosed herein offer an alternative and may exhibit higher levels of biocompatibility.

In some embodiments of the present disclosure, devices such as electrodes comprising conducting polymer coated microstructures disclosed herein can be used to provide for electrical stimulating and sensing that can facilitate drug and bioactive substance delivery in a controlled and specific manner. There are numerous configurations of electrode substrates having drug delivery and nanofiltration capabilities presently contemplated by the present disclosure which can be successfully practiced. In various embodiments, the present disclosure can be adapted to create fully integrated and more efficacious implanted electrodes for cortical recording/stimulation, deep brain stimulators, peripheral nerve electrodes, cardiac anti-arrythmia devices, muscle stimulation, surgical ablation (epilepsy treatments), pH monitoring, glucose sensing, cochlear implants, and retinal prosthetics.

Devices comprising conducting polymer coated microdevices described herein can be connected to power supplies which can include a battery, a direct wire to a DC or AC power source, and can further include one or more switches or variable resistors to control the electrical signal inputted to the conducting monomers for electrochemical polymerization and/or for stimulating device to release stored bioactive substances to adjacent or localized target cells or tissues. In various embodiments, the power source can be connected to a counter electrode and/or reference electrode. In some embodiments, while in use, the electrodes can be in contact with a physiological medium such as spinal fluid, blood, neurons, brain, heart and muscle tissue. The devices can also be connected to sophisticated current delivery devices and computers/CPUs, including pulse generators, radio frequency modulators, counters and recorders for electrical output and recording functions. Furthermore, in addition to the advanced biomimetic features of the electrode substrate coated at least with a portion of nanotubes and nanoparticles, the ability to deliver bioactive substances in response to electrical stimulation provides a novel and improved modality in disease treatment and tissue regeneration. Moreover, drug loaded conducting polymer nanotubes and nanoparticles are highly biocompatible, having low electrical impedance, cell-attracting, high surface area, electrically active coating for electrode-based biomedical devices.

The present disclosure provides devices for precisely controlled release of one or more drug for electrically sensing and stimulating biomedical device applications. Targeted delivery by the electrically conducting nanotubes can be performed precisely by releasing individual drugs and bioactive substances at desired points in time using electrical stimulation of conducting polymers. In accordance with the present disclosure, the methods described herein provide a generally useful means for creating low impedance, biologically active polymer coatings which can facilitate integration of electronically active devices with living tissues. Other biomedical applications of the devices contemplated by the present disclosure include: molecule-eluting, electrically active polymer nanotubes facilitating highly localized stimulation of neurite outgrowth and guidance for neural tissue regeneration using neuronal growth and differentiation factors.

In some embodiments, the present disclosure provides for sensing devices having spatially and temporally controlled drug delivery for ablation and pharmacological alteration of specific cell populations. The drug and bioactive substance loaded nanotubes of the present disclosure can also be used for functionalizing microelectrodes on neural prostheses and biosensors. However, the electrically conducting drug delivery devices comprising an electrode substrate, having a network of electrically conductive nanotubes comprising biocompatible non-degradable polymers or nanoparticles loaded with bioactive substances previously coated with conducting, biocompatible, non-degradable polymers can also be expected to be applied in a broad range of fields such as organic chemistry, biomedical engineering, and pharmacology. The improved design represents a new generation of biomaterials that can interact with living tissue including cells within and adjacent to biomedical device implantation sites via signaling mechanisms that have until recently, been the exclusive domain of cells themselves. Practical application of biological sensors comprising conducting polymer as disclosed herein can include glucose detection.

In certain embodiments of the present disclosure, the conducting polymer nanotubes can be directly deposited within living tissue thereby reducing the likelihood of electrode damage and tissue damage during and after electrode implantation. In certain embodiments, the resulting cell-based conducting electrode can be in intimate contact with the plasma membrane of living cells.

IV. DEFINITIONS

The use of the word "a" or "an," when used in conjunction with the term "comprising" in the claims and/or the specification may mean "one," but it is also consistent with the meaning of "one or more," "at least one," and "one or more than one."

Throughout this application, the term "around" when used in conjunction with the location of the polymerization means that the polymer is deposited on at least one side of the target object. In a preferred embodiment, the polymer is deposited on at least three sides.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to affect such treatment or prevention of the disease.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

V. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Organic Semiconductor Nanotubes for Electrochemical Devices

A high-performance electrochemical device made of OS nanotubes (OSNTs) was designed and developed. The performance of OSNTs device was assessed within two distinct electrolytes, liquid and polymer-gel, to demonstrate the applications in aqueous-based environments with different range of viscosities. The OSNTs device exhibited low power consumption/strain ($\sim 0.5$ mW cm-2%-1), large deformation (displacement$\sim 7.88$ mm; strain$\sim 3.35\%$), fast response (speed$\sim 1280$ $\mu$m/s; time$<1$ s), and excellent actuation stability ($>96.5\%$ after 25 hrs of continuous operation). These high-performance characteristics were ascribed to the enormous surface area of OSNTs associated with large ion exchange (mass flux$\sim 167$ g cm-3), low elastic modulus (average$\sim 6.79$ MPa), high charge storage density (charge density$\sim 448$ mC cm-2), and large specific capacitance ($\sim 170$ F g-1) of OSNTs.

Figures 1A, 1B, 1C, 1D, 1E, 1F, 1G:
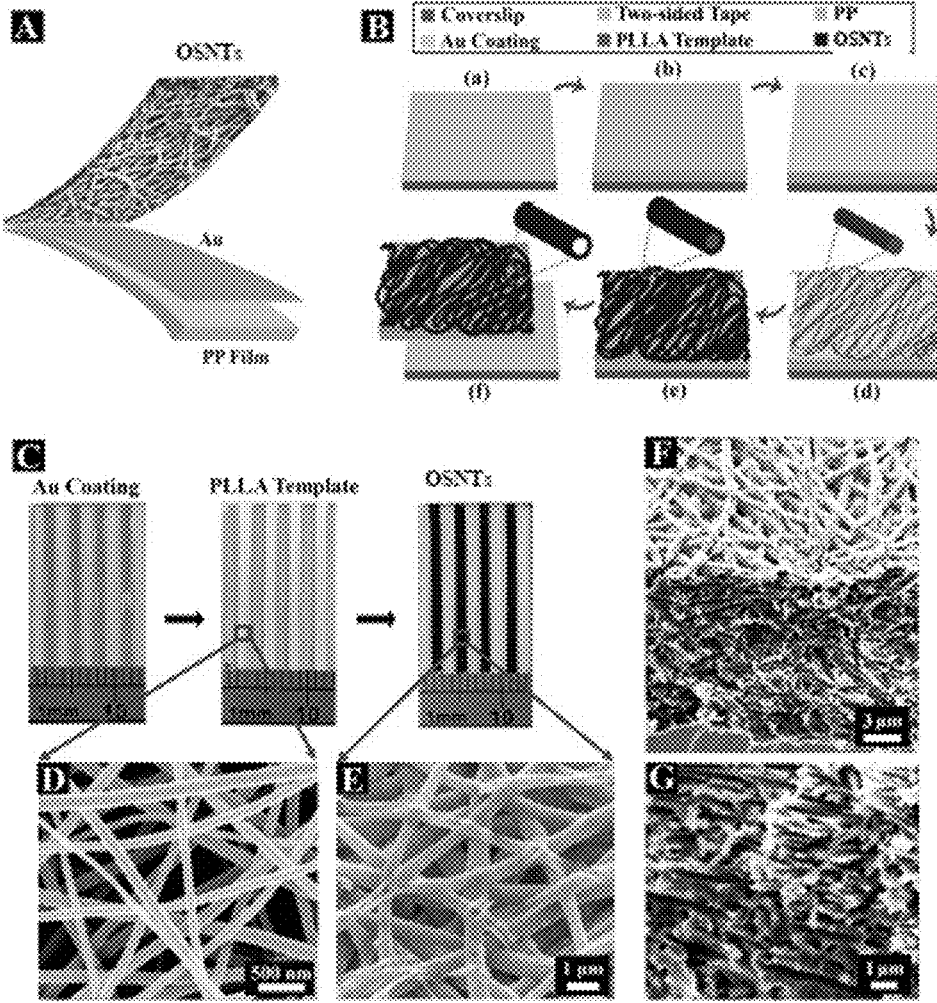
FIGS. 1A-1G: Fabrication and characterization of OSNTs device.

To fabricate the OSNTs device, an electroactive layer of organic semiconductor polypyrrole doped with polystyrene sulfonate (PSS) was electrodeposited around template poly-L-lactide (PLLA) nanofibers that were previously electrospun onto a thin layer of gold (Au) coated on a structural layer of flexible polypropylene (PP), followed by removal of PLLA nanofiber templates (FIGS. 1A-C). PSS, a large anionic dopant, was embedded into OS structure during electropolymerization to neutralize the positive charges of oxidized OS chains. Given that large counterions are immobile within the OS matrix, during redox reaction only cations/hydrated cations (here Na+) are exchanged between OS and electrolyte, resulting in significant enhancement of output strain and bending deformation of actuator in comparison with small counterions such as ClO4$^-$.[15a] The average diameter of PLLA nanofibers and the resultant OSNTs (FIGS. 1D-E) were 140±4 nm and 626±16 nm, respectively (size distribution histograms are given in FIG. 5). PLLA is a biodegradable material with extremely slow degradation rate that can be processed into electrospun fibers, which remain stable during electrochemical deposition.[11a] Cross-sectional scanning electron micrographs of the OSNTs layer confirmed the presence of widespread pores and nanotubular structure of OS, which presumably facilitate charge storage with boosted ions transportation (FIGS. 1F-G). The OSNTs were subjected to cyclic voltammetry (CV) in aqueous solution and 0.2 wt. % agarose hydrogel both containing 0.1 M poly(sodium 4-styrenesulfonate) (NaPSS) (FIG. 6). Low concentration gel polymer electrolytes with high ionic conductivity have been previously utilized for energy storage,[17] air working electrochemical actuators,[18] and biomedical applications.[19] Agarose hydrogel is optically transparent and allows for transportation of cations and/or solvated cations between the electrolyte and the actuator during CV cycling. The CV potential sweep was carried out within a range of −0.8 to +0.4 V at various scan rates of 10, 50, 100, and 200 mV s-1. CV was used to investigate the electroactivity of OSNTs actuator over a range of voltage and also conduct reversible electro-mechanical stimulation at various voltage scan rates.

Figures 2A, 2B, 2C, 2D, 2E, 2F, 2G, 2H, 2I:
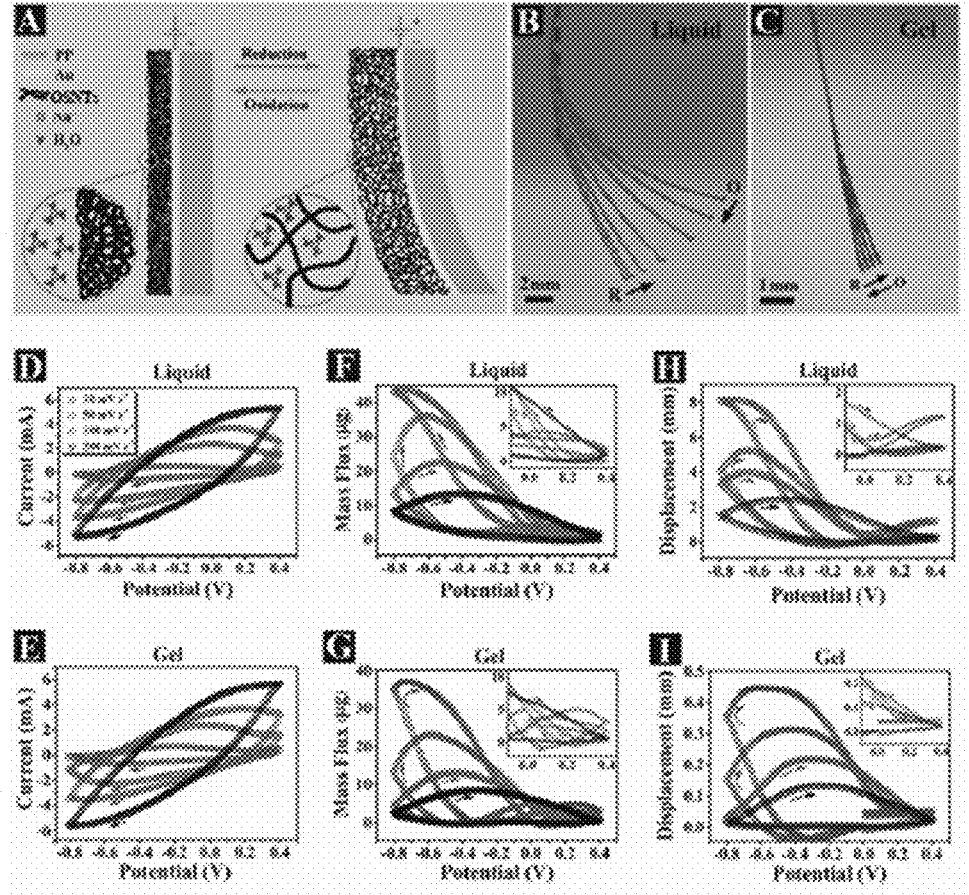
FIGS. 2A-2I: Electrochemical actuation of OSNTs device using cyclic voltammetry.

The bending displacement of the actuator under CV cycling was investigated in both liquid and gel electrolytes (FIGS. 2A-C). The actuator showed fully reversible bending deformation under consecutive reduction-oxidation (redox) reactions in each cycle. The primary mechanism for bending deformation is the volume change of OSNTs due to the insertion and ejection of ions and solvent molecules into/out of the polymer matrix (FIG. 2A). When ions and solvent enter the OSNTs, the polymer expands, and when they exit the OSNTs, the polymer contracts according to the following reaction:

$$OSNTs^{N+}(PSS^-)n+n(Na^+)+n(e^-)+m(S)=OSNTs^3$$
$$(PSS^-)n(Na^-)n(S)m$$

where n represents the number of electrons (el, m represents the number of solvent molecules (S), OSNTsn+ is the oxidized state and OSNTs0 represents the neutral state. OSNTs0(PSS⁻)n indicates that anion PSS is entrapped into OSNTs as a dopant during electro-polymerization, and OSNTs0(PSS⁻)n (Na+)n(S)m indicates that Na+ cations and solvent molecules are inserted as the OSNTs is reduced. [20] According to Equation 1, when the OSNTs are reduced, cations (here Na+) and solvent molecules (here water) migrate from the electrolyte to the polymer to compensate the net charge and, resulting in swelling of the nanotubes. In contrast, when the OSNTs are oxidized, Na+ cations and water molecules migrate from the polymer to the electrolyte, leading to shrinkage of the nanotubes.[12b] The in-plane actuation strain generated upon reduction and oxidation of the OSNTs is converted into a bending deformation due to the strain mismatch between the active OSNTs and the passive underneath layers at the interface.

FIGS. 2D-I depict the induced current, mass flux (influx/efflux), and tip displacement of the OSNTs actuator measured under a CV cycle at various scan rates of 10, 50, 100, and 200 mV s-1 in both liquid electrolyte (FIGS. 2D, 2F, 2H) and gel electrolyte (FIGS. 2E, 2G, 2I). During the initial forward scan (i.e., potential swept from 0 to −0.8 V), reduction of the OSNTs resulted in a steep increase in mass influx of cations into the OSNTs and in actuator displacement (counter clockwise) (FIG. 7) as the potential swept to the cathodic peak potential, followed by a gradual increment in both mass flux and displacement curves. Interestingly, during the reverse scan (i.e., potential swept from −0.8 to +0.4 V), the mass flux and displacement further increased to their maximum values where the cathodic current reached zero at potentials −0.64, −0.61, −0.54, and −0.46 V in liquid electrolyte and −0.64, −0.59, −0.54, and −0.43 V in gel electrolyte at the scan rates of 10, 50, 100, and 200 mV s-1, respectively. As the anodic current increased (i.e., OSNTs were oxidized), both mass flux and displacement values gradually decreased due to the efflux of Na+ cations with clockwise deflection of the actuator. Subsequently, steep decreases were observed in the mass flux and displacement curves as the potential swept to the anodic peak potential. These decreases continued till all cations were expelled from OSNTs and actuator returned to its original position as depicted in inset FIGS. 2F-I. Furthermore, by increasing the potential, the mass flux slightly increased and the actuator deflected counter-clockwise (i.e., displacement increased) (FIG. 7) likely due to solvent transport into the OSNTs as an attempt to balance the osmotic pressure in the system.[21] As the scan rate decreased, the time-dependent diffusion of water molecules led to a more significant increase in the mass flux and the resulting displacement (insets in FIGS. 2F-I). Finally, during the second step of forward scan (i.e., potential swept from +0.4 V to 0 V), as OSNTs were still oxidized, the actuator mass flux and displacement remained unchanged or slightly decreased. These results demonstrate that the actuator displacement can be precisely controlled by adjusting the applied voltage and scan rate. Such precision control of actuator displacement is an advantage in soft robotics and artificial muscles.

Figures 3A, 3B, 3C, 3D, 3E, 3F, 3G, 3H, 3I, 3J, 3K:
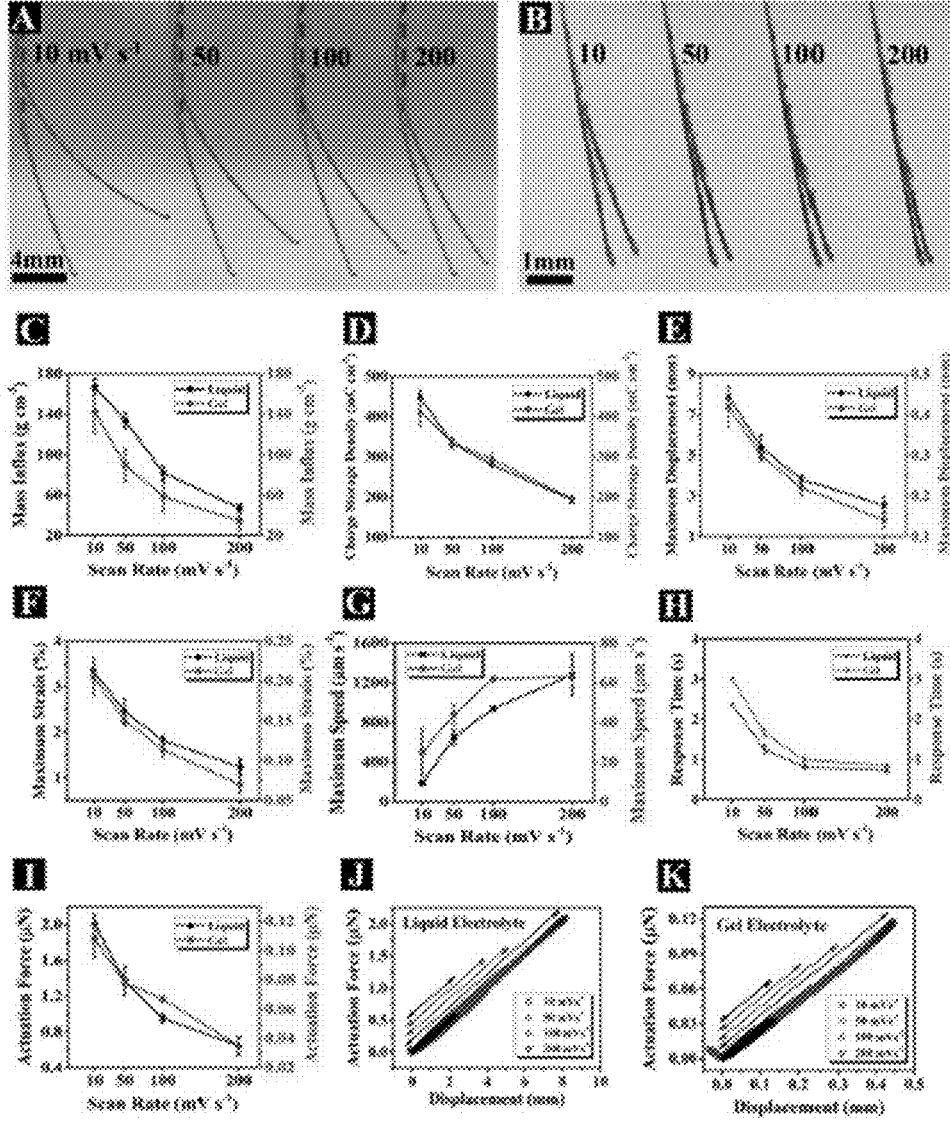
FIGS. 3A-3K: Electro-chemo-mechanical response of OSNTs device at various CV scan rates.

Next, the electro-chemo-mechanical response of the OSNTs device was characterized at various CV scan rates 10, 50, 100, and 200 mV s⁻¹ in liquid and gel electrolytes (FIG. 3). Remarkably, the device exhibited the largest mass flux (~167 g/cm³), charge storage density (~448 mC cm⁻²), specific capacitance (~170 F g⁻¹), maximum displacement (~7.88 mm), and maximum strain (~3.35) at a scan rate of 10 mV s-1 in liquid electrolyte. In fact, the high surface area to volume ratio along with high electrical conductivity and electrochemical activity of OSNTs provide smooth pathways for adequate ion transport and accumulation. The energy storage performance (i.e., charge storage density and specific capacitance) of the present actuator exceeds those of reported OS based electrochemical actuators.[22] An increase in scan rate requires faster ion transport in the solvent and quicker intercalation and deintercalation of ions into/out of OSNTs respectively. However, due to restricted mobility of ions in an electrolyte under the influence of an electric field,[23] at higher scan rates fewer ions migrate into/out of polymer. Thus, the mass flux significantly declined (p<0.01) from 166.81±8.12 to 47.08±4.15 g cm⁻³ in the liquid electrolyte and from 142.38±20.54 to 34.38±9.27 g cm⁻³ in the gel electrolyte when scan rate was increased from 10 to 200 mV s⁻¹ (FIG. 3C). It is noteworthy that the charge storage density (FIG. 3D) and specific capacitance (FIG. 9) significantly decreased from 447.9±17 to 193.15±9.05 mC cm⁻² and from 169.7±6.7 to 73.2±3.4 F g⁻¹, respectively in the liquid electrolyte and from 410.15±33.95 to 195.45±6.25 mC cm⁻² and from 155.4±12.9 to 74.0±2.4 F g⁻¹, respectively in the gel electrolyte (p<0.01). In addition, there was no statistically significant difference between the charge storage density and specific capacitance of the actuator in liquid and gel electrolytes at same scan rates, suggesting that OSNT actuators maintain the same electroactivity in both gel and liquid electrolytes. Remarkably, the actuator generates a large maximum strain of 3.35% and a maximum displacement of 7.88 mm in liquid electrolyte at scan rate 10 mV s⁻¹ (FIGS. 3E-F). More importantly, at scan rate 200 mV s⁻¹ the actuator can generate a strain (1.24%) that is greater compared with those reported previously. [7, 22a, 22b, 24] Notably, maximum displacement (FIG. 3E) and actuation strain (FIG. 3F) decreased with increasing scan rate, presumably due to insufficient time for ion transport into/out of polymer at higher scan rates, as discussed earlier. The smaller displacement observed in the gel electrolyte compared to liquid can be attributed to the greater resistive forces exerted on the actuator by the surrounding viscoelastic gel, compared to aqueous solution.

To investigate the electrochemical dynamics of the device its speed, response time, and generated actuation force were assessed. The instantaneous velocity of the actuator tip was calculated from the rate of changes of the tip displacement (FIG. 14). As shown in FIG. 3G, the maximum speed of actuator increased with increasing the scan rate. In liquid electrolyte, the actuator exhibited a high maximum speed of $190 \pm 10$ $\mu$m s$^{-1}$ at scan rate 10 mV s$^{-1}$ and impressively a higher maximum speed of $1280 \pm 210$ $\mu$m s$^{-1}$ at scan rate 200 mV s$^{-1}$. Notably, the actuator demonstrated faster response (<1 s) at higher scan rates of 100 and 200 mV s$^{-1}$ (FIG. 3H), that are substantially improved compared with those observed in other OS-based electrochemical actuators (e.g., OS film with response time of 5 s and maximum speed of ~1000 $\mu$m s$^{-1}$).[25] In addition to offering a high maximum speed and a fast response time, this actuator was able to produce a large maximum force. It is worth nothing that the fast and large deformation is attributed to the extensive surface area of OSNTs, facilitating quick ion motion and accumulation.

The generated actuation force ($F_{act}$) was calculated by the moment equation of motion for a rigid body with variable mass that is submerged in a liquid. In fact, this equation relates the moment of forces acting on the actuator to angular momentum, (FIG. 12, 13)

$$F_{act} = \frac{1}{6}[[m_0 + \Delta m]a + \dot{m}v]\left[4 + \frac{h^2}{l^2}\right] +$$
$$\frac{1}{2}C_d lb\rho v(t)^2 + [[m_0 + \Delta m]g - \rho hlbg] \sin\left[\frac{\delta}{l}\right]$$

where m0 is initial mass of actuator (~1360 $\mu$g), $\Delta$m is mass change, m=dm/dt is rate of mass change (FIG. 14), $\delta$ is deflection, v is velocity (FIG. 14), $\alpha$ is acceleration, h is actuator thickness (~43.3 $\mu$m), b is actuator width (1 mm), l is actuator length (20 mm), Cd is drag coefficient, p is electrolyte density (~1 g mm$^{-3}$), and g is gravitational acceleration constant (9.81 m s$^{-2}$). Prior modeling studies on bilayer CP actuators [12a, 26] operating in an electrolyte solution were based on the classical beam theory [27] for metal bimorphs that bend upon heating due to difference in thermal expansion coefficients (Timoshenko's model),[28] whereas the normal force and bending moment at any cross section of the beam are zero. However, these models did not dynamically evaluate the actuator movement and did not consider the effect of fluid forces exerted on the actuator to determine the generated actuation force (i.e., blocking force). In contrast, the dynamic model, the moment equation of motion for a rigid body with variable mass that is submerged in a liquid, is more realistic and accurate as it considers the motion of the actuator under action of forces in a fluid. The actuator generated a force of $0.65 \pm 0.10$ $\mu$N in liquid electrolyte at the scan rate 200 mV s$^{-1}$. Impressively, the actuation force increased to $2.00 \pm 0.12$ $\mu$N as the scan rate decreased to 10 mV s$^{-1}$. Similarly, the generated actuation force had a substantial increase in gel electrolyte with decreasing the scan rate (FIGS. 3I, 15).

The correlation between the generated actuation force and the resultant deflection at various scan rates in liquid and gel electrolytes are plotted in FIGS. 3J-K. As shown, the actuator exhibited a reversible linear relation between actuation force ($F_{act}$) and deflection ($\delta$). Interestingly, there was no significant difference between the slope of the plots in liquid and gel electrolytes at all scan rates (p>0.05). Furthermore, the deflection of OSNTs actuator was investigated according to Euler-Bernoulli's composite beam theory [28]. Such a linear relationship for a cantilever beam can be described by a modified form of deflection equation as given in the below equation.

$$\delta = (\gamma l^3 /(EI)_{eff})F_{act}$$

where $\gamma$ is a constant, l is actuator length, and $(EI)_{eff}$ is the effective flexural rigidity of the composite beam that can be obtained using transformed sections method (FIG. 10, 11, Table 1). Using this approach, a value of $\gamma \approx 7.35$ was obtained for the deflection equation, interestingly, in both liquid and gel electrolytes and statistical analysis revealed no significant difference (p>0.05) between $\gamma$ values obtained from deflection at various CV scan rates in liquid and gel electrolytes (Table 2).

Figures 4A, 4B, 4C, 4D, 4E, 4F:
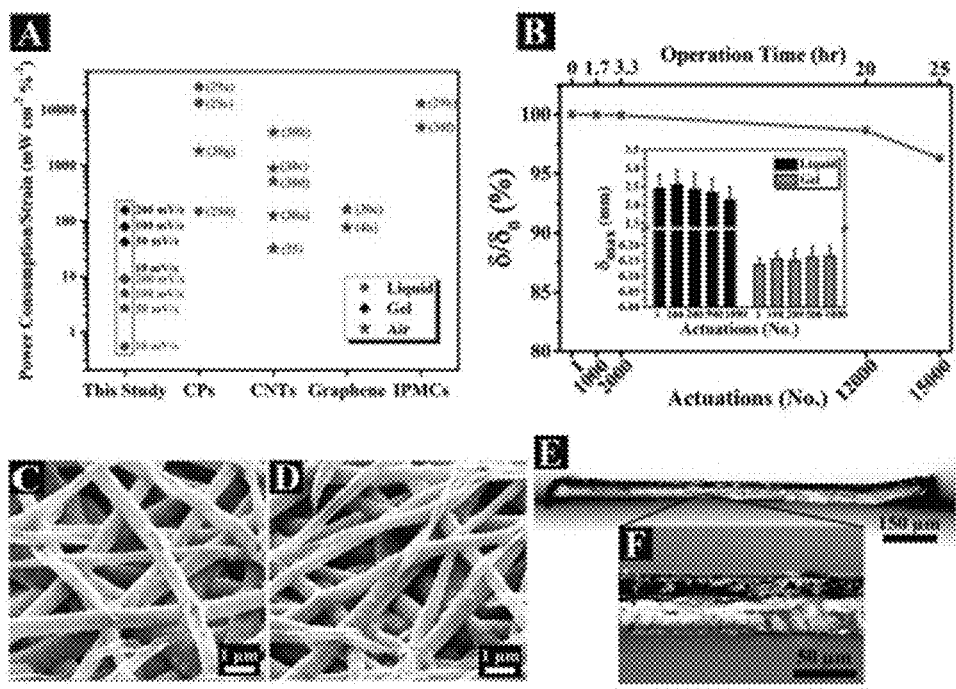
FIGS. 4A-4F: Long-term assessment of high performance OSNTs Device.

Considering that the actuation strain in the electrochemical actuator depends on the electro mechanical efficiency, the power consumption per generated strain is a particularly relevant metric to evaluate the actuation's performance. FIG. 4A illustrates the power consumption/strain of the OSNTs actuator at various CV scan rates in liquid and gel electrolytes. As shown, the power consumption/strain of the OSNTs actuator is within the ranges of 0.5-9.1 mW cm$^{-2}$%$^{-1}$ in liquid electrolyte, and 9-159 mW cm$^{-2}$%$^{-1}$ in gel electrolyte. The low power consumption/strain values for the OSNTs actuator operating in liquid electrolyte mark a profound improvement compared with previously reported electrochemical actuators operating in liquid [29] and air [4b, 24, 30] (FIG. 4A). Notably, the OSNTs actuator yielded relatively low power consumption to strain in the gel electrolyte, which is comparable with air operating actuators and much less than those operating in liquid electrolyte. Such low power consumption/strain vastly raises their utility in various applications where power consumption/strain is desired to be minimal with maximal yield and actuation power.

Further, the long-term stability (i.e., mechanical durability) of the OSNTs device over a great number of actuations was evaluated (FIG. 4B). Remarkably, the OSNTs device showed a bending stability >96.5% in liquid electrolyte over 15,000 actuations (25 hours of continuous operation) at scan rate 200 mV s$^{-1}$ (equivalent to cycling frequency 0.08 Hz). While electron micrographs (FIGS. 4C-D) and optical micrographs (FIGS. 4E-F) did not indicate any obvious mechanical damage or delamination of OSNTs over the course of actuation, the slight degradation in actuator displacement (~3.5%) may be attributed to the nanoscale deformation and stress relaxation in OSNTs. These results suggest that the OSNTs actuator can effectively operate in liquid and gel electrolytes and can mechanically endure a large number of actuations. In fact, this OSNTs actuator exhibited superior long-term stability compared with previously reported CP-based actuators operating in liquid electrolyte (e.g., CP film [31] with substantial bending degradation after 11 hr). [31-32]

In summary, this study presents a novel and versatile method for design and development of electrochemical device, with OSNTs as the main constituent, capable of operating in liquid and gel polymer electrolytes. The device exhibits excellent electrochemical characteristics including, low power consumption/strain, large deformation, fast ion transport/accumulation, tunable dynamics, and excellent actuation stability. This high performance is attributed to the enormous surface area of OSNTs associated with large ion exchange and accumulation, low elastic modulus, high charge storage density, and large specific capacitance. The experimental studies of motion and mass transport along with theoretical analysis of a body system with variable mass were utilized to establish the dynamics of the actuator and to introduce a modified form of Euler-Bernoulli's deflection equation for the OSNTs actuator. Various types of chemically derived and functionalized organic semiconductors can be formulated to further enhance electro-chemical-mechanical properties of this device, exceeding the electrochemical performance. Considering these achievements along with versatile application of OSNTs and OSNFs, [11a, 13d, 13e, 16] the OSNTs—based electrochemical device may be utilized for advancement of next generation actuators in the fields of soft robotics, artificial muscles, bioelectronics, and biomedical devices.

Example 2—Materials and Methods

Materials: Poly(L-lactide) (PLLA, Resomer 210) with the inherent viscosity of 3.3-4.3 dL $g^{-1}$ was purchased from Evonik Industries. Benzyl triethylammonium chloride and pyrrole (Py) (Mw=67.09 g mol-1) were purchased from Fisher Scientific. Poly(sodium-p-styrene sulfonate) (NaPSS, Mw=70 kD) and chloroform were purchased from Acros-Organics. Agarose powder (Agarose ITM, Gel strength≥1200 g $cm^{-1}$) was purchased from VWR Life Science. 6 MHz Au/TiO2 quartz crystal wrap-around electrodes were purchased from Metrohm, USA. Biaxially-oriented poly(propylene) (PP) films were obtained from backing layer of Scotch removable double-sided tape (3MTM).

Fabrication of Nanoscale Fiber Templates: A homogeneous solution of PLLA (3 wt. %) in chloroform was prepared by adding 230 mg PLLA in 5 ml chloroform and stirring the mixture overnight at room temperature. To enhance the solution charge strength, 23 mg Benzyl triethylammonium chloride (an organic salt) was added to the solution prior to stirring. PLLA nanofibers were directly electrospun onto Au-coated substrates using a syringe pump with the spinneret gauge of 23. The electrospinning process was carried out in an electric field of 0.91 kV $cm^{-1}$ with a flow rate of 50 μL $hr^{-1}$, and a syringe-substrate distance of 11 cm for 6 min. Temperature and humidity were kept constant at 26° C. and 30%, respectively. For the bilayer beam actuator, the passive layer was a PP film (30 μm thick, 1 mm wide, and 20 mm long) coated with a thin gold layer (~0.3 μm, FIG. 8) using a desktop sputtering system (Denton Desk II) at 40 mA for 8 min. For electrochemical quartz crystal microbalance (EQCM) measurements, PLLA nanofibers were electrospun on Au-coated quartz crystals (diameter ~6.7 mm) for 1 min using the same process parameters.

Electrochemical Deposition of Organic semiconductor: 0.2 M electrolyte solution was prepared by dissolving 277 μL Py monomer and 824 mg NaPSS in 20 ml deionized water. Prior to electrodeposition, samples were kept in the electrolyte solution for 30 min to ensure that the solution has completely diffused into the fiber interspaces. Then, the electrodeposition was carried out at the current density of 0.5 mA $cm^{-2}$ for 2 hrs. To fabricate OSNTs, PPy was electropolymerized around template PLLA nanofibers, and then the template PLLA was dissolved in chloroform to create OSNTs. The electrochemical deposition was performed using an Autolab PGSTAT 128N (Metrohm, USA) in galvanostatic mode with a two-electrode configuration at room temperature. For EQCM samples, electrodeposition was performed for 15 min using an Autolab EQCM kit in which a gold wire served as the counter electrode. For bilayer beam actuator, samples were connected to the working electrode and a platinum (Pt) foil served as the counter electrode.

Beam Actuation using Cyclic Voltammetry (CV): Actuation of the bilayer beam actuator was performed using Autolab PGSTAT 128 in a three-electrode configuration with a saturated Ag/AgCl reference electrode and a 1 cm×2 cm Pt foil as counter electrode (FIG. 6). The CV was performed within the potential range of −0.8 to +0.4 V at various scan rates of 10, 50, 100, and 200 mV $s^{-1}$. The actuation behavior of the constructed bilayer beam was assessed in aqueous and agarose hydrogel (0.2 wt. %) electrolytes containing 0.1 M NaPSS. To prepare the aqueous electrolyte, 824 mg NaPSS was dissolved in 40 ml de-ionized water at room temperature. For gel preparation, 80 mg agarose powder was added into 40 ml NaPSS solution (0.1 M), and the slurry was heated in a microwave oven for 1 min to dissolve agarose in the NaPSS solution. The agarose solution was then cooled down in refrigerator at 4° C. for 15 min. Prior to actuation, all samples were primed in the NaPSS solution at the scan rate of 100 mV s-1 for 10 cycles.

Electrochemical Quartz Crystal Microbalance (EQCM) Measurements: The EQCM measurement was carried out using Autolab PGSTAT 128N equipped with EQCM kit in a three-electrode configuration with a saturated Ag/AgCl reference electrode and a gold counter electrode. The mass measurements of OSNTs under CV was characterized in the liquid and gel electrolytes containing 0.1 M NaPSS. The OSNTs were cycled in the potential range of −0.8 to +0.4 V (versus the Ag/AgCl reference electrode) for 20 cycles, at different scan rates of 10, 50, 100, and 200 mV $s^{-1}$ at room temperature. Prior to the measurements, a stable ion concentration within the OS structure was ensured by subjecting the samples to 5 CV cycles at the scan rate of 10 mV $s^{-1}$. The mass change was calculated using Sauerbrey's equation which correlates the frequency variation ($\Delta f$) in quartz crystal oscillation to the change in mass ($\Delta m$):

$$\Delta F = -Cf \Delta m$$

where Cf is a sensitivity factor that depends on the resonant frequency and operating temperature of the quartz crystal. The value of Cf was 0.0815 Hz $ng^{-1}$ $cm^{-1}$ for this 6 MHz quartz crystal at 20° C. Compared to the actuator, a thinner layer of OSNTs (1.44 μm) was used for EQCM measurements to avoid viscoelastic effects. The mass change of the actuator was estimated by multiplying the EQCM values by the volume ratio of OS layer on the actuator and the EQCM sample (Volume ratio≅5).

Actuator Tip Kinematic Measurements: The bending deflection of the actuator was recorded using a digital camera (Dino-Lite) with 30 frames per second. The recorded videos were then processed using an open-source software (Tracker 5.0.6) to track the actuator tip deflection upon actuation. The response time (tR) at the maximum tip deflections was calculated by subtraction of the time that actuator positioned at the maximum deflection from the time that stimulus cathodic current reached zero.

Mechanical Characterization of the Actuator: Elastic modulus of the actuator components (i.e., OS film, Au layer, and OSNTs in both reduced and oxidized states) were obtained by atomic force microscopy (AFM) in fluid in either contact mode and/or peak force mode as appropriate and indicated below. Force-indentation curves were obtained on a Bruker BioScope Resolve (Bruker nanoSurfaces, CA) AFM employing a ScanAssyst-Fluid+ cantilever (Bruker NanoSurfaces, CA) with a pyramidal tip (qualified tip radius~3.26 nm), nominal spring constant of 0.7 N m-1 assuming sample Poisson's ratio as 0.5. Prior to experimental samples, cantilever was calibrated on a silicon wafer in fluid. Force curves were obtained in contact mode (n=7 to 10 locations, 4 force curves per location) and analyzed using the Sneddon model. Elastic moduli were estimated using a custom MATLAB code.

Rheological Characterization of Liquid and gel electrolytes: The viscosity of 0.1 M NaPSS solution and 0.2 wt. % agarose gel containing 0.1 M NaPSS was characterized using an AR2000ex rheometer (TA instruments) at room temperature. Viscosity measurement was carried out within the shear rate of 10-3-10 s$^{-1}$ using a 40 mm parallel plate with a gap of 0.5 mm.

Structural Characterization of the Actuator: The surface morphology of PLLA nanofibers and OSNTs were characterized using Field Emission Scanning Electron Microscopy (FESEM, FEI 235). Samples were mounted on aluminum stubs by carbon tape and a carbon paint was used for grounding. Prior to microscopy, non-conducive PLLA sample was sputter-coated with a thin gold layer using Denton Sputter Coater for 45 s at 40 mA. Thickness of actuator layers including gold and OSNTs were measured using materials confocal microscopy (LSM800 Zeiss, Germany). For higher precision, the gold and OSNTs were constructed on a polished Si wafer using the same processing parameters. Thickness profiles and 3D surface topography of OSNTs layer (FIG. 8) were generated through a z-stack experiment followed by step height analysis using Confomap software (Zeiss, Germany).

Statistical Analysis: The statistical significance of difference of data was performed by one-way ANOVA and post hoc test (Tukey's test) to analyze significances between sample groups (Origin Pro, Northampton, MA). In this paper, all data are presented as mean±standard error, unless otherwise noted.

Figure 5:
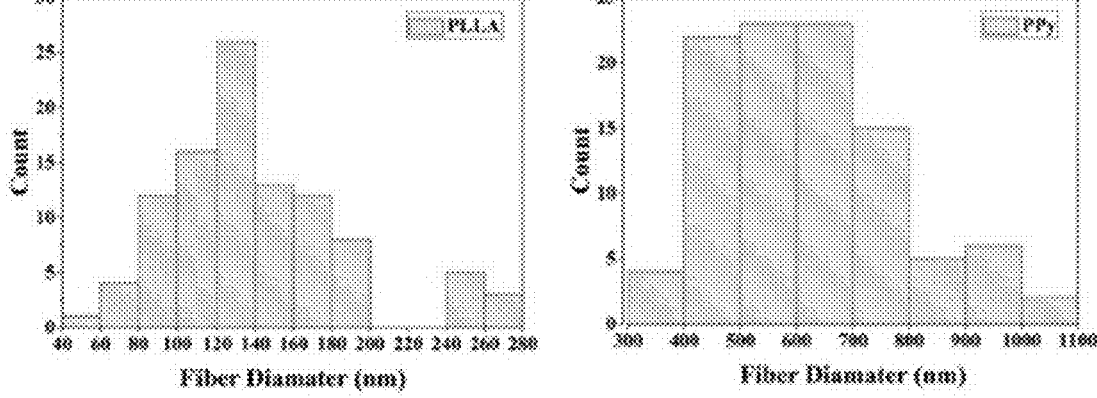
FIG. 5: Histograms demonstrate the diameter of PLLA nanofibers and OSNTs obtained from 100 measurements.

Characterization of Fiber Dimensions: Scanning electron micrographs of the PLLA nanofibers and OSNTs were used for fiber size measurements. The diameter of template PLLA nanofibers and OSNTs were measured using ImageJ software. Histograms of the diameter of fibers were generated after 100 measurements (n=100) (FIG. 5). The calculated diameter of PLLA nanofibers and OSNTs were 140±4 nm and 626±16 nm, respectively.

Electrode Configurations for Electrochemical Experiment: As shown in FIG. 6, the actuation experiment was performed using a three-electrode configuration in a transparent rectangular cell. The actuator deflection was monitored and recorded using a digital camera during cyclic voltammetry (CV). The actuator movement upon reduction and oxidation processes is depicted as a schematic in FIG. 7.

Thickness Measurement of the Device Layers: The thickness of the sputtered gold (Au) and the constructed OSNTs layer were measured using Zeiss Materials Confocal Microscope (FIG. 8). The height profiles were generated using Ziess Confomap software. The Au and OSNTs layers were constructed on a polished silicon (Si) wafer using the same processing parameters as the beam actuator. In fact, the use of a flat surface of Si wafer rather than the rough polypropylene (PP) substrate provided more precise thickness profiles, especially for the Au thin film. As shown in FIG. 8, the mean thickness of the Au and OSNTs layers constructed on the beam actuator were 309 nm and 12.8 μm, respectively. Also, the mean thickness of 1.44 μm was obtained for the OSNTs constructed on the QCM crystals for mass flux measurements.

Calculation of Charge Storage Density and Specific Capacitance: The charge storage density (Q) and specific capacitance (CSP) of the OSNTs were calculated using following equations:

$$Q = \frac{1}{vA}\int_{V_1}^{V_2} i\,dV$$

$$C_{sp} = \frac{1}{\Delta V vm}\int_{V_1}^{V_2} i\,dV$$

where vv is CV san rate, AA is surface area (20 mm×1 mm), m is the mass of the OSNTs layer (~440 μg), and $\Delta V$ is the potential window ($\Delta V$=1.2 V).

Elastic Modulus of the Device Components: Elastic modulus of the device components, including polypropylene (PP) film, Au coating, and OSNTs, were obtained by atomic force microscopy (AFM) in fluid in either contact mode and/or peak force mode (FIG. 10). For all force-indentation curves obtained, contact point was determined as described previously.[1] Contact point was also verified randomly using the conventional manual method. Elastic moduli were only considered if curve fitting was greater than 98%, i.e., r2≥0.98. As expected, the Au had the greatest elastic moduli at 20.55±6.14 GPa followed by PP film with 5.95±2.09 GPa. The ratio of moduli between oxidized OS (11.86±6.85 MPa) and reduced OS (1.73±0.49 MPa) was approximately 6.85:1. The obtained elastic moduli are summarized in Table 1. The order of magnitude of obtained elastic moduli are in the range of those reported in the literature measured by alternative methods. [2-4]

TABLE 1

| Elastic modulus of the actuator components measured by AFM | |
| --- | --- |
| Component | Elastic Modulus |
| Au coating | 20.55 ± 6.14 GPa |
| Polypropylene (PP) film | 5.95 ± 2.09 GPa |
| OS in reduced state | 1.73 ± 0.49 MPa |
| OS in oxidized state | 11.86 ± 6.85 MPa |

Calculation of Effective Modulus of The Composite Material: The effective elastic modulus of the multilayer beam was determined by method of transformed sections, which converts a multilayer beam into a transformed beam composed of only one material (FIG. 11). According to this method, the transformation factor ($n_{ij}$) equals to the ratio of the elastic modulus of transferred layer (i) respect to the reference layer (j) as given below:

$$n_{ij} = \frac{E_i}{E_j}$$

$$n_{12} = \frac{E_1}{E_2} = \frac{E_{PP}}{E_{Au}}$$

-continued $$n_{32} = \frac{E_3}{E_2} = \frac{E_{NTs}}{E_{Au}}$$

where $n_{12}$ is the transformation factor of PP layer, $n_{32}$ is the transformation factor of OSNTs layer, $E_{PP}$ is the elastic modulus of PP, $EN_{Ts}$ is the elastic modulus of OSNTs, and $E_{AU}$ is the elastic modulus of Au.

The location of centroid you of transformed composite beam to Au can be calculated from the below equation.

$$\bar{y}'_{Au} = \frac{\sum_{i=1}^{3} y_i A_i}{\sum_{i=1}^{3} A_i} =$$

$$\frac{n_{12}h_{PP}\left(\frac{h_{PP}}{2}\right) + h_{Au}\left(h_{PP} + \frac{H_{Au}}{2}\right) + n_{32}h_{NTs}\left(h_{PP} + h_{Au} + \frac{h_{NTs}}{2}\right)}{n_{12}h_{PP} + h_{Au} + n_{32}h_{NTs}} =$$

$$\frac{h_{PP}\left(\frac{E_{PP}}{E_{Au}}\right)\left(\frac{h_{PP}}{2}\right) + h_{Au}\left(h_{PP} + \frac{h_{Au}}{2}\right)}{h_{PP}\left(\frac{E_{PP}}{E_{Au}}\right) + h_{Au} + h_{NTs}\left(\frac{E_{NTs}}{E_{Au}}\right)}$$
$$\frac{h_{NTs}\left(\frac{E_{NTs}}{E_{Au}}\right)\left(h_{PP} + h_{Au} + \frac{h_{NTs}}{2}\right)}{}$$

where yi is the centroid of surface area Ai, hPP is the thickness of PP, $h_{NTs}$ is the thickness of OSNTs, and $h_{AU}$ is the thickness of Au, EP is the elastic modulus of PP, $E_{NTS}$ is the elastic modulus of OSNTs ($E_{NTS}$(reduction), $E_{NTS}$(oxidation)), and EAU is the elastic modulus of Au. The area moment of inertia of composite beam relative to neutral axis can be calculated using parallel-axis theorem. The area moment of inertia of a composite beam (I fly) relative to centroid is sum of the area moments of inertia of all layers with respect to a specified reference plane.

$$I'_y = \sum_{i=1}^{3}\left(I_{y_i} + A_i r_i^2\right); r_i = y_i - \bar{y}$$

where Iyi is the area moment of inertia of layer i relative to its centroid plane (yi), Ai is the transformed cross-section area of layer i, and $\bar{y}$ is the centroid of composite beam (neutral axis). Therefore, the area of moment of inertia of transformed beam to Au ($I'_{AU}$) can be obtained from the below equation.

$$I'_{Au} =$$

$$b\left(\frac{1}{12}\left(\frac{E_{PP}}{E_{Au}}\right)h_{PP}^3 + \left(\frac{E_{PP}}{E_{Au}}\right)h_{PP}\left(\frac{E_{PP}}{2} - \bar{y}'_{Au}\right)^2 + \frac{1}{12}h_{Au}^3 + h_{Au}\left(h_{PP} + \frac{h_{Au}}{2} - \bar{y}'_{Au}\right)^2\right.$$
$$\left. + \frac{1}{12}\left(\frac{E_{NTs}}{E_{Au}}\right)h_{NTs}^3 + \left(\frac{E_{NTs}}{E_{Au}}\right)h_{NTs}\left(h_{PP} + h_{Au} + \frac{h_{NTs}}{2} - \bar{y}'_{Au}\right)^2\right)$$

where b is the width of actuator, $h_{PP}$ is the thickness of PP, $h_{NTs}$ is the thickness of OSNTs, $h_{AU}$ is the thickness of Au, $E_{PP}$ is the elastic modulus of PP, $E_{NTs}$ is the elastic modulus of OSNTs ($E_{NTs}$(reduction), $E_{NTs}$(oxidation)), $E_{AU}$ is the elastic modulus of Au, and $\bar{y}AU$ is the location of centroid (neutral axis) of transformed composite beam to Au. Ultimately, the effective flexural rigidity of the composite beam $(EI)_{eff}$ can be obtained using the following equation.

$$(EI)_{eff} = E_{AU} \cdot I'_{AU}$$

By substitution of the known values ($h_{PP}$=30 µm, $h_{AU}$=309 nm, $h_{NTs}$=12.8 µm, b=1 mm, $E_{PP}$=5.95 GPa, $E_{AU}$=20.55 GPa, $E_{Red\ Tubes}$=1.73 MPa, $E_{Ox\ Tubes}$=11.86 MPa), the (EI) eff of 14828 µN mm$^2$ and 14884 µN mm$^2$ was obtained for the composite actuator in the reduced and oxidized states, respectively.

Viscosity Measurement of The Liquid and Gel Electrolytes: The apparent viscosity of the aqueous electrolyte and agarose hydrogel electrolyte containing 0.1 M NaPSS as a function of shear rate is presented in FIG. 12. The measured viscosity values were used for calculation of the drag coefficient. The equivalent velocity is obtained by multiplying the shear rate by the gap between the two plates, i.e., 0.5 mm. Here, the shear rate range for viscosity measurement was chosen according to the equivalent share rate of actuator velocity in liquid and gel electrolytes at various scan rates. As shown in FIG. 12, both liquid and gel electrolytes display a decreasing viscosity by increasing shear rate (shear-thinning), which is a typical behavior of non-Newtonian fluids.

Calculation of Actuation Strain: The actuation strain was calculated from the beam curvature using an equation previously developed for PPy-PSS bilayer microactutores as follows. [5]

$$k = \frac{\varepsilon}{h_{sub}} \frac{6mn(1+m)}{1 + 4mn + 6m^2n + 4m^3n + m^4n^2}; k = \frac{2\delta}{\delta^2 + L^2}$$

where is actuation strain, k is beam curvature, 8 is beam deflection, L is the actuator length (20 mm), hsub is the substrate thickness (30.3 µm), m is the thickness ratio (hPPy–PSS/hsub; where hPPy–PSS=12.8 µm), and n is the elastic modulus ratio (EPPy–PSS/Esub). An effective Esub of 6.38 GPa was determined using the method of transformed sections as described earlier.

Calculation of Actuation Force: The actuation force (Fact) generates during reduction and oxidation of OSNTs can be calculated by the moment equation about the contact end (point O in FIG. 13) of the actuator as generally expressed in the below equations.

$$\sum M_O = \dot{H}_O$$

$$\dot{H} = \frac{d}{dt}(I\omega) = \dot{I}\omega + I\dot{\omega}$$

where $\Sigma$ MO is sum of the moments exert on the actuator about its contact point O (about the axis perpendicular to the plane of motion), HO is the rate of change of angular momentum about the contact point O, I is the mass moment of inertia, I' is the rate of change of the mass moment of inertia, $\omega\omega$ is the angular velocity, and $\omega\omega$ is the angular acceleration of actuator. The forces exert on the center of mass of actuator are indicated in the free body diagram depicted in Figure S9. In this figure, Fact is the actuation force; F is the drag force, which is opposed to the vv vector; W and FB respectively are the weight and buoyancy forces. Accordingly, the above equations can be combined and extended as given in the below equation.

$$\left[F_{act}(t) - F_d(t) + [F_B - W]\sin\left[\frac{s(t)}{l}\right]\right] \times \frac{l}{2} =$$

27

-continued $$\omega \frac{d}{dt}\left[I_G(t) + m(t)d^2\right] + \left[I_G(t) + m(t)d^2\right]\alpha(t)$$

here, $F_{act}(t)$ and $F_d(t)$ respectively are the actuation and drag forces; $\delta(t)$ is the actuator tip deflection; l is the actuator length, m(t) is the actuator mass; IG(t) is the mass moment of inertia of the actuator about its center of mass (IG(t)=(m (t)/12)[$l^2$+$h^2$]), h is the total actuator thickness); d is the distance between the center of mass and the contact point (d=2l/2); $\omega$(t) is the angular velocity ($\omega$(t)=(v(t))/l, where v(t) is the linear velocity); and $\alpha$(t) is the angular accelera-tion ($\alpha$(t)=($\alpha$(t))/l, where $\alpha$(t) is the tangential acceleration). Now, by solving the below equation for $F_{act}$(t):

$$F_{act}(t) = \frac{1}{6}[m(t)a(t) + \dot{m}(t)v(t)]\left[\left(4 + \frac{h^2}{l^2}\right)\right] + F_d(t) + [W - F_B]\sin\left[\frac{\delta(t)}{l}\right]$$

where $\dot{m}$(t) is the rate of mass change, and other variables are the same as defined earlier. It should be noted that (t)=0+ $\Delta$m(t); where m0 is the dry mass of actuator before immer-sion in the electrolyte (m0=1359.33±71.39 µg), and $\Delta$m(t) attributes to the mass change during actuation.

The weight (W) and buoyancy (FB) forces are obtained using following equations:

$$W = m(t)g$$

$$F_B = \rho V g$$

where, m(t) is the actuator mass, g is gravity constant, $\rho$ is fluid density (for both liquid and gel electrolytes $\rho$~1000 Kgm-3), and V is the volume of actuator submerged in the fluid (V=hlb; l actuator length, b actuator width, and h actuator thickness). The fluid drag force imposed on the actuator, i.e., Fd(t), is calculated using Bernoulli's equation as displayed below.

$$F_d(t) = \frac{1}{2}C_d A \rho v(t)^2$$

where Cd is the drag coefficient, A is the frontal area of actuator (A=20 mm×1 mm), $\rho$ is the fluid density, and v(t) is the velocity of actuator relative to fluid. Generally, the drag coefficient is a function the object shape and Reynold's number (Re) of the flow around the moving object. The Reynold's number for a perpendicular flow past a flat plate is defined as given in following equation.

$$Re = \frac{\rho v(t) D_e}{\mu}$$

where $\rho$ is fluid density, v(t) is the actuator velocity relative to fluid, DDeeis the characteristic length of actuator (De=20 mm), and µ is fluid viscosity. Here, the obtained Re number for the flow in both liquid and gel electrolytes was Re<1, which implies that the flow around the actuator is a laminar flow. Tomatika and Aoi theoretically reported the Cd for flat plates moving perpendicular to flow at low Re numbers in a viscous fluid (laminar flow).[6] They reported this Cd as a logarithmic function of Re number as given below.

$$C_d = -10.16\ln(Re) + 10.441$$

28

Knowing the velocity (v(t)) of actuator in the liquid and gel electrolytes, we can obtain the Re number and its corre-sponding Cd value at each time point. Then, by substitution of the obtained Cdv alue, the $F_d$(t) imposed on the actuator in liquid and gel electrolytes is obtained. Finally, using the measured values of $\Delta$m(t), $\dot{m}$(t), $\delta$(t), v(t), $\alpha$(t) and also the calculated value of Fd(t), the $F_{act}$ (t) at each time point can be determined.

Figures 14A, 14B, 14C, 14D, 14E, 14F:
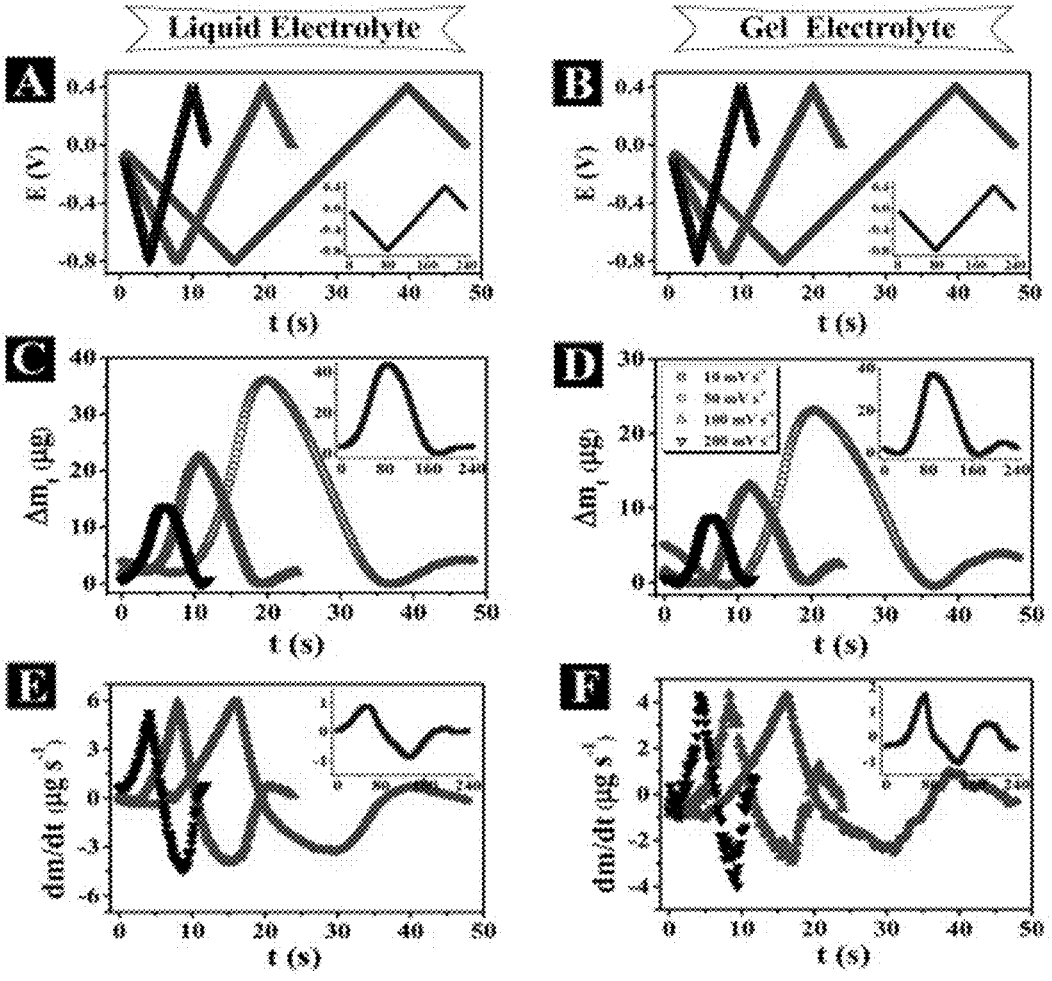

Dynamic Measurements: The dynamics (kinematics, and kinetics) of the OSNTs actuator were studies with variable mass to relate the action of forces on the actuator to their resulting motion under linear potential waveform (CV) between −0.8 V and +0.4 V at various scan rates (10 mV s$^{-1}$ to 200 mV s$^{-1}$) (FIG. 14). The mass change ($\Delta$m(t)) and the rate of mass change ($\dot{m}$(t)=dm/dt) of the OSNTs during CV in liquid and gel electrolytes are depicted in FIGS. 14C-F. It is noteworthy that the sign of rate of mass change indicates the direction of ion migration at the electrolyte-OS interface (FIGS. 14E-F); when the OS is reduced (negative voltage) cations migrate from the electrolyte into the polymer and thus, the rate of mass change is positive; when the OS is oxidized (positive voltage) cations migrate from the polymer to the electrolyte and the rate of mass change is negative.

Figures 14G, 14H, 14I, 14J, 14K, 14L:
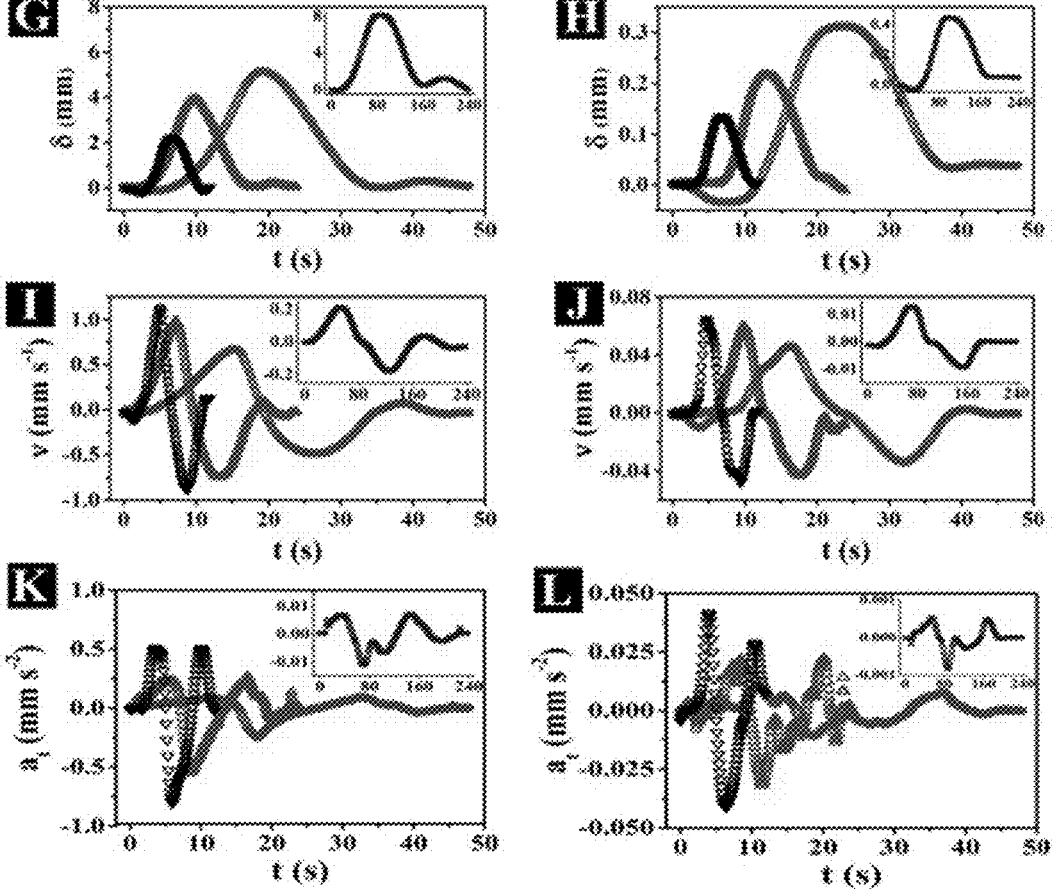
Figures 15A, 15B, 15C, 15D, 15E, 15F:
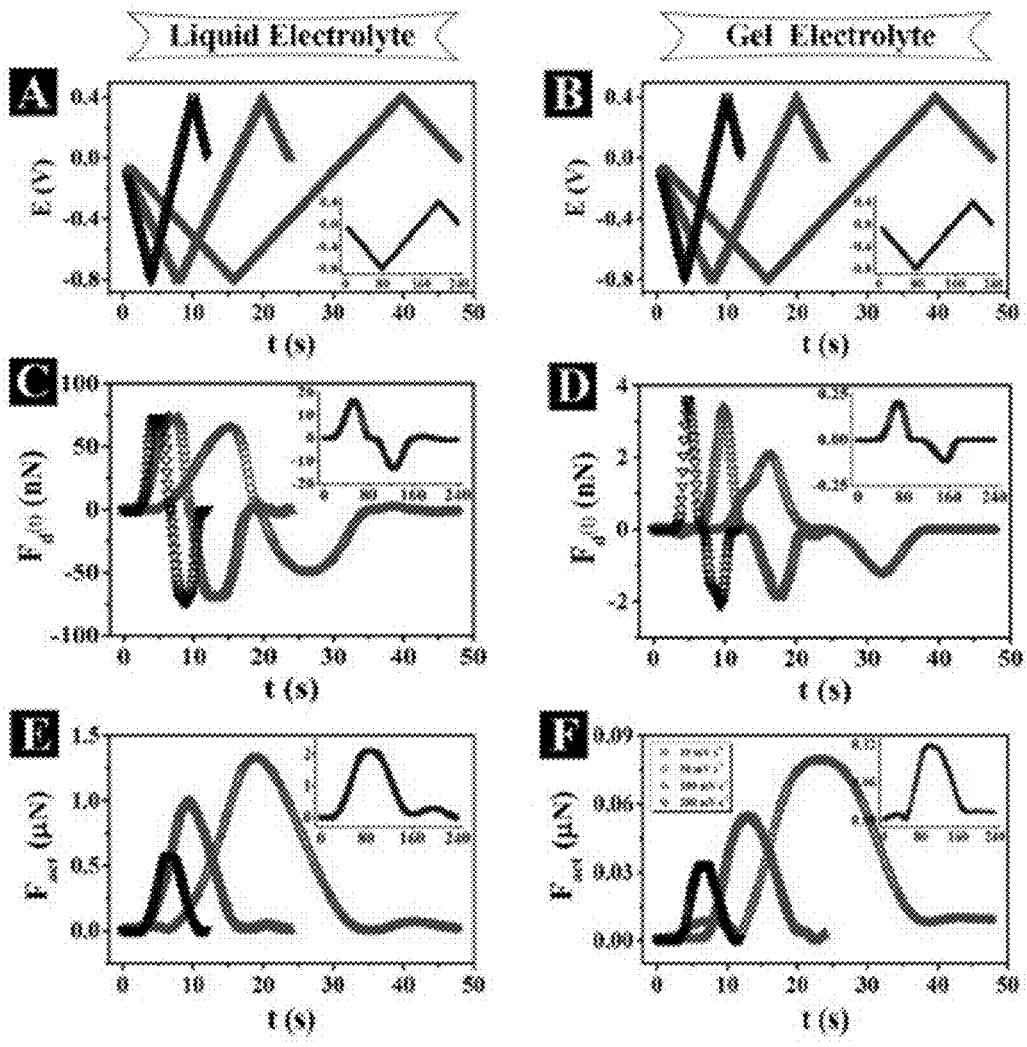

The actuator kinematics including tip deflection $\delta$(t), tip velocity v(t), and tip acceleration ($\alpha$(t)) as a function of time during CV at various scan rates in both liquid and gel electrolytes are demonstrated in FIGS. 14G-14L. FIGS. 14G-14H show a reversible nonlinear deflection and a variable response time during linear potential sweep (CV) upon influx and efflux of cations/hydrated cations. As cat-ions/hydrated cations entered the OSNTs (reduction pro-cess), the $\delta$(t) had a steep increase to the inflection point, followed by a gradual increase to the $\delta$max. Inversely, as the OSNTs were oxidized and cations/hydrated cations left the polymer, the $\delta$(t) gradually decreased to the inflection point and then steeply dropped to the initial position. While the $\delta$max substantially decreased with increasing scan rate (from 7.88±0.49 mm to 2.53±0.4 mm in the liquid electro-lyte, and from 0.42±0.05 mm to 0.14±0.02 mm in the gel electrolyte, as the scan rate respectively increased from 10 to 200 mV s-1, p<0.01); the speed of actuator significantly escalated (p<0.01) with the scan rate increments (FIGS. 14I-J). In particular, in the liquid electrolyte, the absolute value of the maximum and minimum velocities (|vmax| and |vmin|) at the inflection points significantly increased from 0.19±0.01 mm s-1 and 0.15±0.01 mm s$^{-1}$ for 10 mV s$^{-1}$ scan rate to 1.28±0.21 mm s$^{-1}$ and 0.96±0.16 mm s-1 for 200 mV s$^{-1}$ scan rate (p<0.01). In the gel electrolyte, the absolute value of the velocities |vmax| and |vmin| at the inflection points remarkably increased from 0.025±0.012 mm s$^{-1}$ and 0.016±0.008 mm s$^{-1}$ for 10 mV s$^{-1}$ scan rate to 0.063±0.005 mm s$^{-1}$ and 0.052±0.004 mm s$^{-1}$ for 200 mV s$^{-1}$ scan rate, respectively (p<0.01). The actuator dynamics including the calculated drag force (Fd(t)) and actuation force (Fact(t)) under CV cycling at various scan rates in liquid and gel electrolytes are presented as a function of time in FIG. 15.

The correlation between the generated actuation force and the resultant deflection in a CV cycle at various scan rates in liquid and gel electrolytes are plotted in FIGS. 3J-3K in the main text. As observed, the actuator exhibited a reversible linear relation between actuation force $F_{act}$(t) and deflection $\delta$(t). Interestingly, there was no significant difference between the slope of the plots ($\beta$-1) in liquid and gel electrolytes at all scan rates ($\beta$=3.95±0.09, Table 2).

$$\delta(t) = \beta F_{act}(t)$$

The deflection of OSNTs actuator was further investigated according to Euler-Bernoulli's composite beam theory. Such a linear relationship for a cantilever beam can be described by a modified form of deflection equation.

$$\delta(t) = \frac{\gamma l^3}{(EI)_{eff}} F_{act}(t)$$

where $\gamma$ is a constant, l is the actuator length, and $(EI)$eff is the effective flexural rigidity of the composite beam that was obtained above. The calculated $\gamma$ values for various scan rates in liquid and gel electrolytes are given in Table 2. Statistical analysis demonstrated that there was no significant difference ($p < 0.001$) in values of $\gamma$ among different scan rates in liquid and gel electrolytes.

TABLE 2

Calculated $\beta$ and $\gamma$ values at various scan rates in liquid and gel electrolytes.

| Electrolyte | Scan rate (mVs-1) | $\beta$ (reduction) | $\beta$ (Oxidation) | $\gamma$ (reduction) | $\gamma$ (Oxidation) |
|---|---|---|---|---|---|
| Liquid | 10 | 3.88 ± 0.01 | 3.92 ± 0.02 | 7.2 ± 0.02 | 7.29 ± 0.02 |
| | 50 | 3.82 ± 0.02 | 4.00 ± 0.02 | 7.08 ± 0.04 | 7.44 ± 0.03 |
| | 100 | 3.98 ± 0.06 | 4.13 ± 0.02 | 7.38 ± 0.15 | 7.69 ± 0.03 |
| | 200 | 4.01 ± 0.2 | 4.21 ± 0.06 | 7.43 ± 0.37 | 7.84 ± 0.11 |
| Gel | 10 | 3.88 ± 0.01 | 3.92 ± 0.02 | 7.2 ± 0.02 | 7.29 ± 0.02 |
| | 50 | 3.82 ± 0.02 | 4.00 ± 0.02 | 7.08 ± 0.04 | 7.44 ± 0.03 |
| | 100 | 3.98 ± 0.06 | 4.13 ± 0.02 | 7.38 ± 0.15 | 7.69 ± 0.03 |
| | 200 | 4.01 ± 0.2 | 4.21 ± 0.6 | 7.43 ± 0.37 | 7.84 ± 0.11 |

Example 3—High Performance Movable Bioelectronics and Biosensors with Tunable Dynamics Based on Conjugated Polymer Nanofibers and Nanotubes This work demonstrates the utilization of conjugated polymer nanofiber-based actuators for development of movable and flexible neural microelectrodes. Here, a novel strategy is provided to steer the neural electrode projections as a way to deploy electrode sites away from the probe. First, SU-8 based probes were microfabricated with Cr/Au projections/recording sites using standard photolithography, and then the projection sites were articulated with conjugate polymer coatings to enable the probes for controlled actuation/movement. The electroactive coatings were created through electrochemical deposition of polypyrrole on the projection sites in the form of thin films and/or randomly oriented nanofibers. The actuation and electrochemical performance of the fabricated probes was investigated under cerebral physiological conditions. Remarkably, the electrode projections of 50 µm wide with varying length of 0.5 mm and 1 mm were able to deflect ~87 µm and ~262 µm away in artificial cerebrospinal fluid (aCSF), respectively. Given that immune response encapsulation of typical neural probes of 100-200 µm width occurs within 50-100 µm of the probe [15, 33], this approach may be feasible to place electrode sites in more favorable recording environments.

Structural design of probe devices: The optical images of the fabricated probes with two and three actuating projections are shown in F. As indicated, each projection includes a rectangular segment for actuation along with a round site at the projection tip for signal recording. In addition, a fixed recording site has been placed on the device body next to the projection at the same vertical position as the movable recording site.

Morphology of conjugated polymer coatings: To create movable projections, the projection segments of the microfabricated probes were coated with an electroactive layer of PPy in the form of film (FIGS. 19A-C) and randomly oriented PPy nanofibers (PPy NFs) (FIGS. 19D-F). To make PPy NFs layer, PLLA template nanofibers were first electrospun onto gold projections and then they were coated with PPy through electropolymerization process (FIG. 20). The thickness of the resultant PPy layer was controlled by the electrodeposition time and the applied current density, as well. For a comparable study between PPy film and PPy NFs, PPy electrodeposition was conducted at the same current density (0.5 mA/cm$^2$) and for the same deposition time (2 hrs) in both PPy forms. Construction of the PPy active layer on the gold-coated SU-8 passive layer forms a bilayer bending beam actuator, which is responsible for electrochemical actuation of the probe projections. Comparing the SEM images in FIGS. 19C-F, the PPy film formed a continuous coating on the projection surface, while the PPy NFs formed a much porous layer with extremely high surface to volume ratio.

Figures 21A, 21B, 21C, 21D, 21E, 21F:
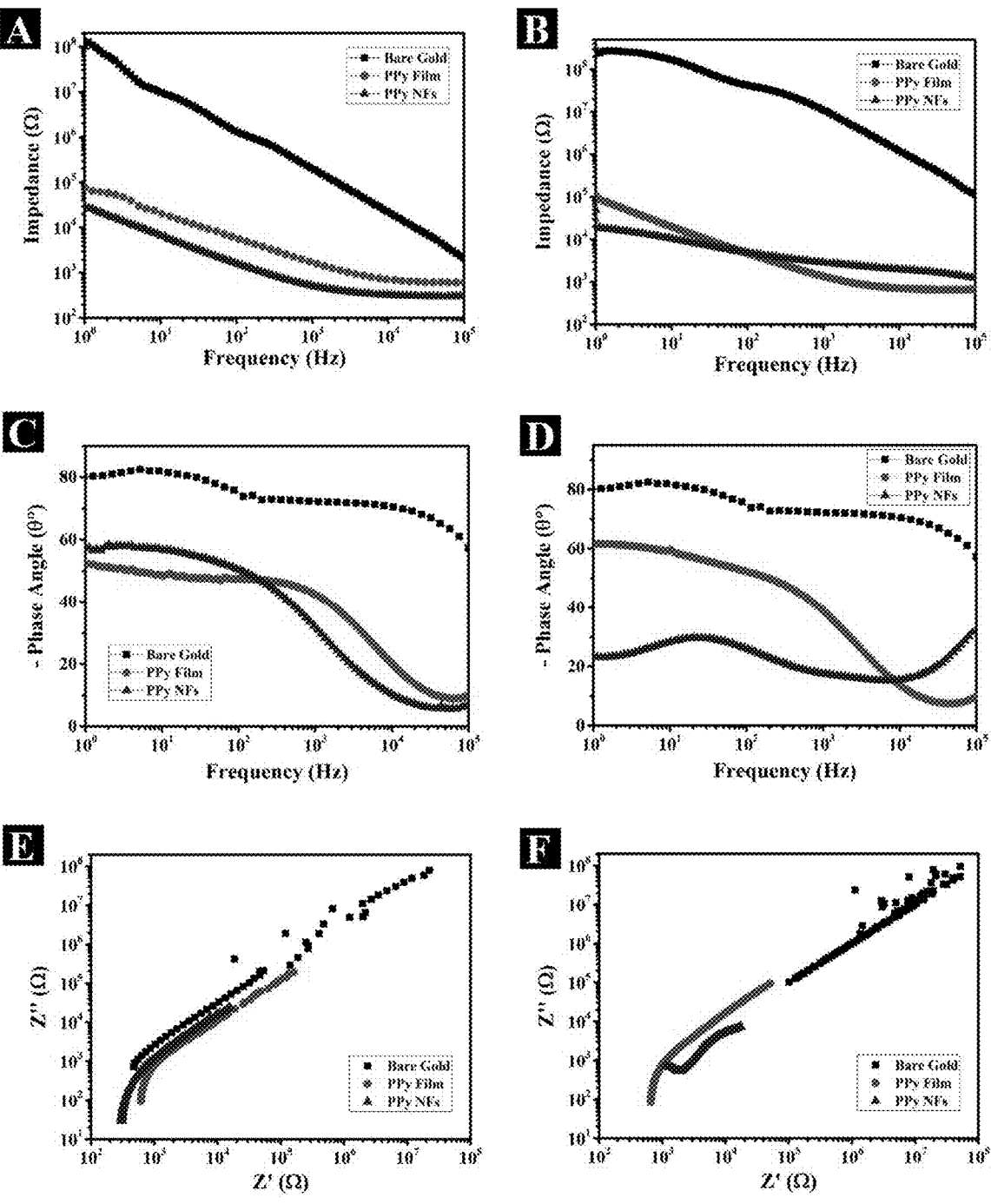
Figures 22A, 22B, 22C, 22D:
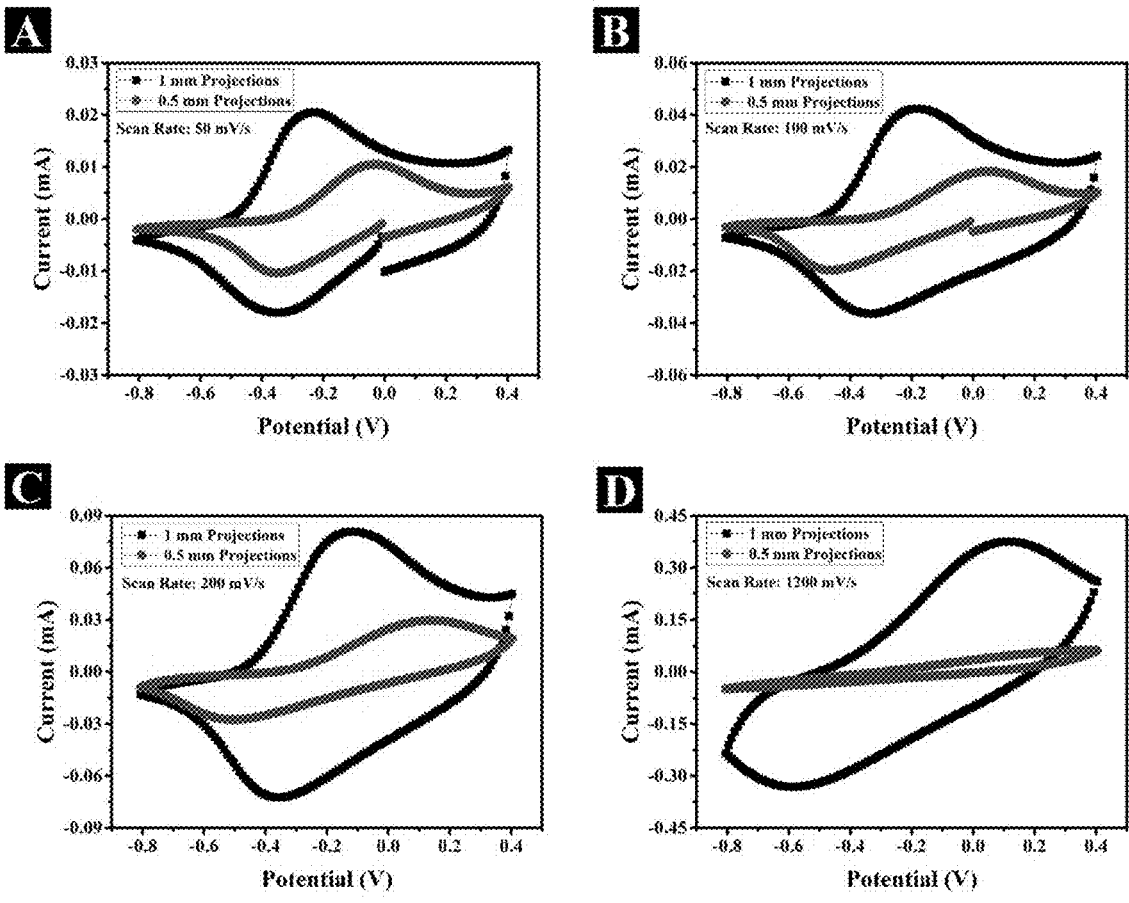

Electrochemical impedance measurements: Electrochemical impedance spectroscopy was used to investigate and compare the electrical conductivity of the projection sites after coating with PPy film and PPy NFs. As demonstrated in FIGS. 21A-B, the impedance of the gold projections was dramatically decreased after coating with PPy film or PPy NFs. For two projections probes, PPy NFs coating exhibited lower impedance across the whole frequency range (1-10$^5$ Hz) than PPy film (FIG. 21A). This is attributed to the higher effective surface area of the PPy nanofibers compared with the film counterpart. However, for three projections probes, PPy NFs coating resulted in a lower impedance at frequencies<100 Hz (FIG. 21A). The phase angle and Nyquist plots in FIGS. 21C-F demonstrate the resistance and capacitance properties of projection sites. As observed in FIGS. 21C-D, the gold projection is predominantly capacitive over the whole frequency range, while both PPy film and PPy NFs coatings decreased the capacitive component of the probes within the frequency range, especially at high frequencies. Noticeably, in probes with three projections, PPy NFs coating exhibited very low capacitive response than film counterpart (FIG. 21D). According to Nyquist plots demonstrated in FIGS. 21E-F, both PPy coatings dramatically decreased the real (Z') and imaginary (Z") impedances. In addition, the PPy NFs coating resulted in lower Z' and Z" values than PPy film that is due to higher effective surface area of PPy NFs. In general, these results confirm that PPy NFs offers improved electrical conductivity over the film counterpart. Accordingly, the PPy NFs were utilized for the following actuation studies.

Actuation performance of the probe devices: The actuation performance of the probe projections coated with PPy NFS were investigated in aCSF electrolyte under cyclic voltammetry (CV). The CV response of the probes with two and three projections at various scan rates of 50, 100, 200, and 1200 mV/s and within the potential range of –0.8 to +0.4 V are presented in FIG. 22. According to the CV curves, the PPy NFs are reduced by applying negative potentials (from 0 V to –0.8 V), then by reversing the potential direction towards positive values they are oxidized. As observed in FIG. 22, the probes with 1 mm projection sites induced higher currents than the probes with 0.5 mm projections. This is presumably due to larger total area of the probes with two projections than that of probes with three projections.

The reduction/oxidation reactions occurs during CV induce volume changes (swelling/shrinking) in the PPy NFs layer, which is responsible for bending movement of the probe projections (FIG. 23). As the PPy NFs are reduced, the solvated cations are inserted into the PPy matrix doped with large PSS counterions, so the PPy NFs expand. Subsequently, as the PPy NFs are oxidized, the solvated cations leave the PPy matrix, therefore, the PPy NFs shrink. This microactuation of the PPy NFs is manifested in macroscale motion of the projection sites. As illustrated in FIG. 23, the PPy coated projections bend outward under the reduction process (PPy NFs expansion), and then they become straight and return to their initial position (in the probe plane) upon subsequent oxidation process.

The charge storage density of the PPy-coated projections sites under electrical stimulation in aCSF electrolyte at various CV scan rates are presented in FIG. 24A. As seen in this figure, the charge storage density of the projection sites was slightly decreased with increasing the scan rate from 50 mV/s to 200 mV/s. However, the charge storage density significantly decreased as the scan rate increased to 1200 mV/s. The mixed ionic and electronic conductivity of conjugated polymers is responsible for their scan rate-dependent actuation response. In fact, the ionic conductivity requires diffusion/transportation of ions, which is a time-dependent phenomenon. By elevating the CV scan rate, the transportation of ions is restricted, therefore, the ionic conductivity and the resultant charge storage density decrease. For probe projections with 1 mm length, the charge storage density of 448.9, 434, 432.8, and 313.4 mC/cm$^2$ were respectively obtained at 50, 100, 200, and 1200 mV/s. For probe projections with 0.5 mm length, the charge storage density of 222, 208.1, 172.4, and 31.2 mC/cm$^2$ were obtained at the scan rates of 50, 100, 200, and 1200 mV/s, respectively.

The projections displacement in aCSF electrolyte under CV at various scan rates were measured and presented in FIG. 24B. As shown, the projection displacement slightly reduced by increasing the CV scan rate from 50 mV/s to 200 mV/s. However, the projections displacement considerably decreased by increasing the scan rate to 1200 mV/s. For 1 mm long projections, the maximum displacement of 267 μm, 252 μm, 248 μm, and 129 μm were respectively obtained at scan rates of 50 mV/s, 100 mV/s, 200 mV/s, and 1200 mV/s. For projections with 0.5 mm length, the maximum displacement of 87.5 μm, 80 μm, 79 μm, and 30 μm were obtained at the scan rates of 50 mV/s, 100 mV/s, 200 mV/s, and 1200 mV/s, and respectively. The reduction in the projections displacement is attributed to the limited ions transportation into/out of the PPy NFs at higher scan rates. These results are in accordance with the limited charge storage density of the PPy NFs as the scan rate elevates (FIG. 24A).

This study demonstrated utilization of conducting polymer nanofibers for articulating movable neural probes. Flexible SU-8 based microelectrodes with two and three projection sites were successfully fabricated using standard photolithography. To make movable probe devices, the projection sites were coated with PPy NFs with enhanced electrical properties than film counterparts. The electrode projections of 50 μm wide with varying length of 0.5 mm and 1 mm were able to deflect~87 μm and ~267 μm away, respectively, in artificial cerebrospinal fluid (aCSF) under CV actuation. The long-term performance of the actuating projections in aCSF was restricted due to electrochemical induced precipitation of calcium phosphate on the on the projections surface. The results of this study may open a new window for development of flexible and movable neural probes.

Example 4—Materials and Methods

SU-8 3005 (negative photoresist) was purchased from MicroChem (Westborough, MA). Positive photoresist (KL6003), 0.26N TMAH Developer, and SU-8 Developer were supplied from Kemlab Inc (Woburn, MA). Plastic photomasks with probe patterns were provided from CAD/Art Service Inc. Cr/glass masks pre-coated with a 500 nm positive photoresist were purchased from Nanofilm (Westlake Village, CA) and patterned with Cr Etchant from MicroChem. Thermal oxide silicon wafers (SiO$_2$ on Si, oxide thickness=2 μm) were supplied from UniversityWafer Inc. Poly(L-lactide) (PLLA, Resomer 210) with the inherent viscosity of 3.3-4.3 dL/g was purchased from Evonik Industries. Benzyl triethylammonium chloride and pyrrole (M$_w$=67.09 g/mol) were supplied from Fisher Scientific. Poly(sodium-p-styrene sulfonate) (NaPSS, M$_w$=70 kD) and chloroform were purchased from Acros-Organics. All ingredients for preparation of aCSF, including NaCl, KCl, CaCl$_2$.2H$_2$O, MgCl$_2$.6H$_2$O, Na$_2$HPO$_4$.7H$_2$O, NaH$_2$PO$_4$.H$_2$O, were supplied from Sigma Aldrich.

Device design and fabrication: In this work, two series of probes with two and three electrode projections of the same width (50 μm) and thickness (~13 μm), but different lengths (1 mm for probes with two projections and 0.5 mm for probes with three projections) were designed as schemed in F6. For in vitro assessments, the electrical traces to the actuating segments (projections) were coupled together. Devices were fabricated using standard photolithography technique at the Nanofabrication Facility at the University of Houston.

The device was fabricated through layer-by-layer photolithography and etching processes. Each layer was patterned using a designed photomask (total of six different photomasks, one for alignment marks and five masks for device patterns) for a 4 inch wafer. In this work, inexpensive plastic photomasks were first used for photolithography, but then switched to Cr/glass masks for their higher quality and ease of processing. The patterns on plastic photomasks were transferred onto Cr/glass masks already coated with a thin layer of positive photoresist. To transfer the patterns, the plastic photomask was placed on the photoresist coated Cr/glass mask and UV exposed at 12.5 mj/cm$^2$ for 7.2 s. Afterwards, the exposed photoresist layer was developed in 0.26N TMAH Developer for 60 s. The patterned Cr/glass mask was wet etched using Cr etchant to create patterns on the mask (etching time=5 min). After etching, the remaining photoresist coating was dissolved in Acetone.

The probe fabrication process is overviewed in FIG. 17 and described hereunder:

A silicon wafer (FIG. 17A) with a thermal oxide layer (SiO$_2$, 2 µm thick) was used as the substrate. The oxide layer served as the final release layer (FIG. 17B).

Patterning and development of first SU-8 layer: a SU-8 layer (~8 µm thick) was spun coated (at 1000 rpm for 30 s) onto the substrate and soft baked at 105° C. for 15 min (very slow heating/cooling). To create the projection gap ( F(c)), the SU-8 layer was patterned using Mask 1 under UV exposure at 12.5 mj/cm$^2$ for 16 s. For post exposure baking, the exposed layer was slowly heated to 95° C. and kept for 3 min and then slowly cooled down to room temperature. The exposed SU-8 layer was developed through immersion in SU-8 developer for 3 min, while shaking.

Deposition of first Cr/Au traces: A thin layer (~2 µm) of positive liftoff resist (KL6003) was spun coated on the wafer at 2500 rpm for 45 s and soft baked at 105° C. for 3 min. Then, the baked layer was UV exposed and patterned using Mask 2 at 12.5 mj/cm$^2$ for 8 s (FIG. 17D). The exposed layer was developed by immersion in 0.26N TMAH developer for 60 s. The patterned wafer was first descummed in oxygen plasma at 100 W for min, and then coated with a thin layer of Cr/Au (Cr thickness=10 nm, Au thickness=100 nm) using e-beam evaporation system (Thermionics evaporator). After Cr/Au deposition, the liftoff resist was removed through bath sonication in acetone (FIG. 17E).

Patterning and development of second SU-8 layer (insulating layer, FIG. 17F): a layer (~5 µm) of SU-8 was spun coated on the wafer (at 3000 rpm for 30 s) and soft baked at 105° C. for 20 min (very slow heating/cooling). Then, the SU-8 layer was UV exposed and patterned using Mask 3 at 12.5 mj/cm$^2$ for 16 s. For post exposure baking, the exposed layer was slowly heated to 95° C. and kept for 5 min and then slowly cooled down to room temperature. The exposed SU-8 layer was developed by immersion in SU-8 developer for 2.5 min (FIG. 17F). The developed SU-8 layers were hard baked at 150° C. for 10 min.

Deposition of second Cr/Au traces: A thin layer (~2 µm) of positive liftoff resist was spun coated on the wafer at 2500 rpm for 45 s and soft baked at 105° C. for 3 min (FIG. 17G). Then, the baked layer was UV exposed and patterned using Mask 4 at 12.5 mj/cm$^2$ for 8 s. The exposed layer was developed by immersion in 0.26N TMAH developer for 60 s. The patterned layer was first descummed in oxygen plasma at 100 W for 5 min and then coated with a thin layer of Cr/Au (Cr thickness=10 nm, Au thickness=100 nm) through e-beam evaporation. After Cr/Au deposition, the liftoff resist was removed using bath sonication in acetone (FIG. 17H).

Patterning and development of third SU-8 layer (FIG. 17I): a SU-8 layer (~5 µm) was spun coated on the wafer (at 3000 rpm for 30 s) and soft baked at 105° C. for 20 min (very slow heating/cooling). The baked SU-8 layer was UV exposed and patterned using Mask 5 at 12.5 mj/cm$^2$ for 12 s. For post exposure baking, the exposed layer was slowly heated to 95° C. and kept for 5 min and then slowly cooled down to room temperature. The exposed SU-8 layer was developed by immersion in SU-8 developer for 2.5 min (FIG. 17I). The developed SU-8 layers were hard baked at 150° C. for 15 min.

To release the probe devices from the substrate, the wafer was immersed in HF solution (30%) to remove the sacrificial SiO$_2$ layer (FIG. 17J). The released probes were collected from the HF solution and transferred to water containers for serial wash. Ultimately, the fabricated probes were annealed at 200° C. to release the residual stresses in the SU-8 layers.

Coating of device projections with conjugated polymer film: The projections sites of the fabricated devices were electrochemically coated with an electroactive layer of polypyrrole (PPy) film. PPy was electrodeposited on the projection sites using 0.2 M pyrrole:PSS aqueous electrolyte at the current density of 0.5 mA/cm$^2$ for 2 hrs using Autolab PGSTAT 128N (Metrohm, USA) in galvanostatic mode with a two-electrode configuration at room temperature.

Coating of device projections with conjugated polymer nanofibers: To construct PPy nanofibers (PPy NFs) on the projection sites, first template poly(L-lactide) (PLLA) nanofibers were electrospun onto the gold projection sites and then PPy electrodeposited around the template nanofibers. For electrospinning, a homogeneous solution of PLLA (3 wt. %) in chloroform was prepared by adding 230 mg PLLA in 5 ml chloroform and stirring the mixture overnight at room temperature. To enhance the solution charge strength, 23 mg Benzyl triethylammonium chloride (an organic salt) was added to the solution prior to stirring. PLLA template nanofibers were electrospun using a syringe pump with the spinneret gauge of 23, an electric field of 0.91 kV/cm, a flow rate of 50 µL/hr, and a syringe-substrate distance of 11 cm for 30 s. Temperature and humidity were kept constant at 26° C. and 30%, respectively. For PPy deposition, 0.2 M pyrrole:PSS aqueous electrolyte was prepared by dissolving 277 µL pyrrole monomer and 824 mg NaPSS in 20 ml deionized water. Prior to electrodeposition, the probe device was kept in the electrolyte for 30 min to ensure that the solution has completely diffused into the fiber interspaces. Then, the electrodeposition was carried out at the current density of 0.5 mA/cm$^2$ for 2 hrs. Ultimately, to remove the uncoated template nanofibers from the surrounding areas of projection sites, the probe device was immersed in chloroform for 30 s.

Preparation of artificial cerebrospinal fluid (aCSF): To prepare the aCSF, first two different solutions containing the aCSF compounds were prepared. Solution A was composed of 8.66 g NaCl, 0.224 g KCl, 0.206 g CaCl$_2$.2H$_2$O, and 0.163 g MgCl$_2$.6H$_2$O in 500 ml deionized water. Solution B was composed of 0.214 g Na$_2$HPO c$_4$.7H$_2$O and 0.027 g NaH$_2$PO$_4$.H$_2$O in 500 ml deionized water. Then, an equal volume of solutions (1:1 ratio) were mixed to end up with a multivalent physiological ion solution of aCSF.

Projections actuation using cyclic voltammetry: Actuation of the probe projections was performed through cyclic voltammetry (CV) using Autolab PGSTAT 128 in a three-electrode configuration with a saturated Ag/AgCl reference electrode and a 1×2 cm Pt foil as counter electrode. The CV was performed within the potential range of −0.8 to +0.4 V at various scan rates of 50, 100, 200, and 1200 mV/s. The actuation behavior of the probe devices was assessed in aCSF electrolyte. Prior to actuation, the probe projections were primed in the electrolyte at 100 mV/s for ten cycles.

Electrochemical impedance spectroscopy (EIS): An Autolab PGSTAT12 and Frequency Response Analyzer software (EcoChemie B.V., Netherlands) were used to record impedance spectra of electrodesites for the neural probes. The impedance measurement was conducted in the aCSF electrolyte using a three-electrode cell configuration. The working electrode was connected to electrode site through a connector. The counter electrode was connected to a platinum foil that was placed in the cell container, and an Ag/AgCl electrode was used as reference electrode. An AC sinusoidal signal of 5 mV in amplitude was used to record the impedance over a frequency range of 1-10$^5$ Hz.

Projection deflection measurement: The bending deflection of the probe projection was recorded using a digital camera (Dino-Lite) with 30 frames per second. The recorded videos were then processed using an open-source software (Tracker 5.0.6) to measure the projection deflection upon actuation.

Structural characterization of the probe devices: The structure evaluation of the fabricated probes was performed using optical upright and stereo microscopes (Carl Zeiss Imager Z1, Germany). The surface morphology of the probe projections after coating with conjugated polymer layer was characterized using Field Emission Scanning Electron Microscopy (FESEM, FEI 235). Samples were mounted on aluminum stubs by carbon tape and a carbon paint was used for grounding. Prior to microscopy, probes were sputter-coated with a thin layer of gold using Denton Sputter Coater for 60 s at 40 mA.

The shape and geometry of the microprobe is similar to implantable Michigan neural electrodes.[13e, 33] Using standard layer-by-layer photolithography processes, a miniaturized device was microfabricated consisting of three gold-coated cantilevers (500 μm×50 μm, marked as "P"), six gold circular electrode sites (30 μm diameter, marked "Q"), and nine squared contact pads (150 μm×150 μm, marked "R") on a 13 μm polymer substrate (FIGS. 20A-B). Each cantilever and electrode site has a separate circuit and is connected to an individual contact pad by 20 μm wide gold traces. Finally, the miniaturized device was assembled on a printed circuit board and wire-bonded to the board through the contact pads (FIG. 20C). As shown in FIGS. 20D-E, the OSNTs were coated on the microcantilevers (P) and were subjected to CV potential sweeps (within a range of −0.8 to +0.4 V at various scan rates of 50 to 200 mV s$^{-1}$). The displacement of each microcantilever was separately controlled by adjusting the scan rate (e.g., a displacement of ~80 μm was obtained at scan rate 200 mVs$^{-1}$, FIG. 20D). To assess the effect of microcantilevers deflection on electrical performance of the movable electrode sites (Q) located on the tip of microcantilevers, the impedance of the electrodes was measured before and after actuation and was compared with that of the fixed reference electrodes. Notably, the impedance of the bare gold electrode sites remained the same as before actuation (~190 kΩ at 1 kHz, FIG. 24). This microprobe can be potentially implanted in the brain and neural signal recordings which are adversely affected by reactive tissue responses and/or displacement of the neurons [34] may be enhanced by adjusting the position of recording sites (Q) located on the movable microcantilevers (P).

Figures 26A, 26B, 26C, 26D, 26E, 26F, 26G, 26H, 26I, 26J, 26K, 26L:
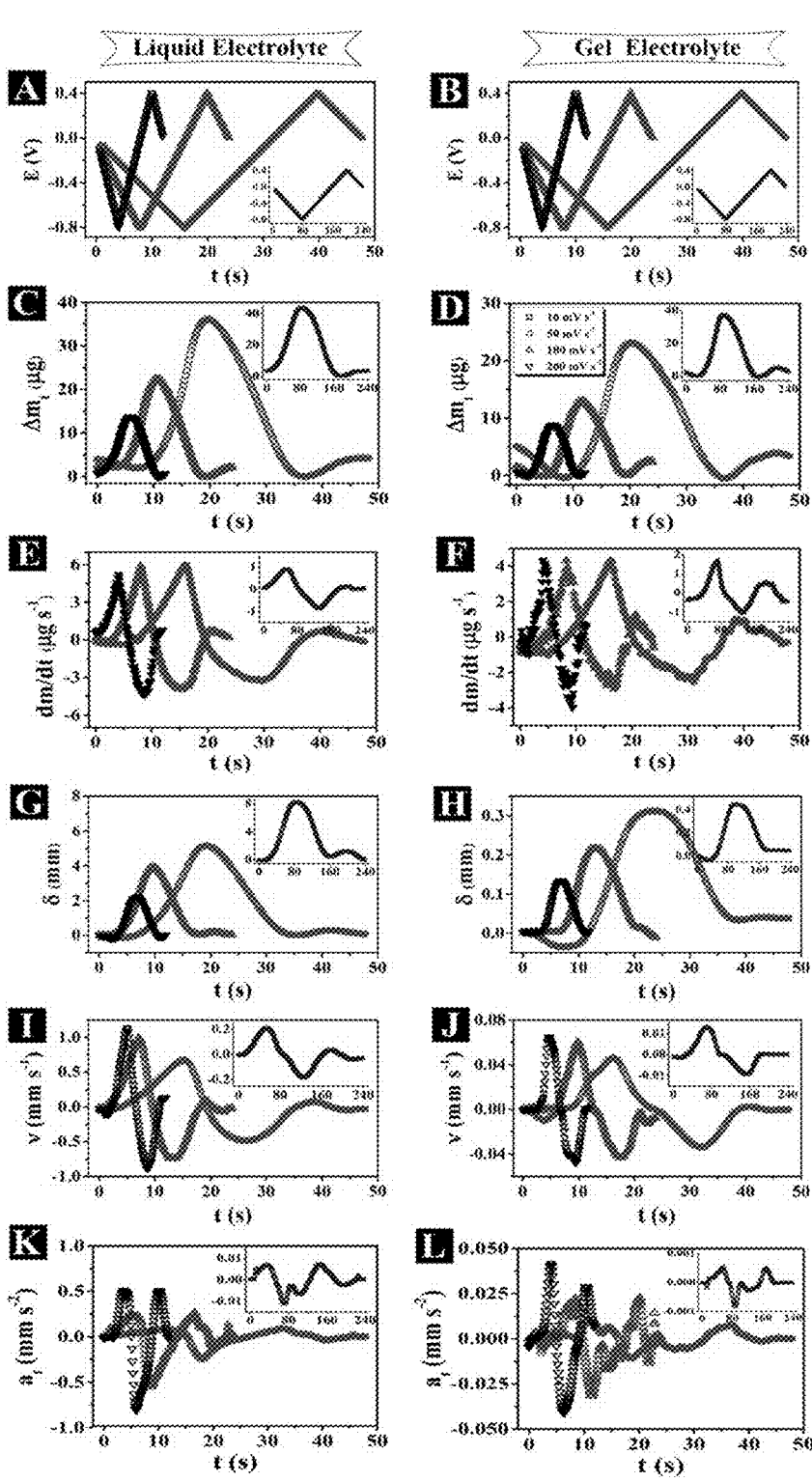

Performance and Durability: Considering that the actuation strain in the electrochemical actuator depends on the electro-mechanical efficiency, the power consumption per generated strain is a particularly relevant metric to evaluate the actuation's performance. FIG. 26A illustrates the power consumption/strain of the OSNTs actuator at various CV scan rates in liquid and gel electrolytes. As shown, the power consumption/strain of the OSNTs actuator is within the ranges of 0.5-9.1 mW cm$^{-2}$%$^{-1}$ in liquid electrolyte, and 9-159 mW cm-2%_$^1$ in gel electrolyte. The low power consumption/strain values for the OSNTs actuator operating in liquid electrolyte mark a profound improvement compared with previously reported electrochemical actuators operating in liquid[29] and air[4b, 24, 30] (FIG. 26A). Notably, the OSNTs actuator yielded relatively low power consumption to strain in the gel electrolyte, which is comparable with air operating actuators and much less than those operating in liquid electrolyte. Such low power consumption/strain vastly raises their utility in various applications where power consumption/strain is desired to be minimal with maximal yield and actuation power.

Figures 27A, 27B, 27C, 27D, 27E, 27F:
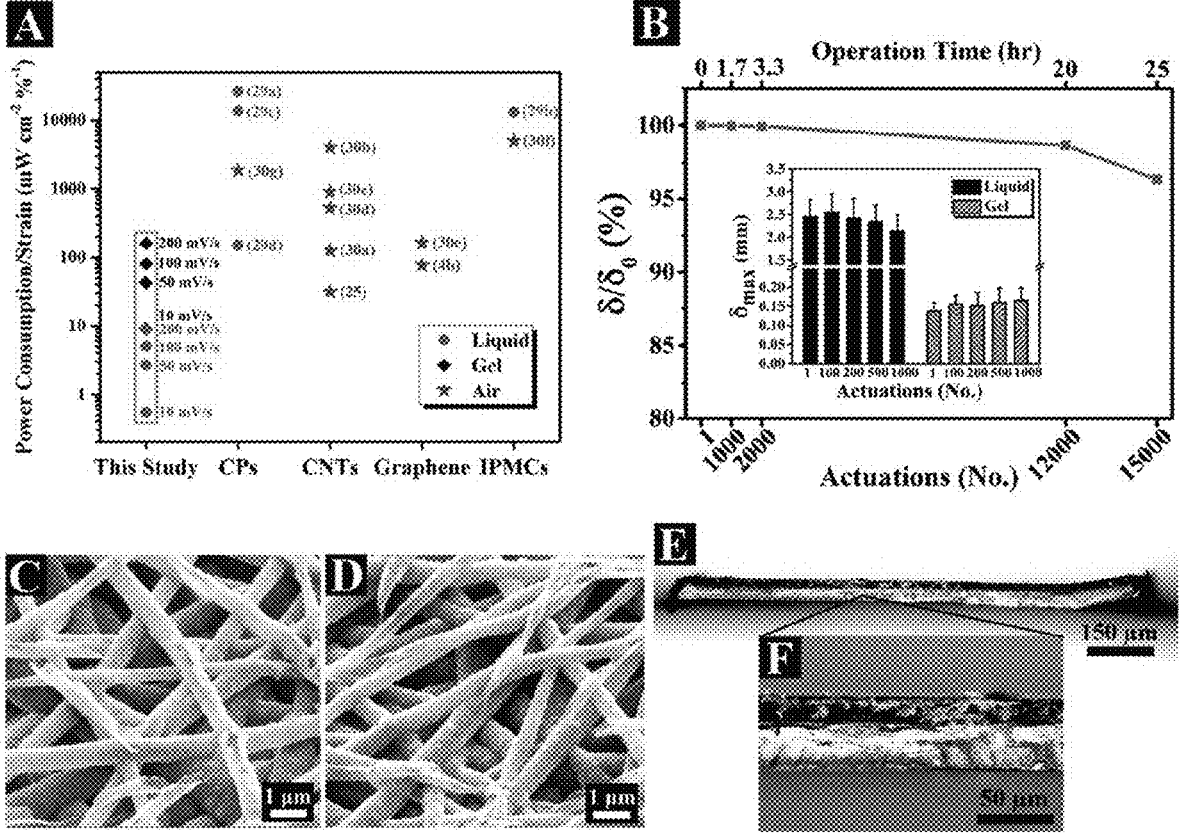

Further, the long-term stability (i.e., mechanical durability) of the OSNTs device was evaluated over a great number of actuations (FIG. 27B). Remarkably, the OSNTs device showed a bending stability >96.5% in liquid electrolyte over 15,000 actuations (25 hours of continuous operation) at scan rate 200 mV s$^{-1}$ (equivalent to cycling frequency 0.08 Hz). While electron micrographs (FIG. 27C-D) and optical micrographs (FIG. 27E-F) did not indicate any obvious mechanical damage or delamination of OSNTs over the course of actuation, the slight degradation in actuator displacement (~3.5%) may be attributed to the nanoscale deformation and stress relaxation in OSNTs. These results suggest that the OSNTs actuator can effectively operate in liquid and gel electrolytes and can mechanically endure a large number of actuations. In fact, this OSNTs actuator exhibited superior long-term stability compared with previously reported CP-based actuators operating in liquid electrolyte (e.g., CP film[31] with substantial bending degradation after 11 hr).[31-32]

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. REFERENCES

The following references, to the extent that they provide exemplary procedural or other details supplementary to those set forth herein, are specifically incorporated herein by reference:

Examples 1-2

[1] C. Paulino, V. Kalienkova, A. K. Lam, Y. Neldner, R. Dutzler, *Nature* 2017, 552, 421-425.

[2] a) S. M. Mirvakili, I. W. Hunter, *Adv. Mater.* 2018, 30, 1704407; b) Y. Bar-Cohen, *Electroactive polymer (EAP) actuators as artificial muscles: reality, potential, and challenges, Vol.* 136, SPIE press, 2004.

[3] a) M. Ghilardi, H. Boys, P. Török, J. J. Busfield, F. Carpi, *Sci. Rep.* 2019, 9, 1-10; b) F. Carpi, R. Kornbluh, P. Sommer-Larsen, G. Alici, *Bioinspir. Biornim.* 2011, 6, 045006; c) Y. Zhao, L. Song, Z. Zhang, L. Qu, *Energy Environ. Sci.* 2013, 6, 3520-3536; d) F. Carpi, E. Smela, *Biomedical applications of electroactive polymer actuators,* John Wiley & Sons, 2009.

[4] a) Y. Yan, T. Santaniello, L. G. Bettini, C. Minnai, A. Bellacicca, R. Porotti, I. Denti, G. Faraone, M. Merlini, C. Lenardi, *Adv. Mater.* 2017, 29, 1606109; b) L. Lu, J. Liu, Y. Hu, Y. Zhang, W. Chen, *Adv. Mater.* 2013, 25, 1270-1274.

[5] I. Takeuchi, K. Asaka, K. Kiyohara, T. Sugino, N. Terasawa, K. Mukai, T. Fukushima, T. Aida, *Electrochim. Acta* 2009, 54, 1762-1768.

[6] J. Kim, J.-H. Jeon, H.-J. Kim, H. Lim, I.-K. Oh, *Acs Nano* 2014, 8, 2986-2997.

[7] C. Lu, Y. Yang, J. Wang, R. Fu, X. Zhao, L. Zhao, Y. Ming, Y. Hu, H. Lin, X. Tao, *Nat. Commun* 2018, 9, 1-11.

[8] L. Kong, W. Chen, *Adv. Mater.* 2014, 26, 1025-1043.

[9] K. Kaneto, M. Kaneko, Y. Min, A. G. MacDiarmid, *Synth. Met.* 1995, 71, 2211-2212.

[10] a) C. Dingler, H. Müller, M. Wieland, D. Fauser, H. Steeb, S. Ludwigs, *Adv. Mater.* 2021, 33, 2007982; b) J. Gladisch, E. Stavrinidou, S. Ghosh, A. Giovannitti, M. Moser, I. Zozoulenko, I. McCulloch, M. Berggren, *Adv. Sci.* 2020, 7, 1901144; c) M. M. Hamedi, V. E. Campbell, P. Rothemund, F. Gilder, D. C. Christodouleas, J. F. Bloch, G. M. Whitesides, *Adv. Funct. Mater.* 2016, 26, 2446-2453; d) L. Bay, K. West, P. Sommer-Larsen, S. Skaarup, M. Benslimane, *Adv. Mater.* 2003, 15, 310-313.

[11] a) M. R. Abidian, D. H. Kim, D. C. Martin, *Adv. Mater.* 2006, 18, 405-409; b) E. Smela, *Adv. Mater.* 2003, 15, 481-494; c) M. Hamedi, R. Forchheimer, O. Inganäs, *Nat. Mater* 2007, 6, 357-362.

[12] a) Q. Pei, O. Inganaes, *J. Phys. Chem* 1992, 96, 10507-10514; b) L. Bay, T. Jacobsen, S. Skaarup, K. West, *J. Phys. Chem. B* 2001, 105, 8492-8497.

[13] a) R. Wadhwa, C. F. Lagenaur, X. T. Cui, *J. Controlled Release* 2006, 110, 531-541; b) M. Berggren, A. Richter-Dahlfors, *Adv. Mater.* 2007, 19, 3201-3213; c) J. Rivnay, S. Inal, A. Salleo, R. M. Owens, M. Berggren, G. G. Malliaras, *Nat. Rev.* Mater. 2018, 3, 1-14; d) M. R. Abidian, J. M. Corey, D. R. Kipke, D. C. Martin, *small* 2010, 6, 421-429; e) M. R. Abidian, K. A. Ludwig, T. C. Marzullo, D. C. Martin, D. R. Kipke, *Adv. Mater.* 2009, 21, 3764-3770; f) M. Fahlman, S. Fabiano, V. Gueskine, D. Simon, M. Berggren, X. Crispin, *Nat. Rev. Mater.* 2019, 4, 627-650.

[14] R. Temmer, I. Must, F. Kaasik, A. Aabloo, T. Tamm, *Sensors Actuators B: Chem.* 2012, 166, 411-418.

[15] a) B. Yan, Y. Wu, L. Guo, *Polymers* 2017, 9, 446; b) F. Hu, Y. Xue, J. Xu, B. Lu, *Frontiers in Robotics and AI* 2019, 6, 114.

[16] G. Yang, K. L. Kampstra, M. R. Abidian, *Adv. Mater.* 2014, 26, 4954-4960.

[17] a) C. S. Kim, S. M. Oh, *J. Power Sources* 2002, 109, 98-104; b) S. Liang, W. Yan, X. Wu, Y. Zhang, Y. Zhu, H. Wang, Y. Wu, *Solid State Ionics* 2018, 318, 2-18.

[18] S.-K. Lee, Y. Choi, W. Sim, S. S. Yang, H. An, J. J. Pak, in *Smart Structures and Materials* 2000*: Electroactive Polymer Actuators and Devices (EAPAD)*, *Vol.* 3987, International Society for Optics and Photonics, 2000, pp. 291-299.

[19] a) R. Pomfret, G. Miranpuri, K. Sillay, *Annals of neurosciences* 2013, 20, 118; b) T. Parupudi, R. Rahimi, M. Ammirati, R. Sundararajan, A. L. Garner, B. Ziaie, *Electrophoresis* 2018, 39, 2262-2269; c) K. Sillay, D. Schomberg, A. Hinchman, L. Kumbier, C. Ross, K. Kubota, E. Brodsky, G. Miranpuri, *J. Neural Eng.* 2012, 9, 026009.

[20] E. Smela, *MRS Bull.* 2011, 33, 197-204.

[21] a) E. Stavrinidou, P. Leleux, H. Rajaona, D. Khodagholy, J. Rivnay, M. Lindau, S. Sanaur, G. G. Malliaras, *Adv. Mater.* 2013, 25, 4488-4493; b) M. Eslamian, M. Antensteiner, M. R. Abidian, in 2018 *40th Annual International Conference of the IEEE Engineering in Medicine and Biology Society (EMBC)*, IEEE, 2018, pp. 4472-4475.

[22] a) D. Wang, C. Lu, J. Zhao, S. Han, M. Wu, W. Chen, *RSCAdv.* 2017, 7, 31264-31271; b) N. Terasawa, K. Asaka, *Langmuir* 2016, 32, 7210-7218; c) Y. Li, R.

Tanigawa, H. Okuzaki, *Smart Mater. Struct.* 2014, 23, 074010; d) H. Okuzaki, S. Takagi, F. Hishiki, R. Tanigawa, *Sensors Actuators B: Chem.* 2014, 194, 59-63.

[23] J.-P. Péraud, A. J. Nonaka, J. B. Bell, A. Donev, A. L. Garcia, *PNAS* 2017, 114, 10829-10833.

[24] G. Wu, X. Wu, Y. Xu, H. Cheng, J. Meng, Q. Yu, X. Shi, K. Zhang, W. Chen, S. Chen, *Adv. Mater.* 2019, 31, 1806492.

[25] A. Della Santa, D. De Rossi, A. Mazzoldi, *Synth. Met.* 1997, 90, 93-100.

[26] a) M. Christophersen, B. Shapiro, E. Smela, *Sensors Actuators B: Chem.* 2006, 115, 596-609; b) B. Shapiro, E. Smela, *J. Intell. Mater. Syst. Struct.* 2007, 18, 181-186.

[27] J. M. Gere, S. P. Timoshenko, *Comp.*, Boston 1984.

[28] S. Timoshenko, *Josa* 1925, 11, 233-255.

[29] a) J. M. Sansinena, J. Gao, H. L. Wang, *Adv. Funct. Mater.* 2003, 13, 703-709; b) V. Panwar, J.-H. Jeon, G. Anoop, H. J. Lee, I.-K. Oh, J. Y. Jo, *J. Mater. Chem.* A 2015, 3, 19718 19727; c) J. Ding, D. Zhou, G. Spinks, G. Wallace, S. Forsyth, M. Forsyth, D. MacFarlane, *Chem. Mater.* 2003, 15, 2392-2398; d) R. Kiefer, J. G. Martinez, A. Keskula, G. Anbarjafari, A. Aabloo, T. F. Otero, *Sensors Actuators B: Chem.* 2016, 233, 328-336.

[30] a) O. Kim, H. Kim, U. H. Choi, M. J. Park, *Nat. Commun* 2016, 7, 1-8; b) J. Li, W. Ma, L. Song, Z. Niu, L. Cai, Q. Zeng, X. Zhang, H. Dong, D. Zhao, W. Zhou, *Nano Lett.* 2011, 11, 4636-4641; c) N. Terasawa, N. Ono, K. Mukai, T. Koga, N. Higashi, K. Asaka, *Carbon* 2012, 50, 311-320; d) K. Mukai, K. Asaka, T. Sugino, K. Kiyohara, I. Takeuchi, N. Terasawa, D. N. Futaba, K. Hata, T. Fukushima, T. Aida, *Adv. Mater.* 2009, 21, 1582 1585; e) L. Lu, J. Liu, Y. Hu, Y. Zhang, H. Randriamahazaka, W. Chen, *Adv. Mater.* 2012, 24, 4317-4321; f) J.-W. Lee, Y.-T. Yoo, J. Y. Lee, *ACS Appl. Mater. Interfaces* 2014, 6, 1266-1271; g) G. Wu, Y. Hu, J. Zhao, T. Lan, D. Wang, Y. Liu, W. Chen, *Small* 2016, 12, 4986-4992.

[31] K. Idla, O. Inganäs, M. Strandberg, *Electrochim. Acta* 2000, 45, 2121-2130.

[32] a) B. Kim, C. Too, J. Kwon, J. Ko, G. Wallace, *Synth. Met.* 2011,161, 1130-1132; b) W. Lu, A. G. Fadeev, B. Qi, E. Smela, B. R. Mattes, J. Ding, G. M. Spinks, J. Mazurkiewicz, D. Zhou, G. G. Wallace, *Science* 2002, 297, 983-987.

[33] P. J. Rousche, D. S. Pellinen, D. P. Pivin, J. C. Williams, R. J. Vetter, D. R. Kipke, *IEEE Trans. Biomed. Eng.* 2001, 48, 361-371.

[34] V. S. Polikov, P. A. Tresco, W. M. Reichert, *J. Neurosci. Methods* 2005, 148, 1-18.

Examples 3-4

1. Hong, G. and C. M. Lieber, *Novel electrode technologies for neural recordings.* Nature Reviews Neuroscience, 2019. 20(6): p. 330-345.

2. Frank, J. A., M.-J. Antonini, and P. Anikeeva, *Next-generation interfaces for studying neural function.* Nature biotechnology, 2019. 37(9): p. 1013-1023.

3. Wilson, B. S., et al., *Better speech recognition with cochlear implants.* Nature, 1991. 352(6332): p. 236-238.

4. Zrenner, E., *Will retinal implants restore vision?* Science, 2002. 295(5557): p. 1022-1025.

5. Jackson, A. and J. B. Zimmermann, *Neural interfaces for the brain and spinal cord—restoring motor function.* Nature Reviews Neurology, 2012. 8(12): p. 690.

6. Raspopovic, S., et al., *Restoring natural sensory feedback in real-time bidirectional hand prostheses*. Science translational medicine, 2014. 6(222): p. 222ra19-222ra19.

7. Stacey, W. C. and B. Litt, *Technology insight: neuroengineering and epilepsy-designing devices for seizure control*. Nature clinical practice Neurology, 2008. 4(4): p. 190-201.

8. Kringelbach, M. L., et al., *Translational principles of deep brain stimulation*. Nature Reviews Neuroscience, 2007. 8(8): p. 623-635.

9. Hubel, D. H., *Tungsten microelectrode for recording from single units*. Science, 1957. 125(3247): p. 549-550.

10. Wise, K. D., J. B. Angell, and A. Starr, *An integrated-circuit approach to extracellular microelectrodes*. IEEE transactions on biomedical engineering, 1970(3): p. 238-247.

11. Wise, K. D., et al., *Wireless implantable microsystems: high-density electronic interfaces to the nervous system*. Proceedings of the IEEE, 2004. 92(1): p. 76-97.

12. Campbell, P. K., K. E. Jones, and R. A. Normann, *A 100 electrode intracortical array: structural variability*. Biomed. Sci. Instrum, 1990. 26: p. 161-165.

13. Jun, J. J., et al., *Fully integrated silicon probes for high-density recording of neural activity*. Nature, 2017. 551(7679): p. 232-236.

14. Lee, M., et al., *Soft high-resolution neural interfacing probes: Materials and design approaches*. Nano letters, 2019. 19(5): p. 2741-2749.

15. Polikov, V. S., P. A. Tresco, and W. M. Reichert, *Response of brain tissue to chronically implanted neural electrodes*. Journal of neuroscience methods, 2005. 148 (1): p. 1-18.

16. Kim, J., R. Ghaffari, and D.-H. Kim, *The quest for miniaturized soft bioelectronic devices*. Nature Biomedical Engineering, 2017. 1(3): p. 1-4.

17. Suo, Z., et al., *Mechanics of rollable and foldable film-on-foil electronics*. Applied Physics Letters, 1999. 74(8): p. 1177-1179.

18. Kim, B. J. and E. Meng, *Review of polymer MEMS micromachining*. Journal of Micromechanics and Microengineering, 2015. 26(1): p. 013001.

19. Weltman, A., J. Yoo, and E. Meng, *Flexible, penetrating brain probes enabled by advances in polymer microfabrication*. Micromachines, 2016. 7(10): p. 180.

20. Du, Z. J., et al., *Ultrasoft microwire neural electrodes improve chronic tissue integration*. Acta biomaterialia, 2017. 53: p. 46-58.

21. Kim, T.-i., et al., *Injectable, cellular-scale optoelectronics with applications for wireless optogenetics*. Science, 2013. 340(6129): p. 211-216.

22. Lu, L., et al., *Soft and MRI compatible neural electrodes from carbon nanotube fibers*. Nano letters, 2019. 19(3): p. 1577-1586.

23. Vetter, R. J., et al., *Chronic neural recording using silicon-substrate microelectrode arrays implanted in cerebral cortex*. IEEE Transactions on Biomedical Engineering, 2004. 51(6): p. 896-904.

24. Engel, A. K., et al., *Invasive recordings from the human brain: clinical insights and beyond*. Nature Reviews Neuroscience, 2005. 6(1): p. 35-47.

25. Muthuswamy, J., S. Anand, and A. Sridharan, *Adaptive movable neural interfaces for monitoring single neurons in the brain*. Frontiers in neuroscience, 2011. 5: p. 94.

26. Muthuswamy, J., et al., *An array of microactuated microelectrodes for monitoring single-neuronal activity in rodents*. IEEE Transactions on Biomedical Engineering, 2005. 52(8): p. 1470-1477.

27. Cham, J. G., et al., *Semi-chronic motorized microdrive and control algorithm for autonomously isolating and maintaining optimal extracellular action potentials*. Journal of Neurophysiology, 2005. 93(1): p. 570-579.

28. Pang, C., et al. *Electrolysis-based parylene balloon actuators for movable neural probes*. in 2007 2nd IEEE International Conference on Nano/Micro Engineered and Molecular Systems. 2007. IEEE.

29. Cui, X., et al., *Electrochemical deposition and characterization of conducting polymer polypyrrole/PSS on multichannel neural probes*. Sensors and Actuators A: Physical, 2001. 93(1): p. 8-18.

30. Cui, X., et al., *In vivo studies of polypyrrole/peptide coated neural probes*. Biomaterials, 2003. 24(5): p. 777-787.

31. Abidian, M. R., D. H. Kim, and D. C. Martin, *Conducting polymer nanotubes for controlled drug release*. Advanced materials, 2006. 18(4): p. 405-409.

32. Abidian, M. R., et al. *In-vivo evaluation of chronically implanted neural microelectrode arrays modified with poly (3, 4-ethylenedioxythiophene) nanotubes*. in 2007 3rd International IEEE/EMBS Conference on Neural Engineering. 2007. IEEE.

33. Biran, R., D. C. Martin, and P. A. Tresco, *Neuronal cell loss accompanies the brain tissue response to chronically implanted silicon microelectrode arrays*. Experimental neurology, 2005. 195(1): p. 115-126.

34. Lei, Y., et al., *Electrochemical induced calcium phosphate precipitation: importance of local pH*. Environmental science & *technology*, 2017. 51(19): p. 11156-11164.

What is claimed:

1. A neural probe device comprising:

a proximal portion;

a shank extending from the proximal portion along a longitudinal axis; and at least one movable projection disposed along the shank comprising a rectangular segment and a rounded tip comprising a recording site for signal recording, wherein the rectangular segment is formed from an organic semiconductor nanotube (OSNT) comprising at least one conducting polymer and polystyrene sulfonate (PSS) such that the OSNT on the rectangular segment bends transversely to the longitudinal axis of the shank in response to an applied voltage.

2. The neural probe of claim 1, wherein the at least one movable projection further comprises at least one trace formed from a conductive metal.

3. The neural probe of claim 2, wherein the conductive metal is chromium and/or gold.

4. The neural probe of claim 1, wherein the at least one movable projection comprises one or more structural photoresist layer.

5. The neural probe of claim 4, wherein the one or more structural photoresist layer is SU-8.

6. The neural probe of claim 1, wherein the at least one movable projection comprises two or three movable projections.

7. The neural probe of claim 1, wherein the at least one movable projection has a length of about 0.5 mm to about 1 mm.

8. The neural probe of claim 1, wherein the at least one movable projection has a width of about 25 to 75 μm and a thickness of 5 to 20 μm.

9. The neural probe of claim 3, the thickness of the gold and/or chromium are 1 to 3 μm.

10. The neural probe of claim 1, wherein the conductive polymer is polypyrrole.

11. The neural probe of claim 1, wherein the neural probe device is implantable.

12. A method of using a neural probe device of claim 1 for neural recording or stimulation.

\* \* \* \* \*